(12) United States Patent
Tezuka et al.

(10) Patent No.: US 7,998,478 B2
(45) Date of Patent: *Aug. 16, 2011

(54) PHARMACEUTICAL COMPOSITION FOR TREATING IMMUNE DISEASES

(75) Inventors: Katsunari Tezuka, Kanagawa (JP); Yoshihiro Watanabe, Kanagawa (JP); Ryo Abe, Kanagawa (JP)

(73) Assignee: Japan Tobacco, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/268,832

(22) Filed: Nov. 11, 2008

(65) Prior Publication Data

US 2009/0148444 A1    Jun. 11, 2009

Related U.S. Application Data

(63) Continuation of application No. 10/729,880, filed on Dec. 5, 2003, now Pat. No. 7,465,445, which is a continuation of application No. 09/830,548, filed as application No. PCT/JP00/05868 on Aug. 30, 2000, now abandoned.

(30) Foreign Application Priority Data

Aug. 30, 1999   (JP) .................................. 11-242672
Aug. 24, 2000   (JP) .................................. 2000-254680

(51) Int. Cl.
*A61K 39/395* (2006.01)

(52) U.S. Cl. ................................................... 424/130.1

(58) Field of Classification Search ........................ None
See application file for complete search history.

(56) References Cited

U.S. PATENT DOCUMENTS

| | | | |
|---|---|---|---|
| 5,484,892 A | 1/1996 | Tedder et al. | |
| 5,506,126 A | 4/1996 | Seed et al. | |
| 5,521,288 A | 5/1996 | Linsley et al. | |
| 5,747,461 A | 5/1998 | Markov | |
| 5,770,197 A | 6/1998 | Linsley et al. | |
| 5,914,112 A | 6/1999 | Bednar et al. | |
| 6,075,181 A | 6/2000 | Kucherlapati | |
| 6,440,418 B1 | 8/2002 | Black et al. | |
| 6,531,505 B2 | 3/2003 | Xu et al. | |
| 6,803,039 B2 | 10/2004 | Tsuji et al. | |
| 7,030,225 B1 | 4/2006 | Tamatani et al. | |
| 7,045,615 B2 | 5/2006 | Tamatani et al. | |
| 7,112,655 B1 | 9/2006 | Tamatani et al. | |
| 7,125,551 B2 | 10/2006 | Kroczek | |
| 7,132,099 B2 | 11/2006 | Kroczek | |
| 7,166,283 B2 | 1/2007 | Tsuji et al. | |
| 7,196,175 B2 | 3/2007 | Tamatani et al. | |
| 7,217,792 B2 | 5/2007 | Tamatani et al. | |
| 7,226,909 B2 | 6/2007 | Tamatani et al. | |
| 7,247,612 B2 | 7/2007 | Tamatani et al. | |
| 7,259,147 B2 | 8/2007 | Tamatani et al. | |
| 7,259,247 B1 | 8/2007 | Kroczek | |
| 7,279,560 B2 | 10/2007 | Tamatani et al. | |
| 7,294,473 B2 | 11/2007 | Tamatani et al. | |
| 7,438,905 B2 | 10/2008 | Suzuki et al. | |
| 7,465,445 B2 * | 12/2008 | Tezuka et al. | 424/130.1 |
| 2002/0151685 A1 | 10/2002 | Tamatani et al. | |
| 2002/0156242 A1 | 10/2002 | Tamatani et al. | |
| 2002/0164697 A1 | 11/2002 | Coyle et al. | |
| 2003/0083472 A1 | 5/2003 | Tamatani et al. | |
| 2004/0131608 A1 | 7/2004 | Watanabe | |
| 2004/0229790 A1 | 11/2004 | Tezuka et al. | |
| 2008/0199466 A1 * | 8/2008 | Tsuji et al. | 424/134.1 |

FOREIGN PATENT DOCUMENTS

| | | |
|---|---|---|
| AU | 13320/99 | 4/1999 |
| DE | 19821060 | 4/1999 |
| EP | 0 984 023 | 3/2000 |
| EP | 1 125 585 | 8/2001 |
| JP | 5-72204 | 3/1993 |
| JP | 11-228442 | 8/1999 |
| JP | 2000-154151 | 6/2000 |
| WO | WO 95/33770 | 12/1995 |
| WO | WO 97/26912 | 7/1997 |
| WO | WO 98/11909 | 3/1998 |
| WO | WO 98/19706 | 5/1998 |
| WO | WO 98/30232 | 7/1998 |
| WO | WO 98/37415 | 8/1998 |
| WO | WO 98/38216 | 9/1998 |
| WO | WO 98/45331 | 10/1998 |
| WO | WO 98/52606 | 11/1998 |
| WO | WO 99/15553 | 4/1999 |
| WO | WO 00/19988 | 4/2000 |
| WO | WO 00/46240 | 8/2000 |
| WO | WO 00/67788 | 11/2000 |
| WO | WO 01/08700 | 2/2001 |

(Continued)

OTHER PUBLICATIONS

Carlesso et al., "Depletion of inducible co-stimulator (ICOS) bearing T cells inhibits expansion of T follicular helper cells ($T_{FH}$) and prevents disease in a graft versus host mouse model of scleroderma" Poster Presentation, American College of Rheumatology, 2009 Annual Scientific Meeting, Oct. 19, 2009.

Carlesso et al., "Targeted depletion of inducible co-stimulator (ICOS) bearing T cells prevents disease in a graft versus host model of scleroderma" Poster Presentation, 9th International Conference on Systemic Lupus Erythematosus, Jun. 25, 2010.

Cook et al., "The human immunoglobulin $V_H$ repertoire," *Immunology Today* (1995) 16(5):237-42.

Faggioni et al., "Determination of the minimum anticipated biological level (MABEL) for an ADCC-enhanced inducible co-stimulator (ICOS) monoclonal antibody for the treatment of autoimmune diseases" Poster Presentation, Annual Congress of the European League Against Rheumatism, Jun. 2010.

(Continued)

*Primary Examiner* — Ilia Ouspenski

(74) *Attorney, Agent, or Firm* — Fish & Richardson P.C.

(57) ABSTRACT

An antibody against AILIM (alternatively called JTT-1 antigen, JTT-2 antigen, ICOS and 8F4) was found to have a significant therapeutic effect on arthrosis, for example, rheumatoid arthritis and osteoarthritis, graft versus host disease, graft immune rejection, inflammation (hepatitis and inflammatory bowel diseases), diseased condition accompanied by the excessive production of an antibody against a foreign antigen triggered by immunological sensitization by the antigen.

10 Claims, 59 Drawing Sheets

FOREIGN PATENT DOCUMENTS

| | | |
|---|---|---|
| WO | WO 01/12658 | 2/2001 |
| WO | WO 01/15732 | 3/2001 |
| WO | WO 01/18022 | 3/2001 |
| WO | WO 01/21796 | 3/2001 |
| WO | WO 01/32675 | 5/2001 |
| WO | WO 01/64704 | 9/2001 |
| WO | WO 01/87981 | 11/2001 |
| WO | WO 02/44364 | 6/2002 |
| WO | WO 02/070010 | 9/2002 |
| WO | WO 02/076504 | 10/2002 |

OTHER PUBLICATIONS

Ghosh et al. "Ulcerative colitis" (2000) BMJ. 320(7242):1119-23.
Hanauer et al. "Management of Crohn's disease in adults" (2001) Am J Gastroenterol. 96(3):635-43.
Koh et al., "A screening method of SH2 domain ligands and blockers using a solid phase binding" (1997) Cancer Lett. 120(1):1-7.
Mendez et al. "Functional transplant of megabase human immunoglobulin loci recapitulates human antibody response in mice" (1997) Nat Genet. 15(2):146-56.
Mittereder et al., "ICOS is critical for follicular helper T cells ($T_{FH}$)-mediated maintenance of germinal center B cells in non human primates" Poster Presentation, American College of Rheumatology, 2008 Annual Scientific Meeting, Oct. 28, 2008.
Mittereder, "ICOS is critical for T follicular helper cell-mediated maintenance of germinal center B cells in non-human primates" FASEB Summer Research Conference—Autoimmunity, Jul. 2, 2009.
Soderlind et al., "Domain libraries: Synthetic diversity for de novo design of antibody V-regions," Gene (1995) 160(2):269-72.
Takai et al. "Epitope analysis and primary structures of variable regions of anti-human FcepsilonRI monoclonal antibodies, and expression of the chimeric antibodies fused with human constant regions" Biosci Biotechnol Biochem. (2000) 64(9):1856-67.
Taylor et al. "Unraveling Functions of ICOS Bearing T Cells: New Insights about Treating Autoimmune Disorders" Poster Presentation, Keystone Symposia on Tolerance and Autoimmunity, Feb. 21-26, 2010.
van der Merwe et al., "CD80 (B7-1) binds both CD28 and CTLA-4 with a low affinity and very fast kinetics," *Journal of Experimental Medicine* (1997) 185(3):393-403.
Abbas, "T-cell stimulation: an abundance of B7s," Nat Med. 5(12):1345-6 (1999).
Aicher et al., "Characterization of Human Inducible Costimulator Ligand Expression and Function," J. Immunol., 164(9):4689-4696 (2000).
Attwood T., Science 2000, 290:471-473.
Bajorath "A molecular model of inducible costimulator protein and three-dimensional analysis of its relation to the CD28 family of T cell-specific costimulatory receptors," J. Mol. Model. 5:169-176 (1999).
Beier et al., "Induction, binding specificity and function of human ICOS," Eur. J. Immunol., 30(12):3707-3717 (2000).
Bensimon et al., "Human lupus anti-DNA autoantibodies undergo essentially primary V kappa gene rearrangements," EMBO J. 13(13):2951-62 (1994).
Brodie et al., "LICOS, a primordial costimulatory ligand?," Curr. Biol., 10(6):333-336 (2000).
Buonfiglio et al., "Characterization of a novel human surface molecule selectively expressed by mature thymocytes, activated T cells and subsets of T cell lymphomas," Eur. J. Immunol., 29(9)2863-2874 (1999).
Buonfiglio et al., "The T cell activation molecule H4 and the CD28-like molecule ICOS are identical," Eur. J. Immunol. 30(12):3463-3467 (2000).
Cameron "Recent advances in transgenic technology" Molecular Biotechnology 7:253-65 (1997).
Campbell et al., "Separable effector T cell populations specialized for B cell help or tissue inflammation," Nat Immunol. 2(9):876-81 (2001).
Chambers, "The expanding world of co-stimulation: the two-signal model revisited," Trends in Immunology, 22(4):217-223 (2001).

Chapoval et al., "B7-H3: a costimulatory molecule for T cell activation and IFN-gamma production," Nat Immunol. 2(3):269-74 (2001).
Cocks et al. "A novel receptor involved in T-cell activation," Nature, 376:260-263 (Jul. 20, 1995).
Coyle et al., "The CD28-Related Molecule ICOS is Required for Effective T Cell-Dependent Immune Responses," Immunity 13(1):95-105 (2000).
Dong et al,, "B7-H1, a third member of the B7 family, co-stimulates T-cell proliferation and interleukin-10 secretion," Nat. Med. 5(12):1365-9 (1999).
Dong et al., "Cutting Edge: Critical Role of Inducible Costimulator in Germinal Center Reactions," J. Immunol., 166(6):3659-3662 (2001).
Dong, "ICOS co-stimulatory receptor is essential for T-cell activation and function," Nature 409(6816):97-101 (2001).
Eljaschewitsch et al., "Identification of a novel activation antigen on human CD4+ T cells," Immunobiol., 194(1-3):27 (1995).
Fabris, C. et al., *"Relationship among Hepatic Inflammatory Changes, Circulating Levels of Cytokines, and Response to IFN-α in Chronic Hepatitis C,"* Journal of Interferon and Cytokine Research (1998), 18(9):705-709.
Goding, "Monoclonal Antibodies: Principles and Practice," $2^{nd}$ Edition, Academic Press, Orlando, Florida, Chapter 8, pp. 281-293 (1986).
Goni et al., "Structural and idiotypic characterization of the L chains of human IgM autoantibodies with different specificities," J. Immunol. 142(9):3158-63 (1989).
Gonzalo et al., "ICOS is critical for T helper cell-mediated lung mucosal inflammatory responses," Nat Immunol. 2(7):597-604 (2001).
Gonzalo et al., "The Related Molecules CD28 and Inducible Costimulator Deliver Both Unique and Complementary Signals Required for Optimal T Cell Activation," J. Immunol., 166(1):1-5 (2001).
Guo et al., "Stimulatory Effects of B7-Related Protein-1 on Cellular and Humoral Immune Responses in Mice," J. Immunol., 166(9):5578-5584 (2001).
Hanzawa et al., "Characteristics of a TTH1 antibody which blocks an unknown adhesion phenomenon," Proceedings of the Japanese Society for Immunology, vol. 24, Abstract No. W17-13 (1994) [Original Japanese and English Language Translation].
Harlow and Lane, "Antibodies: A Laboratory Manual," Cold Spring Harbor Laboratory, p. 285 (1988).
Heyeck et al. "Developmental regulation of a murine T-cell-specific tyrosine kinase gene, Tsk," Proc. Natl. Acad. Sci. USA, vol. 90, pp. 669-673 (1993).
Houdebine "Production of pharmaceutical proteins from transgenic animals" J. Biotechnol. 34:269-87 (1994).
Huang Z., Pharmacology and Therapeutics, 2000, 86:201-215.
Hutloff et al., "ICOS is an inducible T-cell co-stimulator structurally and functionally related to CD28," Nature, 397(6716):263-266 (1999).
Hutloff et al., "Identification and initial characterization of a novel T cell-specific cell surface activation antigen," Immunobiol., 197(2-4):172 (1997).
Ihara et al., "Association studies of CTLA-4, CD28, and ICOS gene polymorphisms with type 1 diabetes in the Japanese population," Immunogenetics 53(6):447-54 (2001).
Iiyama et al., "The role of inducible co-stimulator (ICOS)/B7-related protein-1 (B7RP-1) interaction in the functional development of Peyer's patches," Immunology Letters, In Press, Uncorrected Proof available online Apr. 11, 2003, http://www.sciencedirect.com/science/journal/01652478.
Ishikawa et al., "Prediction of the Coding Sequences of Unidentified Human Genes. X. The Complete Sequences of 100 New cDNA Clones from Brain Which Can Code for Large Proteins in vitro," DNA Research, 5:169-176 (1998).
Iwai et al. (2002) "Amelioration of Collagen-Induced Arthritis by Blockade of Inducible Costimulator-B7 Homologous Protein Costimulation," J. Immunol., 169(8):4332-39.
Kappel et al. "Regulating gene expression in transgenic animals" Current Opinion in Biotechnology 3:548-53 (1992).

Kopf et al., "Inducible Costimulator Protein (ICOS) Controls T Helper Cell Subset Polarization after Virus and Parasite Infection," J. Exp. Med., 192(1):53-61 (2000).

Kuchroo et al. "B7-1 and B7-2 costimulatory molecules activate differentially the Th1/Th2 developmental pathways: Application to autoimmune disease therapy," Cell, 80:707-718 (Mar. 10, 1995).

Lamhemedi-Cherradi et al., "Further mapping of the Idd5.1 locus for autoimmune diabetes in NOD mice," Diabetes 50(12):2874-8 (2001).

Ling et al., "Assembly and annotation of human chromosome 2q33 sequence containing the CD28, CTLA4, and ICOS gene cluster: analysis by computational, comparative, and microarray approaches," Genomics 78(3):155-68 (2001).

Ling et al., "Cutting Edge: Identification of GL50, a Novel B7-Like Protein That Functionally Binds to ICOS Receptor," J. Immunol., 164(4):1653-1657 (2000).

Ling et al., "Differential expression of inducible costimulator-ligand splice variants: lymphoid regulation of mouse GL50-B and human GL50 molecules," J Immunol. 166(12):7300-8 (2001).

Linsley, "T cell activation: you can't get good help," Nat Immunol. 2(2):139-40 (2001).

Liu et al. "B7H costimulates clonal expansion of, and cognate destruction of tumor cells by, CD8(+) T lymphocytes in vivo," J Exp Med. 194(9):1339-48 (2001).

Lucia et al., "Expression of the novel T cell activation molecule hpH4 in HIV-infected patients: Correlation with disease status", AIDS Research and Human Retroviruses 16(6):549-557 (2000).

Mackay et al., "Follicular homing T helper (Th) cells and the Th1/Th2 paradigm," J Exp Med. 192(11):F31-4 (2000).

Mages et al., "Molecular cloning and characterization of murine ICOS and identification of B7h as ICOS ligand," Eur. J. Immunol., 30(4):1040-1047 (2000).

Marguet et al. "cDNA Cloning for Mouse Thymocyte-activating Molecule," The Journal of Biological Chemistry, vol. 267, No. 4, pp. 2200-2208 (1992).

McAdam et al., "Mouse inducible costimulatory (ICOS) molecule expression is increased by CD28 costimulation and regulates development of Th2 cells," FASEB Journal, 14(6):A1169 (2000).

McAdam, "ICOS is critical for CD40-mediated antibody class switching," Nature 409(6816):102-105 (2001).

McAdam, "Mouse Inducible Costimulatory Molecule (ICOS) Expression is Enhanced by CD28 Costimulation and Regulates Differentiation of CD4+ T Cells," J. Immunol., 165(9):5035-5040 (2000).

Metzler et al., Nature Structural Biol. 1997, 4:527-531.

Mueller, "T cells: A proliferation of costimulatory molecules," Curr. Biol. 10(6):R227-R230 (2000).

Mullins et al. "Expression of the DBA/2J Ren-2 gene in the adrenal gland of transgenic mice" EMBO J., 8:4065-72 (1989).

Mullins et al. "Fulminant hypertension in transgenic rats harbouring the mouse Ren-2 gene" Nature, 344:541-44 (1990).

Mullins et al. "Transgenesis in nonmurine species" Hypertension 22:630-33 (1993).

Nanji, S.A. et al., "*Combination therapy With Anti-ICOS and Cyclosporine Enhances Cardiac but Not Islet Allograft Survival*," Transplantation Proceedings (2003), 35(7):2477-2478.

Niemann "Transgenic farm animals get off the ground" Transgenic Research, 7:73-75 (1998).

Nojima et al. "The 4F9 antigen is a member of the tetra spans transmembrane protein family and functions as an accessory molecule in T cell activation and adhesion," Cellular Immunology, 152:249-260 (1993).

Nurieva et al., "Inducible costimulator is essential for collagen-induced arthritis," J. Clin. Invest. 111(5):701-06 (2003).

O'Neill, "Co-stimulating allergy," Trends Immunol. 22(4):183 (2001).

Ogawa et al., "Opposing effects of anti-activation-inducible lymphocyte-immunomodulatory molecule/inducible costimulator antibody on the development of acute versus chronic graft-versus-host disease," J Immunol. 167(10):5741-8 (2001).

Overbeek "Factors affecting transgenic animal production," Transgenic Animal Technology, A Laboratory Handbook 96-98 (1994).

Özkaynak et al., "Importance of ICOS-B7RP-1 costimulation in acute and chronic allograft rejection," Nature Immunology 2(7):591-596 (2001).

Pech et al., "A large section of the gene locus encoding hum immunoglobulin variable regions of the kappa type is duplicated," J. Mol Biol. 183(3):291-9 (1985).

Poster, Kyoto International Conference Hall, Takaragaike Sakyo-ku, Kyoto, Japan (Nov. 30, 1994) [Original Japanese and English Language Translation].

Pound, "A new T-helper cell subset?" Trends Immunol. 22(4):182-3 (2001).

Redoglia et al., "Characterization of H4: a mouse T lymphocyte activation molecule functionally associated with the CD3/T cell receptor," Eur. J. Immunol., 26(11):2781-2789 (1996).

Richter et al., "Tumor necrosis factor-$\alpha$ regulates the epxpression of inducible costimulator receptor ligand on CD34+ progenitor cells during differentiation into antigen presenting cells," J. of Biological Chem. 276(49):45686-45693 (2001).

Riley et al., "ICOS Costimulation Requires IL-2 and Can Be Presented by CTLA-4 Engagement," J. Immunol., 166(8):4943-4948 (2001).

Robert et al. "Antibody Cross-Linking of the Thymocyte-Specific Cell Surface Molecule CTX Causes Abnormal Mitosis and Multinucleation of Tumor Cells," Experimental Cell Research, vol. 235, pp. 227-237 (1997).

Rottman et al., "The costimulatory molecule ICOS plays an important role in the immunopathogenesis of EAE," Nat Immunol. 2(7):605-11 (2001).

Sakamoto et al., "AILIM/ICOS: its expression and functional analysis with monoclonal antibodies," Hybridoma and Hybridomics, 20(5):293-303 (2001).

Sato et al. (2000) "Up-regulation of inducible co-stimulator (ICOS) expression and its regulation of cytokine production in inflammatory bowel disease," Gastroenterology, 118(4):A662.

Schwartz, "Immunology. It takes more than two to tango," Nature 409(6816):31-2 (2001).

Sharpe "Analysis of lymphocyte costimulation in vivo using transgenic and 'knockout' mice," Current Opinion in Immunology, 7:389-395 (1995).

Sigmund "Are studies in genetically altered mice out of control?" Arterioscler. Thromb. Vasc. Biol., 20:1425-29 (2000).

Skolnick et al., Trends in Biotech. 2000, 18(1):34-39.

Sperling et al., "ICOS costimulation: It's not just for TH2 cells anymore," Nat Immunol. 2(7):573-4 (2001).

Sperling, "ICOS costimulation: is it the key to selective immunotherapy?," Clin Immunol. 100(3):261-2 (2001).

Sporici et al., "Costimulation of memory T-cells by ICOS: a potential therapeutic target for autoimmunity?" Clin Immunol. 100(3):263-9 (2001).

Sporici et al., "ICOS ligand costimulation is required for T-cell encephalitogenicity," Clin Immunol. 100(3):277-88 (2001).

Swallow et al., "B7h, a Novel Costimulatory Homolog of B7.1 and B7.2, is Induced by TNF$\alpha$," Immunity, 11(4):423-432 (1999).

Tafuri et al., "ICOS is essential for effective T-helper-cell responses," Nature 409(6816):105-109 (2001).

Tai et al. "A role for CD9 molecules in T cell activation," J. Exp. Med., 184:753-758 (Aug. 1996).

Tamatani et al., "AILIM/ICOS: a novel lymphocyte adhesion molecule," International Immunology, 12(1):51-55 (2000).

Tamatani et al., "Characteristics of an antibody which induces an ICAM-1-LFA-1-independent adhesion pathway," Proceedings of the Japanese Society for Immunology, vol. 23, Abstract No. H-160 (1993) [Original Japanese and English Language Translation].

Tamura et al., "B7-H1 costimulation preferentially enhances CD28-independent T-helper cell function," Blood 97(6):1809-16 (2001).

Tesciuba et al., "Inducible costimulator regulates Th2-mediated inflammation, but not Th2 differentiation, in a model of allergic airway disease," J Immunol. 167(4):1996-2003 (2001).

Tezuka et al. "Identification and characterization of rat AILIM/ICOS, a novel T-cell costimulatory molecule, related to the CD28/CTLA4 family," Biochemical and Biophysical Research Communications, 276:335-345 (2000).

Tezuka et al., "Genetic cloning of a lymphocyte surface signal transduction molecule which induces an unknown adhesion phenomenon," Proceedings of the Japanese Society for Immunology, vol. 24, Abstract No. W17-14 (1994) [Original Japanese and English Language Translation].

Tomlinson et al., "The repertoire of human germline VH sequences reveals about fifty groups of VH segments with different hypervariable loops," J. Mol. Biol. 227(3):776-98 (1992).

Wall "Transgenic livestock: progress and prospects for the future" Theriogenology 45:57-68 (1996).

Wallin et al., "Enhancement of CD8+ T cell responses by ICOS/B7h costimulation," J Immunol. 167(1):132-9 (2001).

Wang et al., "Costimulation of T cells by B7-H2, a B7-like molecule that binds ICOS," Blood, 96(8):2808-2813 (2000).

Yoshinaga et al., "Characterization of a new human B7-related protein: B7RP-1 is the ligand to the co-stimulatory protein ICOS," International Immunology, 12(10):1439-1441 (2000).

Yoshinaga et al., "T-cell co-stimulation through B7RP-1 and ICOS," Nature, 402(6763:827-832 (1999).

* cited by examiner

| LINE | SPECIFICITY | LYMPHOKINE | Th1/Th2 | CD28/AILIM |
|---|---|---|---|---|
| 1. T CELL STRAIN | | | | |
| D10 | CON-ALBUMIN | IL-4 | Th2 | +/+ |
| MS202 | I-A^k | IL-4 | Th2 | +/+ |
| CD28KO | I-E^k | IL-4 | Th2 | -/+ |
| EL-4 | ? | IL-4/-2 | Th0 | +/+ |
| 21.2 | CYTOCHROME C | IL-2/IFN-r | Th1 | +/- |
| BC3C13 | Mls^c | IFN-r | Th1 | +/- |
| 2. THYBRIDOMA (BW5147 PARENTAL STRAIN) | | | | |
| KV24 | ? | IL-2 | Th1 | +/- |
| DO.11.10 | OVA | IL-2 | Th1 | +/- |
| 8-4-31 | SEB | IL-2 | Th1 | +/- |
| 3H10-11 | SEB | IL-2 | Th1 | +/- |
| 61-21-25 | SEB | IL-2 | Th1 | +/- |
| 1-2-66 | SEB | IL-2 | Th1 | +/- |
| 6-13-64 | SEB | IL-2 | Th1 | -/- |

FIG. 7

SEQUENCE LISTING

```
<160> NUMBER OF SEQ ID NOS: 3

<210> SEQ ID NO 1
<211> LENGTH: 6
<212> TYPE: PRT
<213> ORGANISM: Homo sapiens

<400> SEQUENCE: 1

Met Tyr Pro Pro Pro Tyr
1               5

<210> SEQ ID NO 2
<211> LENGTH: 4
<212> TYPE: PRT
<213> ORGANISM: Homo sapiens

<400> SEQUENCE: 2

Tyr Met Asn Met
1

<210> SEQ ID NO 3
<211> LENGTH: 4
<212> TYPE: PRT
<213> ORGANISM: Homo sapiens

<400> SEQUENCE: 3

Tyr Val Lys Met
1
```

PHARMACEUTICAL COMPOSITION FOR TREATING IMMUNE DISEASES

CROSS REFERENCE TO RELATED APPLICATIONS

This application is a continuation of U.S. application Ser. No. 10/729,880, filed Dec. 5, 2003, which is a continuation of U.S. application Ser. No. 09/830,548, filed Jun. 12, 2001, now abandoned, which is a national phase filing under 35 U.S.C. §371 of international application number PCT/JP00/05868, filed Aug. 30, 2000, which claims priority to Japanese Application Serial No. 2000/254680, filed Aug. 24, 2000, and Japanese Application Serial No. 11/242672, filed Aug. 30, 1999. The disclosures of the prior applications are considered part of (and are incorporated by reference in) the disclosure of this application.

TECHNICAL FIELD

The present invention relates to a pharmaceutical composition comprising a substance having an activity which modulates biological activity of AILIM (activation inducible lymphocyte immunomodulatory molecule; alternatively called "JTT-1 antigen", "JTT-2 antigen", "ICOS (inducible costimulator" or "8F4"), especially a signal transduction mediated by the AILIM.

Specifically, the present invention relates to a pharmaceutical composition comprising a substance having an activity which modulates (for example, inhibits) proliferation of AILIM-expressing cells or modulates (for example, inhibits) production of a cytokine (for example, interferon γ, or interleukin 4) by AILIM-expressing cells.

More specifically the present invention relates to (1) a pharmaceutical composition for preventing, treating, or prophylaxis of arthrosis (for example, rheumatoid arthritis; RA, osteoarthritis: OA), (2) a pharmaceutical composition for preventing, treating, or prophylaxis of inflammation (for example, hepatitis), (3) a pharmaceutical composition for preventing, treating, or prophylaxis of graft versus host reaction (GVH reaction), graft versus host disease (GVHD), or immune rejection accompanying transplantation of a tissue or organ, (4) a pharmaceutical composition for preventing or prophylaxis of immune response triggered by an foreign antigen or autoantigen (for example, the production of an antibody against the antigen, cell proliferation, production of a cytokine).

BACKGROUND ART

A living body of mammals has immune response systems that excludes pathogenic microorganisms (viruses, bacteria, parasites, etc.) or foreign bodies (both are called "antigen" in the following) that have invaded the living body. One of them is called natural immune response system, another acquired immune response system. The former is an exclusion mechanism comprising phagocytosis by phagocytes (polymorphonuclear leukocytes, monocytes, macrophages, etc.), attack by natural killer (NK) cells, and non-specific recognition such as opsonization of antigen by complements. The latter, acquired immune response system, is an exclusion mechanism by lymphocytes (mainly, T cells and B cells) that acquired the specificity to the antigen (namely, activated lymphocytes). B cells that acquired antigen specificity attack the antigen existing outside of the cells through production of antibodies specific to the antigen. T cells that acquired antigen specificity (namely, activated T cells) are classified into helper T cells and cytotoxic T cells (cytotoxic lymphocyte, CTL). The helper T cells regulate a differentiation of B cells and a production of antibodies, and destroy the antigen cooperating with phagocytes. The latter, CTLs attack virus-infected cells and so on by themselves (Experimental Medicine: SUPPLEMENT, "Bio Science Term Library, Immunity", Yodosha, pp. 14-17 (1995)).

This acquisition of antigen specificity by T cells (namely, activation of T cells) is initiated through recognition by T cells the antigen presented by antigen-presenting cells (APC) such as macrophage, B cells, or dendritic cells. Antigen-presenting cells process the antigens so incorporated and present these processed antigens through binding them to major histocompatibility complex (MHC). T cells receive primary signal for activation of the cells (or acquisition of specificity) by recognizing the processed antigens presented by antigen-presenting cells through a complex between T cell receptor (TcR) and CD3 antigen existing on the surface of the cell membrane (TcR/CD3 complex).

However, the TcR/CD3 complex-mediated primary signal alone cannot activate T cells sufficiently and leads to unresponsiveness or clonal anergy, so that the cells can not react with any stimulation received thereafter. The autocrine of interleukin 2 (IL-2) is necessary for T cells to be activated, to be differentiated into antigen specific T cell clones, and to be proliferated. In clonal anergy, T cells are inactivated due to no production of IL-2 and such and no cell division. Namely, the activation of T cells accompanied by production of cytokines such as IL-2 requires the secondary signal following the first signal through TcR/CD3 complex. This secondary signal is called costimulatory signal.

T cells receive this secondary signal and transmit it into the cells by interacting (cell adhesion) with molecules other than MHC on antigen-presenting cells through molecules other than TcR/CD3 complex on the T cell surface. This secondary signal avoids cell anergy (clonal anergy) and activates the cells.

Although some part of the mechanism of the secondary signal transmission between antigen-presenting cells and lymphocytes such as T cells have not yet been elucidated in detail, studies so far have revealed that an important factor for the secondary signal transmission is the interaction of CD28 (also named Tp44, T44, or 9.3 antigen), which is a cell surface molecule expressed mainly on T cells and thymus cells, with CD80 (also named B7-1, B7, BB1, or B7/BB1), which is a cell surface molecule expressed on antigen-presenting cells (macrophages, monocytes, dendritic cells, etc.) and with CD86 (also named B7-2 or B70), which is also a cell surface molecule on antigen-presenting cells (namely, cell adhesion through the binding between these molecules). Moreover, it has been experimentally elucidated that the interaction of Cytolytic T lymphocyte associated antigen 4 (CTLA-4), whose expression is thought to be enhanced depending on the secondary signal, with the CD80 (B7-1) and CD86 (B7-2) (namely, cell adhesion through the binding between these molecules) also plays an important role in the regulation of T cell activation by the secondary signal. In other words, the regulation of T cell activation by the transmission of the secondary signal involves at least the interaction between CD28 and CD80/CD86, the enhancement of CTLA-4 expression, which is thought to depend on the interaction, and the interaction between CTLA-4 and CD80/CD86.

CD28 is known to be a costimulator molecule transmitting the secondary signal (costimulatory signal) required for the activation of T cells and for the avoidance of anergy. The secondary signal transmitted by binding this molecule to costimulator molecules, CD80 (B7-1) and CD86 (B7-2), on antigen-presenting cells (cell adhesion through the binding between these molecules), stabilizes mRNA of Th1-type cytokines and consequently promotes production by T cells of a large amount of Th1-type cytokines such as IL-2, IFNγ, and TNFα. The expression of CTLA-4 is induced by the primary signal transmitted through TcR/CD3, and the expression is also enhanced by the secondary signal transmitted by the binding between CD28 and CD80. It is being revealed that CTLA-4 receives these signals to work to inhibit T cell function, which is contrary to the activation of T cells by the secondary signal transmitted by CD28.

Human CD28 and CTLA-4 are type I glycoproteins whose molecular weights are 44 kD and 41 to 43 kD, respectively. Both have an immunoglobulin-like domain, belong to the immunoglobulin superfamily, and have both function as a cell adhesion molecule and function as a signal transmission molecule.

Human CD28 forms a homodimer with a disulfide bond while CTLA-4 exists as a monomer. Both CD28 and CTLA-4 genes are located at "2q33" on human chromosome and "1C" on mouse chromosome, and are composed of four (4) exons. Human CD28 and CTLA-4 are composed of 220 and 223 amino acids, respectively, including the leader sequences, and amino acid homology between them is 20 to 30%.

The ligands for CD28 and CTLA-4 are CD80 (B7-1) and CD86 (B7-2) in human and mice. CTLA-4 has about 20 times as high affinity to both ligands as CD28. It has been elucidated that the amino acid sequence structures "MYPPPY (Met-Tyr-Pro-Pro-Pro-Tyr)" conserved through animal species is important for the binding of CD28 and CTLA-4 to CD80 (B7-1). It has also been reported that, when CD28 is stimulated, PI3 kinase (phosphoinositide 3 kinase, PI3K) associates with the phosphorylated tyrosine residue in a partial sequence "YMNM (Tyr-Met-Asn-Met)" of CD28 and that CD28 plays an important role in intracellular signal transmission through this "YxxM" structure. Furthermore, it has been reported that CTLA-4 also has a sequence represented by "YxxM," namely "YVKM (Tyr-Val-Lys-Met)" in its cytoplasmic region and that, after being stimulated, SYP associates with this sequence.

CD28 is expressed specifically in thymocytes and peripheral blood T cells, and CTLA-4 is expressed specifically in activated T cells (Cell Engineering: SUPPLEMENT, "Handbook of Adhesion Molecule", Shujunsha, pp. 93-102 (1994); ibid. pp. 120-136; Experimental Medicine: SUPPLEMENT, "BIO SCIENCE Term Library, Immunity", Yodosha, pp. 94-98 (1995); Experimental Medicine: SUPPLEMENT, "BIOSCIENCE Term Library, Intracellular Signal Transduction", Yodosha, pp. 58-59 (1997); Nihon Rinsho, Vol. 55, No. 6, pp. 215-220 (1997)).

In the regulation of T cell function (the activation and the inhibition of function of T cells), the importance of interactions among multiple molecules such as costimulator molecules (CD28, CD80 (B7-1), CD86 (B7-2), etc.) and CTLA-4, which cooperates with them, (in other words, cell adhesion through the binding between these molecules) has thus been recognized, and this has been drawn attention to the relationship between these molecules and diseases, and the treatment of diseases by regulating the function of these molecules.

As described above, although a living body activates its acquired immune response system against antigens that are foreign bodies to the living body (self), it also has immunological tolerance so as to show no immune response against its own component (autoantigen). If immunological tolerance breaks down by some reason, immune response to the autoantigen occurs, autoantigen-reactive T cells are induced by the same mechanism as mentioned above to fall into abnormal state of immunity, and various autoimmune diseases are caused.

In other words, since non-stimulated antigen presenting cells (APC) in normal tissues do not express costimulatory molecules when the immune system of a living body is normal, T cells are in the unresponsiveness state to maintain immunological tolerance even if autoantigen-reactive T cells, which reacts with autoantigen, exist. It has been suggested that in abnormal state of immunity, more autoantigen-reactive T cells are activated due to abnormal excess and continuous expression of costimulatory molecules to thereby cause autoimmune diseases.

From such viewpoints recently, many attempts to treat various autoimmune diseases by modulating the transmission of costimulatory signals, for example, the above-mentioned signal transmission between CD28/CTLA-4 and CD80/CD86, are proposed.

The results of such attempts have not yet clarified in detail the mechanism of the T cell activation by interaction between costimulatory molecules and the related molecules (in other words, cell adhesion through the binding between these molecules). Other unknown molecules may be involved in this mechanism.

Recently, the present inventors have successfully identified and isolated a novel cell membrane surface molecule derived from mammals (human, mouse and rat) considered as a molecule which transmits the secondary signal (a costimulatory signal) necessary for the activation of lymphocytes, for example T cells, and controls the function of the activated lymphocytes, for example, activated T cells, by working with the signal, in the same manner as in the above "CD28" and "CTLA-4" and designated the molecule "JTT-1 antigen" or "JTT-2" (Unexamined Published Japanese Patent Application (JP-A) No. Hei 11-29599; WO98/38216; Int. Immunology, Vol. 12, No. 1, pp. 51-55, 2000). The present inventors later change the name of these molecules to AILIM (activation inducible lymphocytes immunomodulatory molecule).

From the studies by the present inventors, the following knowledge has been acquired about this novel molecule AILIM.

(1) AILIM has the following similarity with "CD 28", a cell surface molecule of a lymphocyte, for example, T cells, which transmits a costimulatory signal important for the activation of T cells, mediated by intercellular adhesion, and with "CTLA-4", a cell surface molecule of a lymphocyte, for example, T cells, which controls the function of activated lymphocytes, such as activated T-cells, working with the signal.

1. 20 or more amino acid residues including cysteine residues are highly conserved.

2. Proline repeating sequence "Pro-Pro-Pro (PPP)" essential as the ligand binding region, is conserved in the extracellular region.

3. A sequence "Tyr-Xaa-Xaa-Met (YxxM)" (Xaa and x represents any amino acid) sequence essential as the signal transmitting region is conserved in the cytoplasmic region.

4. A location of the gene encoding "mouse AILIM (mouse JTT-1 antigen)" on the mouse chromosomes is "1C3", same as those for mouse "CD28" and "CTLA-4".

(2) In the same manner as in "CD28" and "CTLA-4" having the function mediating intercellular adhesion, "AILIM (JTT-1 antigen)" has the ability of mediating cellular adhesion between thymus cells and lymphoblast cells and thymoma cells stimulated by mitogen, for example, ConA.

(3) AILIM is strongly expressed at least in thymus cells, lymphoblast cells stimulated by mitogen such as ConA (activated T-lymphoblast cells, and activated B-lymphoblast cells), peripheral blood lymphocytes, and thymoma cells.

(4) An antibody against AILIM (JTT-1 antigen) significantly proliferates human peripheral blood lymphocytes and higher proliferation is induced by co-existing with a monoclonal antibody against CD3 constituting TcR/CD3 complex on T cells which receives the first signal from antigen-presenting cells essential for the activation of T cells.

(5) The condition of experimental allergic encephalomyelitis (EAE) is alleviated by administering an antibody against AILIM (JTT-1 antigen).

(6) By the administering an antibody against AILIM (JTT-1 antigen) a glomerular basement membrane (GMB) nephritis model rat, the condition is alleviated.

After the report of the identification and characterization analysis of AILIM by the present inventors, the group of Kroczek et al. has reported the identification of a molecule named ICOS (inducible costimulator) or 8F4, an identical molecule to AILIM derived from human, or the molecule designated 8F4 (Nature, Vol. 397, pp. 263-266, 1999; WO99/15553).

Only the above has been reported about AILIM (alternatively called: JTT-1 antigen, JTT-2 antigen, ICOS, or 8F4), and its biological functions and relationship with diseases have not been revealed in details yet.

On the other hand, novel molecules celled B7h, B7RP-1, GL50 or LICOS which are considered as a ligand interacting with this costimulatory transmission molecule AILIM have been identified very recently (Nature. Vol. 402, No. 6763, pp. 827-832, 1999; Nature Medicine, Vol. 5, No. 12, pp. 1365-1369, 1999; J. Immunology, Vol. 164, pp. 1653-1657, 2000; Curr. Biol., Vol. 10, No. 6, pp. 333-336, 2000).

The identification of these two kinds of novel molecules, namely AILIM (ICOS) and B7RP-1 (B7h, GL50, LICOS), as the signal transduction pathway for the costimulatory signal essential for the above activation of lymphocytes such as T cells, and the control of the function of activated T cells, revealed that there is the novel third pathway by the interaction between AILIM (ICOS) and B7RP-1 (B7h, GL50, LICOS), besides the known first and second signal pathways which are already known transduction pathway between CD28 and CD80 (B7-1)/CD86 (B7-2) and that between CTLA4 and CD80 (B7-1)/CD 86 (B7-2).

Studies on the biological functions of these novel molecules, the function control of lymphocytes, such as T cells, through this third costimulatory signal transduction by the molecules, and the relationship between the novel signal transduction and diseases are in progress.

DISCLOSURE OF THE INVENTION

Specifically, an objective of the present invention is to reveal biological functions of the novel molecule AILIM, considered, like "CD28" and "CTLA-4", as a molecule which transmits the secondary signal (costimulatory signal) essential for the activation of lymphocytes, such as T cells, and which controls the functions of activated lymphocytes, such as activated T cells, by working with the signal; to reveal relationships between the expression of AILIM and diseases; and to provide a method and a pharmaceutical which inhibit the development of the various diseases dependent on the expression pattern of AILIM or which treat the diseases by controlling the biological functions of the AILIM using the medical and pharmaceutical methods (for example, a drug such as a low molecular compound and an antibody).

The present inventors have studied the biological functions of mammalian AILIM, the expression pattern for AILIM in various cells, the relationships between the expression of AILIM and diseases to find the following knowledge in addition to the above knowledge obtained so far, completing the present invention.

(I) In T cells of the thymus, one of the lymphoid tissues in a normal mouse, strong expression of the AILIM was observed in the same way as in the cells which strongly expresses CD3, confirming the correlation between both expressions. In contrast, the expression of CD28, a costimulatory molecule, decreased as the expression of CD3 increased. In mouse normal thymus derived T cells, expressions of AILIM and CD28 showed adverse moving states. In CD4-negative CD8-negative T cells, the expression of neither AILIM nor CD28 was observed. In T cells derived from normal mouse thymus, the expression of CD28 is the highest in CD4-positive CD8-positive T cells, and the expression in CD4-negative CD8-positive T cells, or CD4-positive CD8-negative cells which experienced the following cellular differentiation was lowered. In contrast, in normal mouse thymus cells, the expression of AILIM was only slightly detected in CD4-positive CD8-positive T cells, but, the high expression was found in CD4-negative CD8-positive T cells, or CD4-positive CD8-negative T cells which experienced the following cellular differentiation. The expression of AILIM in normal mouse thymus T cells differs from that of CD28 in the relationship not only with CD3 expression, but also with those of CD4 and CD8.

(II) The expression of AILIM in T cells in spleen and lymph nodes which are ones of the normal mouse lymphoid tissues is little in comparison with the expression in the mouse thymus derived T cells, and the expression of AILIM is found in a very small number of CD4-positive T cells (about 1 to 3 percent of CD4-positive T cells.

(III) The obvious expression of AILIM is observed in T cells (mononuclear cells) derived from liver tissues in the mouse hepatitis model induced by administering P. acnes (Propionibacterium acnes) and LPS (Lipopolysaccaride). The expression is extremely higher in comparison with CD4-positive cells derived from normal mouse spleen or T cells derived from lymph node.

(IV) In peripheral blood derived cells from a normal healthy person, most of AILIM-positive cells are CD4-positive CD8-negative cells, and most AILIM-positive cells are T cells. In the B cells derived from peripheral blood of a normal healthy person, the expression of AILIM is also slightly observed.

(V) In joint tissue infiltrating T cells in synovial fluid from a rheumatoid arthritis (RA) patient (CD4-positive T cells, and CD4-negative cells), the expression of AILIM is found to be significantly higher in comparison with T cells in peripheral blood from the same patient and T cells in the peripheral blood from a normal healthy person.

(VI) In CD4-positive T cells in synovial fluid from an osteoarthritis (OA) patient, the ratio of AILIM-positive cells is significantly increased. The ratio of AILIM-positive cells is also significantly increased in CD4-positive T cells from a progressive systemic sclerosis (PSS) patient.

(VII) The increased expression of AILIM is observed in the T cells derived from mouse lymphoid tissues 3 to 6 hours after stimulation using Ionophore with anti-CD3 antibody, Concanavalin A (ConA), or PMA (phorbol myristate acetate), and the maximum expression of AILIM is confirmed about 12 hours after the stimulation. The high expression of AILIM is confirmed 24 hours or longer after the stimulation, and the expression is maintained at the same level even about 48 hours after the stimulation.
(VIII) By activating human peripheral blood T cells (CD4-positive cells and CD8-positive T cells) with PMA and Ionophore, AILIM is highly expressed about 8 hours after the stimulation. In human peripheral blood cells, the high expression of AILIM is also induced by the stimulation with either of anti-CD3 antibody and anti-AILIM antibody, or anti-CD3 antibody and anti-CD28 antibody.
(IX) Constitutive expression of AILIM is observed in the T-cell lines which have the property of Th2 type cytokine production (for example, DC10, MS202, CD28KO, EL-4). AILIM expression in these cell lines is as high as or higher than the expression of CD28.
(X) When T cells derived from spleen or thymus in a normal mouse or rat or T cells derived from peripheral blood in a normal healthy person are cultured on a plate coated with both anti-AILIM antibody and anti-CD3 antibody constituting the present invention, production of a cytokine (IFNγ, IL-4, TNFα, IL-2, IL-10) from the T cells, and proliferation of T cells are induced.
(XI) When T cells derived from peripheral blood, stimulated by ConA or PMA, are cultured on a plate coated with both anti-AILIM antibody and anti-CD3 antibody constituting the present invention, production of a cytokine from the T cells, and cell proliferation are induced. This result is the same level as the case of culturing T cells derived from peripheral blood, stimulated by ConA or PMA, in the plate coated with both anti-CD28 and anti-CD3 antibody.
(XII) When anti-AILIM antibody constituting the present invention is added to the T cells in which T-cell response was triggered by culturing thymus cells and spleen cells isolated from each normal spleen and normal thymus (adhesive cells are removed from each) in the plate coated with anti-CD3 antibody, production of a cytokine [for example, interferon γ (IFN-γ), interleukin 4 (IL-4)] from the T cells is inhibited and the proliferation of the T cells is inhibited. Moreover, the inhibition of T-cell response by the anti-AILIM antibody (for example, the above cytokine production, cell proliferation) is dependent on the concentration of the antibody. In contrast, when anti-CD28 antibody is added instead of anti-AILIM antibody, the T-cell response is enhanced, differently from the result of using anti-AILIM antibody.
(XIII) When anti-AILIM antibody constituting the present invention is administered to a hepatitis model animal induced by administering *P. acnes* (*Propionibacterium acnes*) and LPS (lipopolysaccaride), the increase of IFN-γ in blood is significantly inhibited dependently on the concentration of the antibody, and the increase of GOP/GPT is significantly inhibited.
(XIV) When anti-AILIM antibody constituting the present invention is administered to an arthritis model animal induced by administering dead tubercule *bacillus*, paw swelling is significantly inhibited dependently on the concentration of the antibody, and the increase of various parameters in arthritis is significantly inhibited.
(XV) When anti-AILIM antibody constituting the present invention is administered to a graft versus host disease (GVHD) model animal, the production of IgG and IgE which are the products of graft versus host reaction (GVH reaction) is significantly inhibited, and the increased production of anti-dsDNA antibody, an index for autoantibody valence, is significantly inhibited.
(XVI) When anti-AILIM antibody constituting the present invention is administered to a model animal in which production of an antibody against excessive foreign antigens, induced by sensitizing sheep red blood cells (SRBC) as a foreign antigen (immediately or several days after the sensitization), the increase of the production of an antibody against the SRBC, a foreign antigen, is significantly inhibited. The inhibitory effect is higher than that in the case of administering CTLA4-Ig.
(XVII) When anti-AILIM antibody constituting the present invention is administered to a model animal in which production of an antibody against excessive foreign antigens induced by sensitizing NP-KLH, as a foreign antigen is triggered (immediately or several days after the sensitization), the increase of the production of an antibody against the NP-KLH, a foreign antigen, is significantly inhibited
(XVIII) Anti-AILIM antibody significantly inhibits cellular proliferation of T cells in allogenic mixed lymphocyte reaction (MLR) with peripheral blood monocytes (PBMC) and T cells derived from different normal donors.

A pharmaceutical composition of the present invention is useful as a pharmaceutical for modulating various reactions in vivo in which transduction of a costimulatory signal to AILIM-expressing cells mediated by AILIM is involved (for example, cell proliferation of AILIM-expressing cells, production of cytokine (s) by AILIM-expressing cells, immune cytolysis or apoptosis of AILIM-expressing cells, and an activity in inducing antibody-dependent cellular cytotoxicity against AILIM-expressing cells) and/or as a pharmaceutical for preventing sideration and/or progression of various diseases in which the signal transduction mediated by AILIM is involved and treating or prophylaxis of the diseases.

Specifically, a pharmaceutical composition of the present invention can modulate the proliferation of AILIM-expressing cells (inhibition or promotion), or can modulate (inhibition or promotion) production of cytokines by AILIM-expressing cells (for example, interferon γ, or interleukin 4), and can prevent various diseased condition triggered by various physiological phenomena in which signal transduction mediated by AILIM is involved, and may treat or prevent the various diseases.

By using the pharmaceutical composition of the present invention, for example arthrosis (for example rheumatoid arthritis; RA, osteoarthritis: OA), inflammation (for example, hepatitis), graft versus host reaction (GVH), graft versus host disease (GVHD), immune rejection response accompanying transplantation of tissues or organ, immune response triggered by a foreign antigen or an autoantigen (for example, the production of antibody against the antigen, cell proliferation, production of cytokine (s)) can be inhibited, prevented and/or treated.

In addition, the pharmaceutical composition of the present invention can be applied for treating or prophylaxis of an arbitrary inflammation to which various steroids are applied as an anti-inflammatory.

Moreover, the pharmaceutical composition of the present invention can be applied for treating or preventing, inflammatory diseases, for example, inflammation accompanying various arthritis (for example, rheumatoid arthritis, osteoarthritis), pneumonia, hepatitis (including viral hepatitis), inflammation accompanying infectious diseases, inflammatory bowel diseases, intestinal enteritis, nephritis (inflammation accompanying glomerular nephritis, nephrofibrosis), gastritis, angiitis, pancreatitis, peritonitis, bronchitis, myocarditis, cerebritis, inflammation in postischemic reperfusion injury (myocardial ischemic reperfusion injury), inflammation attributed to immune rejection after transplantation of tissue and organ, burn, various skin inflammation (psoriasis, allergic contact-type dermatitis, lichen planus which is chronic inflammatory skin disease), inflammation in multiple organ failure, inflammation after operation of PTCA or PTCR, and inflammation accompanying arteriosclerosis, and autoimmune thyroiditis.

Specifically, the present invention is the invention described from the following (1) to (32).

(1) A pharmaceutical composition for preventing, treating, or prophylaxis of arthrosis, comprising a substance having an activity in modulating a signal transduction mediated by AILIM, and a pharmaceutically acceptable carrier.

(2) The pharmaceutical composition of (1), wherein the substance has an activity in inhibiting proliferation of AILIM-expressing cells or in inhibiting production of a cytokine by AILIM-expressing cells.

(3) The pharmaceutical composition of (1) or (2), wherein the cytokine is interferon γ which is a cytokine produced by Th1 type T cells, or interleukin 4 which is a cytokine produced by Th2 type T cells.

(4) The pharmaceutical composition of any one of (1) to (3), wherein the arthrosis is rheumatoid arthritis.

(5) The pharmaceutical composition of any one of (1) to (3), wherein the arthrosis is osteoarthritis.

(6) The pharmaceutical composition of any one of (1) to (5), wherein the substance is a protein substance.

(7) The pharmaceutical composition of (6), wherein the protein substance is selected from the group consisting of:
   a) an antibody which binds to AILIM or a portion thereof;
   b) a polypeptide comprising the whole or a portion of an extracellular region of AILIM;
   c) a fusion polypeptide comprising the whole or a portion of an extracellular region of AILIM and the whole or a portion of a constant region of immunoglobulin heavy chain; and
   d) a polypeptide which binds to AILIM.

(8) The pharmaceutical composition of any one of (1) to (5), wherein the substance is a non-protein substance.

(9) The pharmaceutical composition of (8), wherein the non-protein substance is DNA, RNA, or a chemically synthesized compound.

(10) A pharmaceutical composition for preventing, treating, or prophylaxis of inflammation, comprising a substance having an activity in modulating signal transduction mediated by AILIM, and a pharmaceutically acceptable carrier.

(11) The pharmaceutical composition of (10), wherein the substance has an activity in inhibiting proliferation of AILIM-expressing cells or in inhibiting production of a cytokine by AILIM-expressing cells.

(12) The pharmaceutical composition of (11), wherein the cytokine is interferon γ which is a cytokine produced by Th1 type T cells, or interleukin 4 which is a cytokine produced by Th2 type T cells.

(13) The pharmaceutical composition of any one of (10) to (12), wherein the inflammation is hepatitis.

(14) The pharmaceutical composition of any one of (10) to (13), wherein the substance is a protein substance.

(15) The pharmaceutical composition of (14), wherein the protein substance is selected from the group consisting of:
   a) an antibody which binds to AILIM or a portion thereof;
   b) a polypeptide comprising the whole or a portion of an extracellular region of AILIM;
   c) a fusion polypeptide comprising the whole or a portion of an extracellular region of AILIM and the whole or a portion of a constant region of immunoglobulin heavy chain; and
   d) a polypeptide which binds to AILIM.

(16) The pharmaceutical composition of any one of (10) to (13), wherein the substance is a non-protein substance.

(17) The pharmaceutical composition of (16), wherein the non-protein substance is DNA, RNA, or a chemically synthesized compound.

(18) A pharmaceutical composition for preventing, treating, or prophylaxis of graft versus host reaction and immune rejection accompanying graft versus host reaction or transplantation of a tissue or organ, comprising a substance having an activity in modulating signal transduction mediated by AILIM, and a pharmaceutically acceptable carrier.

(19) The pharmaceutical composition of (18), wherein the substance has an activity in inhibiting proliferation of AILIM-expressing cells or inhibiting production of a cytokine by AILIM-expressing cells.

(20) The pharmaceutical composition of (19), wherein the cytokine is interferon γ which is a cytokine produced by Th1 type T cells, or interleukin 4 which is a cytokine produced by Th2 type T cells.

(21) The pharmaceutical composition of any one of (18) to (20), wherein the substance is a protein substance.

(22) The pharmaceutical composition of (21), wherein the protein substance is selected from the group consisting of:
   a) an antibody which binds to AILIM or a portion thereof;
   b) a polypeptide comprising the whole or a portion of an extracellular region of AILIM;
   c) a fusion polypeptide comprising the whole or a portion of an extracellular region of AILIM and the whole or a portion of a constant region in immunoglobulin heavy chain; and
   d) a polypeptide which binds to AILIM.

(23) The pharmaceutical composition of any one of (18) to (20), wherein the substance is a non-protein substance.

(24) The pharmaceutical composition of (23), wherein the non-protein substance is DNA, RNA, or a chemically synthesized compound.

(25) A pharmaceutical composition for preventing immune response triggered by a foreign antigen or an autoantigen, comprising a substance having an activity in modulating signal transduction mediated by AILIM, and a pharmaceutically acceptable carrier.

(26) The pharmaceutical composition of (25), wherein the immune response is production of an antibody against the antigen, cell proliferation, or production of a cytokine.

(27) The pharmaceutical composition of (25) or (26), wherein the substance has an activity in inhibiting proliferation of AILIM-expressing cells or in inhibiting production of a cytokine by AILIM-expressing cells.

(28) The pharmaceutical composition of (27), wherein the cytokine is interferon γ which is a cytokine produced by Th1 type T cells, or interleukin 4 which is a cytokine produced by Th2 type T cells.

(29) The pharmaceutical composition of any one of (25) to (28), wherein the substance is a protein substance.

(30) The pharmaceutical composition of (29), wherein the protein substance is selected from the group consisting of:
   a) an antibody which binds to AILIM or a portion thereof;
   b) a polypeptide comprising the whole or a portion of an extracellular region of AILIM;
   c) a fusion polypeptide comprising the whole or a portion of an extracellular region of AILIM and the whole or a portion of a constant region of immunoglobulin heavy chain; and
   d) a polypeptide which binds to AILIM.

(31) The pharmaceutical composition of any one of (25) to (28), wherein the substance is a non-protein substance.

(32) The pharmaceutical composition of (31), wherein the non-protein substance is DNA, RNA, or a chemically synthesized compound.

The present inventions are described in detail herein below by defining general methods for producing antibodies and terminologies of the present invention.

Herein, "mammal" means human, bovine, goat, rabbit, mouse, rat, hamster, and guinea pig; preferred is human, rabbit, rat, mouse, or hamster, and particularly preferred is human.

"AILIM" used herein stands for "activation inducible lymphocyte immunomodulatory molecule". This AILIM means a mammalian novel cell membrane surface molecule which has been recently identified, isolated, reported in JP-A Hei 11-29599 (Japanese Patent Application No. Hei 10-62217), which corresponds to WO98/38216 (PCT/JP98/00837), and named "JTT-1 antigen" or "JTT-2 antigen" by the present inventors.

Specifically, in the above patent applications, "AILIM" of the present invention means human AILIM comprising an amino acid sequence of SEQ ID NO: 1 (human JTT-1 antigen), rat AILIM comprising an amino acid sequence of SEQ ID NO: 4 or 6 (rat JTT-1 antigen), and mouse AILIM comprising an amino acid sequence of SEQ ID NO: 5 (mouse JTT-1 antigen).

About a human derived molecule completely identical to human AILIM, Kroczek et al. reported in two references published after the above-mentioned two patent applications by the present inventors had been laid open to public. They designated the human derived molecule ICOS (inducible costimulator) or 8F4 (WO99/15553; Nature Vol. 397, pp. 263-266, 1999). The human derived molecule named ICOS or 8F4 is incorporated as a molecule identical to human AILIM.

Moreover, "AILIM" used herein also includes a polypeptide having substantially the same amino acid sequence as that of AILIM of each mammal described in the references, and particularly preferably, that of human AILIM (the amino acid sequence of SEQ ID NO: 2 in JP-A Hei 11-29599, which corresponds to WO98/38216).

Here, "having substantially the same amino acid sequence" means that a polypeptide having an amino acid sequence where multiple amino acids, preferably 1 to 10 amino acids, particularly preferably 1 to 5 amino acids, in the amino acid sequence shown in the references are substituted, deleted, and/or modified, and a polypeptide having an amino acid sequence where multiple amino acids, preferably 1 to 10 amino acids, particularly preferably 1 to 5 amino acids, are added to the amino acid sequence shown in the references are also included in "AILIM" of the present invention as long as the polypeptide has substantially the same biological properties as the polypeptide comprising the amino acid sequence shown in the references.

Such substitution, deletion, or insertion of amino acids can be achieved according to the usual method (Experimental Medicine: SUPPLEMENT, "Handbook of Genetic Engineering" (1992); and so on).

Examples thereof are synthetic oligonucleotide site-directed mutagenesis (gapped duplex method), point mutagenesis by which a point mutation is introduced at random by treatment with nitrite or sulfite, the method by which a deletion mutant is prepared with Bal31 enzyme and the like, cassette mutagenesis, linker scanning method, miss incorporation method, mismatch primer method, DNA segment synthesis method, etc.

Synthetic oligonucleotide site-directed mutagenesis (gapped duplex method) can be, for example, performed as follows. The region desired to be mutagenized is cloned into M13 phage vector having amber mutation to prepare the single-stranded phage DNA. After RF I DNA of M13 vector without amber mutation is linearized by restriction enzyme treatment, DNA is mixed with the single-stranded phage DNA mentioned above, denatured, and annealed thereby forming "gapped duplex DNA." A synthetic oligonucleotide into which mutations are introduced is hybridized with the gapped duplex DNA and the closed-circular double-stranded DNAs are prepared by the reactions with DNA polymerase and DNA ligase. E. coli mutS cells, deficient in mismatch repair activity, are transfected with this DNA. E. coli cells without suppressor activity are infected with the grown phages, and only phages without amber mutation are screened.

The method by which a point mutation is introduced with nitrite utilizes, for example the principle as mentioned below. If DNA is treated with nitrite, bases are deaminated to change adenine into hypoxanthine, cytosine into uracil, and guanine into xanthine. If deaminated DNA is introduced into cells, "A:T" and "G:C" are replaced with "G:C" and "A:T", respectively, because hypoxanthine, uracil, and xanthine form a base pair with cytosine, adenine, and thymine, respectively, in the DNA replication. Actually, single-stranded DNA fragments treated with nitrite are hybridized with "gapped duplex DNA", and thereafter mutant strains are separated by manipulating in the same way as synthetic oligonucleotide site-directed mutagenesis (gapped duplex method).

"Mitogen" used herein is also called mitogenic factor and means a substance which induces cell division. Immunologically, it means a substance inducing blastogenesis of lymphocytes polyclonally and inducing cell division. Examples thereof are lectins such as PHA and PWM, Concanavalin A (ConA), lipopolysaccharides, streptolysin S, and anti-lymphocyte antibody. It is known that Concanavalin A and PHA act only on T lymphocytes, that lipopolysaccharides act only on B lymphocytes, and that PWM acts on both lymphocytes.

The term "lymphoblast cell" used herein is also called a large lymphocyte, lymphoblast, or immunoblast, and means a lymphocyte belonging to a large lymphocyte among lymphocytes existing in lymphoid tissues (lymph node, spleen, thymus, bone marrow, lymphoduct, tonsil, etc.) and blood.

The term "activated lymphocyte" used herein means, for example, a lymphocyte as mentioned below, but is not limited thereto. For example, the term means a lymphocyte activated by some stimulation. Lymphocytes are classified into T cells, B cells, and natural killer cells. T cells are classified into CD4-positive cells and CD8-positive cells. Therefore, the "activated lymphocytes" of the present invention include mainly activated T cells, activated B cells, and activated natural killer cells, and activated T cells include activated CD4-positive cells and activated CD8-positive cells.

Upon reacting with antigens presented by antigen-presenting cells, CD4-positive T cells secrete various cytokines (IFNγ, IL-4, etc.), newly express receptors for these cytokines, enlarge their own size, start cell dividing, proliferate, and are activated. Activated CD4-positive T cells include those in such a state.

CD8-positive T cells express IL-2R when they react with antigens. When IL-2 acts on IL-2R, the cells are differentiated into CTL, which has cellular cytotoxicity. CTL destroy its target cells to kill them when they meet the same antigen peptide/MHC class I complex. When CD8-positive T cells are differentiated into CTL, granules increase in the cytoplasm. These granules comprise various high molecular weight proteins, represented by perforin. Perforin resembles MAC composed of the fifth to ninth components of complement, and makes holes in the cell membrane of target cells. The granules also comprise serine proteases, LT, and proteoglycan. If CD8-positive cells receive antigen stimulation and are differentiated into CTL, they also secrete lymphokines such as IFNγ, LT, TNF, or IL-2. Activated CD8-positive T cells include those in such a state.

T cells show blast formation phenomenon when they react with hemagglutinin (phytohemagglutinin, PHA) or Concanavalin A (ConA). Activated T cells include those in such a state.

B cells express B7 molecules, activate helper T cells by stimulating CD28 on their surface with TCR, allow the helper T cells to express CD40L, or produce lymphokines. When the cells receive stimulation, they change to expand their cell size or proliferate. Activated B cells include those in such a state. In the present invention, activated B cells include those secreting antibodies (antibody-secreting cells and plasma cells).

Activated natural killer cells mean those showing cytotoxic action on tumor cells or virus-infected cells as mentioned above. In the present invention, activated lymphocytes include thymus cells stimulated by Concanavalin A (ConA).

The "activated lymphoblast cell" used herein includes an activated "lymphoblast" that is generated when the lymphoblast mentioned above is stimulated with "mitogen" mentioned above such as Concanavalin A.

The term "resting lymphocyte" used herein means, in some case, an non-activated lymphocyte, which has not received the stimulation to activate cells, in contrast to an activated lymphocyte mentioned above.

"Cytokine" in "production of a cytokine by AILIM-expressing cells" constituting the present invention means an arbitrary cytokine which is produced by AILIM-expressing cells (especially, T cells).

Examples of the T cells are T cells of Th1 type and of Th2 type, and the cytokine of the present invention is specifically meant by the cytokine produced by the T cells of the Th1 type and/or an arbitrary cytokine produced by T cells of Th2 type.

Examples of a cytokine produced by T cells of Th1 type are IFN-γ, IL-2, TNF, IL-3, and those of a cytokine produced by T cells of Th2 type are IL-3, IL-4, IL-5, IL-10, TNF (Cell, Vol. 30, No. 9, pp. 343-346, 1998).

"A substance" composing the present invention, specifically "a substance having an activity in modulating the signal transduction mediated by AILIM", and more specifically "a substance having an activity in inhibiting proliferation of AILIM-expressing cells, or in inhibiting production of a cytokine by AILIM-expressing cells" means a natural substance present in the nature, or a artificially prepared arbitrary substance.

Here, "the signal transduction mediated by AILIM" means the signal transduction through AILIM, leading to a change of an arbitrary phenotype in the AILIM-expressing cells described above or in the following Examples (cell proliferation, activation of cells, inactivation of cells, apoptosis, and/or a change of an ability for producing an arbitrary cytokine from AILIM-expressing cells).

"The substance" can be mainly classified into "a protein substance" and "a non-protein substance". Examples of the "protein substances" are the following polypeptide, antibody (a polyclonal antibody, a monoclonal antibody, or a portion of a monoclonal antibody).

When the substance is an antibody, the substance is preferably a monoclonal antibody. When the substance is a monoclonal antibody, the substance includes not only a non-human mammal derived monoclonal antibody, but also the following recombinant chimeric monoclonal antibody, a recombinant humanized monoclonal antibody and human monoclonal antibody.

When the substance is a polypeptide, the substance includes the following polypeptide, a fragment of the polypeptide (an oligopeptide), a fusion polypeptide, a chemically modified one thereof. Examples of an oligopeptide are a peptide comprising 5 to 30 amino acids, preferably 5 to 20 amino acids. The chemical modification can be designed depending on various purposes, for example, the increased half-life in blood in the case of administering in vivo, or the increased tolerance against the degradation or increased absorption in digestive tract at the oral administration.

Examples of the polypeptide are as follows:
(1) A polypeptide comprising the whole or a portion of an extracellular region of AILIM;
(2) A fusion polypeptide comprising the whole or a portion of an extracellular region of AILIM and the whole or a portion of a constant region of immunoglobulin heavy chain; or
(3) A polypeptide which binds to AILIM.

Examples of the "non-protein" are DNA, RNA, and a chemically synthesized compound.

Here, "DNA" means "DNA comprising a partial nucleotide sequence of the DNA or chemically modified DNA thereof" useful as an antisense DNA pharmaceutical designed based on a nucleotide sequence of DNA (including cDNA and genomic DNA) encoding the above AILIM (preferably human AILIM). Specifically the antisense DNA can inhibit transcription of DNA encoding the AILIM into mRNA, or translation of the mRNA into a protein by hybridizing DNA or RNA encoding AILIM.

The "partial nucleotide sequence" as referred to here indicates a partial nucleotide sequence comprising an arbitrary number of nucleotides in an arbitrary region. The partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

When the DNA is used as an antisense DNA pharmaceutical, the DNA sequence can be modified chemically in part for extending the half-life (stability) of the blood concentration of the DNA administered to patients, for increasing the intracytoplasmic-membrane permeability of the DNA, or for increasing the degradation resistance or the absorption of the orally administered DNA in the digestive organs. The chemical modification includes, for example, the modification of the phosphate bonds, the riboses, the nucleotide bases, the sugar moiety, the 3' end and/or the 5' end in the structure of the oligonucleotide DNA.

The modification of phosphate bond includes, for example, the conversion of one or more of the bonds to phosphodiester bonds (D-oligo), phosphorothioate bonds, phosphorodithioate bonds (S-oligo), methyl phosphonate (MP-oligo), phosphoroamidate bonds, non-phosphate bonds or methyl phosphonothioate bonds, or combinations thereof. The modification of the ribose includes, for example, the conversion to 2'-fluororibose or 2'-O-methylribose. The modification of the nucleotide base includes, for example, the conversion to 5-propynyluracil or 2-aminoadenine.

Here, "RNA" means "RNA comprising a partial nucleotide sequence of the RNA or chemically modified RNA thereof" useful as an antisense RNA pharmaceutical designed based on a nucleotide sequence of RNA encoding the above AILIM (preferably human AILIM). The antisense RNA can inhibit transcription of DNA encoding the AILIM into mRNA, or translation of the mRNA into a protein by hybridizing DNA or RNA encoding AILIM.

The "partial nucleotide sequence" as referred to here indicates a partial nucleotide sequence comprising an arbitrary number of nucleotides in an arbitrary region. The partial nucleotide sequence consists of 5 to 100 consecutive nucleotides, preferably 5 to 70 consecutive nucleotides, more preferably 5 to 50 consecutive nucleotides, and still more preferably 5 to 30 consecutive nucleotides.

The sequence of antisense RNA can be modified chemically in part for extending the half-life (stability) of the blood concentration of the RNA administered to patients, for increasing the intracytoplasmic-membrane permeability of the RNA, or for increasing the degradation resistance or the absorption of the orally administered RNA in the digestive organ. An example of chemical modification is the chemical modification applied to the above antisense DNA.

Examples of "a chemically synthesized compound" are an arbitrary compound except for the above DNA, RNA and protein substances, having the molecular weight of about 100 to about 1000, preferably a compound having the molecular weight of about 100 to about 800, and more preferably the molecular weight of about 100 to about 600.

A "polypeptide" included in the definition of the above "substance" means a portion (a fragment) of a polypeptide chain constituting AILIM (preferably human AILIM), preferably the whole or a portion of an extracellular region of the polypeptide constituting AILIM (1 to 5 amino acids may be optionally added into the N-terminus and/or C-terminus of the region).

AILIM involving in the present invention is a transmembrane molecule penetrating cell membrane, comprising 1 or 2 polypeptide chains.

Here, a "transmembrane protein" means a protein that connects with membrane through the hydrophobic peptide region penetrating the lipid bilayer of the membrane once or several times and whose structure is, as a whole, composed of three main regions, that is, extracellular region, transmembrane region, and cytoplasmic region, as seen in many receptors or cell surface molecules. Such a transmembrane protein constitutes each receptor or cell surface molecule in the form of a monomer, homodimer, heterodimer or oligomer with another chain(s) having the same or different amino acid sequence.

Here, an "extracellular region" means the whole or a portion from the partial structure (partial region) from the entire structure of the above-mentioned transmembrane protein where the partial structure exists outside of the membrane. In other words, it means the whole or a portion of the region of the transmembrane protein except the region incorporated into the membrane (transmembrane region) and the region existing in the cytoplasm following the transmembrane region (cytoplasmic region).

"A fusion polypeptide" included in the above "protein substance" means a fusion polypeptide comprising the whole or a portion of an extracellular region of a polypeptide constituting AILIM (preferably human AILIM), and "the whole or a portion of a constant region of immunoglobulin heavy chain (Ig, preferably human Ig)". Preferably, the fusion polypeptide is a fusion polypeptide with an extracellular region of AILIM and a portion of a constant region of human IgG heavy chain and particularly preferably, a fusion polypeptide of an extracellular region of AILIM and a region (Fc) of human IgG heavy chain comprising a hinge region, CH2 domain and CH3 domain. As IgG, IgG1 is preferable, and as AILIM, human, mouse, or rat AILIM is preferable (preferably human).

"The whole or a portion of a constant region of human immunoglobulin (Ig) heavy chain" used herein means the constant region or the Fc region of human-derived immunoglobulin heavy chain (H chain) as described, or a portion thereof. The immunoglobulin can be any immunoglobulin belonging to any class and any subclass. Specifically, examples of the immunoglobulin are IgG (IgG1, IgG2, IgG3, and IgG4), IgM, IgA (IgA1 and IgA2), IgD, and IgE. Preferably, the immunoglobulin is IgG (IgG1, IgG2, IgG3, or IgG4), or IgM. Examples of particularly preferable immunoglobulin of the present invention are those belonging to human-derived IgG (IgG1, IgG2, IgG3, or IgG4).

Immunoglobulin has a Y-shaped structural unit in which four chains composed of two homologous light chains (L chains) and two homologous heavy chains (H chains) are connected through disulfide bonds (S—S bonds). The light chain is composed of the light chain variable region ($V_L$) and the light chain constant region ($C_L$). The heavy chain is composed of the heavy chain variable region ($V_H$) and the heavy chain constant region ($C_H$).

The heavy chain constant region is composed of some domains having the amino acid sequences inherent in each class (IgG, IgM, IgA, IgD, and IgE) and each subclass (IgG1, IgG2, IgG3, and IgG4, IgA1, and IgA2).

The heavy chain of IgG (IgG1, IgG2, IgG3, and IgG4) is composed of $V_H$, CH1 domain, hinge region, CH2 domain, and CH3 domain in this order from N terminus.

Similarly, the heavy chain of IgG1 is composed of $V_H$, $C\gamma_1 1$ domain, hinge region, $C\gamma_1 2$ domain, and $C\gamma_1 3$ domain in this order from N terminus. The heavy chain of IgG2 is composed of $V_H$, $C\gamma_2 1$ domain, hinge region, $C\gamma_2 2$ domain, and $C\gamma_2 3$ domain in this order from N terminus. The heavy chain of IgG3 is composed of $V_H$, $C\gamma_3 1$ domain, hinge region, $C\gamma_3 2$ domain, and $C\gamma_3 3$ domain in this order from N terminus. The heavy chain of IgG4 is composed of $V_H$, $C\gamma_4 1$ domain, hinge region, $C\gamma_4 2$ domain, and $C\gamma_4 3$ domain in this order from N terminus.

The heavy chain of IgA is composed of $V_H$, $C\alpha 1$ domain, hinge region, $C\alpha 2$ domain, and $C\alpha 3$ domain in this order from N terminus.

Similarly, the heavy chain of IgA1 is composed of $V_H$, $C\alpha_1 1$ domain, hinge region, $C\alpha_1 2$ domain, and $C\alpha_1 3$ domain in this order from N terminus. The heavy chain of IgA2 is composed of $V_H$, $C\alpha_2 1$ domain, hinge region, $C\alpha_2 2$ domain, and $C\alpha_2 3$ domain in this order from N terminus.

The heavy chain of IgD is composed of $V_H$, $C\delta 1$ domain, hinge region, $C\delta 2$ domain, and $C\delta 3$ domain in this order from N terminus.

The heavy chain of IgM is composed of $V_H$, $C\mu 1$ domain, $C\mu 2$ domain, $C\mu 3$ domain, and $C\mu 4$ domain in this order from N terminus and have no hinge region as seen in IgG, IgA, and IgD.

The heavy chain of IgE is composed of $V_H$, $C\epsilon 1$ domain, $C\epsilon 2$ domain, $C\epsilon 3$ domain, and $C\epsilon 4$ domain in this order from N terminus and have no hinge region as seen in IgG, IgA, and IgD.

If, for example, IgG is treated with papain, it is cleaved at the slightly N terminal side beyond the disulfide bonds existing in the hinge region where the disulfide bonds connect the two heavy chains to generate two homologous Fab, in which a heavy chain fragment composed of $V_H$ and CH1 is connected with one light chain through a disulfide bond, and one Fc, in which two homologous heavy chain fragments composed of the hinge region, CH2 domain, and CH3 domain are connected through disulfide bonds (See "Immunology Illustrated", original 2nd ed., Nankodo, pp. 65-75 (1992); and "Focus of Newest Medical Science 'Recognition Mechanism of Immune System'", Nankodo, pp. 4-7 (1991); and so on).

Namely, "a portion of a constant region of immunoglobulin heavy chain" mentioned above means a portion of a constant region of an immunoglobulin heavy chain having the structural characteristics as mentioned above, and preferably, is the constant region without C1 domain, or the Fc region. Specifically, example thereof is the region composed of hinge region, C2 domain, and C3 domain from each of IgG, IgA, and IgD, and is the region composed of C2 domain, C3 domain, and C4 domain from each of IgM and IgE. A particularly preferable example thereof is the Fc region of human-derived IgG1.

The fusion polypeptide mentioned above has the advantage that the fusion polypeptide can be purified extremely easily by using affinity column chromatography using the property of protein A, which binds specifically to the immunoglobulin fragment because the fusion polypeptide of the present invention has a portion of a constant region (for example Fc) of an immunoglobulin such as IgG as mentioned above as a fusion partner. Moreover, since various antibodies against the Fc of various immunoglobulins are available, an immunoassay for the fusion polypeptides can be easily performed with antibodies against the Fc.

"A polypeptide which binds to AILIM" is included in "a polypeptide" included in the definition of the above "substance".

Specific examples of "a polypeptide which binds to AILIM" are the whole or a portion of a polypeptide constituting known B7h, B7RP-1, GL50 or a molecule called LICOS which are ligands interacting with AILIM (Nature, Vol. 402, No. 6763, pp. 827-832, 1999; Nature Medicine, Vol. 5, No. 12, pp. 1365-1369, 1999; J. Immunology, Vol. 164, pp. 1653-1657, 2000; Curr. Biol., Vol. 10 No 6, pp. 333-336, 2000).

Preferably, the polypeptide is a polypeptide comprising the whole or a portion of an extracellular region of the above ligands (B7h, B7RP-1, GL50, LICOS), or a fusion polypeptide comprising the polypeptide, and the whole or a portion of a constant region of immunoglobulin heavy chain (preferably human immunoglobulin). Here, the terms "an extracellular region" and "a constant region of immunoglobulin heavy chain" have the same meaning as the above.

The polypeptide, a portion of the polypeptide (fragment), and fusion polypeptide mentioned above can be produced not only by recombinant DNA technology as mentioned below but also by a method well known in the art such as a chemical synthetic method and a cell culture method, or a modified method thereof.

The "antibody" of the present invention can be a polyclonal antibody (antiserum) or a monoclonal antibody against mammalian AILIM (particularly preferably human AILIM) defined above, and preferably a monoclonal antibody.

Specifically the antibody is an antibody having an activity in inhibiting proliferation of AILIM-expressing cells by biding to AILIM, or inhibiting production of interferon γ or interleukin 4 by AILIM-expressing cells through biding to AILIM.

The antibody of the present invention can be natural antibodies obtained by immunizing mammals such as mice, rats, hamsters, guinea pigs, and rabbits with the antigen, such as cells (natural cells, cell lines, tumor cells, etc.) expressing AILIM of the present invention, transformants prepared using recombinant DNA technology so as to overexpress AILIM on the surface thereof, polypeptides constituting AILIM, or the above-mentioned fusion polypeptides comprising the AILIM polypeptide or the extracellular region of AILIM. The antibody of the present invention also includes chimeric antibodies and humanized antibodies (CDR-grafted antibodies) that can be produced by recombinant DNA technology, and human antibodies that can be produced using human antibody-producing transgenic animals.

The monoclonal antibody includes those having any one isotype of IgG, IgM, IgA, IgD, or IgE. IgG or IgM is preferable.

The polyclonal antibody (antisera) or monoclonal antibody can be produced by the known methods. Namely, a mammal, preferably a mouse, rat, hamster, guinea pig, rabbit, cat, dog, pig, goat, horse, or cattle, or more preferably, a mouse, rat, hamster, guinea pig, or rabbit is immunized, for example, with an antigen mentioned above with Freund's adjuvant, if necessary.

The polyclonal antibody can be obtained from the serum obtained from the animal so immunized. In addition, the monoclonal antibodies are produced as follows. Hybridomas are prepared from the antibody-producing cells obtained from the animal so immunized and myeloma cells that are not capable of producing autoantibodies. The hybridomas are cloned, and clones producing the monoclonal antibodies showing the specific affinity to the antigen used for immunizing the mammal are screened.

Specifically, the monoclonal antibody can be produced as follows. Immunizations are performed by injecting or implanting once or several times the antigen as mentioned above as an immunogen, if necessary, with Freund's adjuvant, subcutaneously, intramuscularly, intravenously, through the footpad, or intraperitoneally into a non-human mammal, specifically a mouse, rat, hamster, guinea pig, or rabbit, preferably a mouse, rat, or hamster (including a transgenic animal generated so as to produce antibodies derived from another animal such as the transgenic mouse producing human antibody mentioned below). Usually, immunizations are performed once to four times every one to fourteen days after the first immunization. Antibody-producing cells are obtained from the mammal so immunized in about one to five days after the last immunization. The frequency and interval of immunizations can be appropriately arranged depending on, e.g., property of the immunogen used. Hybridomas that secrete a monoclonal antibody can be prepared by the method of Köhler and Milstein (Nature, Vol. 256, pp. 495-497 (1975)) and by its modified method. Namely, hybridomas are prepared by fusing antibody-producing cells contained in a spleen, lymph node, bone marrow, or tonsil obtained from the non-human mammal immunized as mentioned above, preferably a spleen, with myelomas without autoantibody-producing ability, which are derived from, preferably, a mammal such as a mouse, rat, guinea pig, hamster, rabbit, or human, or more preferably, a mouse, rat, or human.

For example, mouse-derived myeloma P3/X63-AG8.653 (653), P3/NSI/1-Ag4-1 (NS-1), P3/X63-Ag8.U1 (P3U1), SP2/0-Ag14 (Sp2/0, Sp2), PAI, F0, or BW5147, rat-derived myeloma 210RCY3-Ag.2.3, or human-derived myeloma U-266AR1, GM1500-6TG-A1-2, UC729-6, CEM-AGR, D1R11, or CEM-T15 can be used as a myeloma used for the cell fusion.

Hybridoma clones producing monoclonal antibodies can be screened by cultivating hybridomas, for example, in microtiter plates and by measuring the reactivity of the culture supernatant in the well in which hybridoma growth is observed, to the immunogen used for the immunization mentioned above, for example, by enzyme immunoassay such as RIA and ELISA.

The monoclonal antibodies can be produced from hybridomas by cultivating the hybridomas in vitro or in vivo such as in the ascites fluid of a mouse, rat, guinea pig, hamster, or rabbit, preferably a mouse or rat, more preferably mouse and isolating the antibodies from the resulting the culture supernatant or ascites fluid of a mammal.

Cultivating hybridomas in vitro can be performed depending on, e.g., the property of cells to be cultured, the object of a test study, and the various conditions of a cultivating method, by using known nutrient media or any nutrient media derived from known basal media for growing, maintaining, and storing the hybridomas to produce monoclonal antibodies in culture supernatant.

Examples of basal media are low calcium concentration media such as Ham'F12 medium, MCDB153 medium, or low calcium concentration MEM medium, and high calcium concentration media such as MCDB104 medium, MEM medium, D-MEM medium, RPMI1640 medium, ASF104 medium, or RD medium. The basal media can contain, for example, sera, hormones, cytokines, and/or various inorganic or organic substances depending on the objective.

Monoclonal antibodies can be isolated and purified from the culture supernatant or ascites fluid mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

The "recombinant chimeric monoclonal antibody" is a monoclonal antibody prepared by genetic engineering, and specifically means a chimeric antibody such as mouse/human chimeric monoclonal antibody whose variable regions are derived from immunoglobulin of an non-human mammal (mouse, rat, hamster, etc.) and whose constant regions are derived from human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of the recombinant chimeric monoclonal antibody can be that of human immunoglobulin belonging to any isotype. Preferably, it is the constant region of human IgG.

The chimeric monoclonal antibody can be produced, for example, as follows. Needless to say, the production method is not limited thereto.

A mouse/human chimeric monoclonal antibody can be prepared, referring to Experimental Medicine: SUPPLEMENT, Vol. 1.6, No. 10 (1988); and Examined Published Japanese Patent Application (JP-B) No. Hei 3-73280. Namely, it can be prepared by operably inserting CH gene (C gene encoding the constant region of H chain) obtained from the DNA encoding human immunoglobulin downstream of active $V_H$ genes (rearranged VDJ gene encoding the variable region of H chain) obtained from the DNA encoding a mouse monoclonal antibody isolated from the hybridoma producing the mouse monoclonal antibody, and $C_L$ gene (C gene encoding the constant region of L chain) obtained from the DNA encoding human immunoglobulin downstream of active $V_L$ genes (rearranged VJ gene encoding the variable region of L chain) obtained from the DNA encoding the mouse monoclonal antibody isolated from the hybridoma, into the same or different vectors so as for them to be expressed, following by transforming host cells with the expression vector, and then by cultivating the transformants.

Specifically, DNAs are first extracted from mouse monoclonal antibody-producing hybridomas by the usual method, digested with appropriate restriction enzymes (for example, EcoRI and HindIII), electrophoresed (using, for example, 0.7% agarose gel), and analyzed by Southern blotting. After an electrophoresed gel is stained, for example, with ethidium bromide and photographed, the gel is given with marker positions, washed twice with water, and soaked in 0.25 M HCl for 15 minutes. Then, the gel is soaked in 0.4 N NaOH solution for 10 minutes with gently stirring. The DNAs are transferred to a filter for 4 hours by the usual method. The filter is recovered and washed twice with 2×SSC. After the filter is sufficiently dried, it is baked at 75° C. for 3 hours.

After baking, the filter is treated with 0.1×SSC/0.1% SDS at 65° C. for 30 minutes. Then, it is soaked in 3×SSC/0.1% SDS. The filter obtained is treated with prehybridization solution in a plastic bag at 65° C. for 3 to 4 hours.

Next, $^{32}$P-labeled probe DNA and hybridization solution are added to the bag and reacted at 65° C. about 12 hours. After hybridization, the filter is washed under appropriate salt concentration, reaction temperature, and time (for example, 2×SSC-0.1% SDS, room temperature, 10 minutes). The filter is put into a plastic bag with a little 2×SSC, and subjected to autoradiography after the bag is sealed.

Rearranged VDJ gene and VJ gene encoding H chain and L chain of a mouse monoclonal antibody are identified by Southern blotting mentioned above. The region comprising the identified DNA fragment is fractioned by sucrose density gradient centrifugation and inserted into a phage vector (for example, Charon 4A, Charon 28, λEMBL3, λEMBL4, etc.). E. coli (for example, LE392, NM539, etc.) is transformed with the phage vector to generate a genomic library. The genomic library is screened by plaque hybridization such as Benton-Davis method (Science, Vol. 196, pp. 180-182 (1977)) using appropriate probes (H chain J gene, L chain (κ) J gene, etc.) to obtain positive clones comprising rearranged VDJ gene or VJ gene. By making the restriction map and determining the nucleotide sequence of the clones obtained, it is confirmed that genes comprising the desired, rearranged $V_H$ (VDJ) gene or $V_L$ (VJ) gene are obtained.

Separately, human $C_H$ gene and human $C_L$ gene used for chimerization are isolated. For example, when a chimeric antibody with human IgG1 is produced, Cγ1 gene as a $C_H$ gene, and Cκ gene as a $C_L$ gene, are isolated. These genes can be isolated from human genomic library with mouse Cγ1 gene and mouse Cκ gene, corresponding to human Cγ1 gene and human Cκ gene, respectively, as probes, taking advantage of high homology between the nucleotide sequences of mouse immunoglobulin gene and that of human immunoglobulin gene.

Specifically, DNA fragments comprising human Cκ gene and an enhancer region are isolated from human λ Charon 4A HaeIII-AluI genomic library (Cell, Vol. 15, pp. 1157-1174 (1978)), for example, with a 3 kb HindIII-BamHI fragment of clone Ig146 (Proc. Natl. Acad. Sci. USA, Vol. 75, pp. 4709-4713 (1978)) and a 6.8 kb EcoRI fragment of clone MEP10 (Proc. Natl. Acad. Sci. USA, Vol. 78, pp. 474-478 (1981)) as probes. In addition, for example, after human fetal hepatocyte DNA is digested with HindIII and fractioned by agarose gel electrophoresis, a 5.9 kb fragment is inserted into λ788 and then human Cγ1 gene is isolated with the probes mentioned above.

Using mouse $V_H$ gene, mouse $V_L$ gene, human $C_H$ gene, and human $C_L$ gene so obtained, and taking promoter region and enhancer region into consideration, human $C_H$ gene is inserted downstream mouse $V_H$ gene and human $C_L$ gene is inserted downstream mouse $V_L$ gene into an expression vector such as pSV2gpt or pSV2neo with appropriate restriction enzymes and DNA ligase by the usual method. In this case, chimeric genes of mouse $V_H$ gene/human $C_H$ gene and mouse $V_L$ gene/human $C_L$ gene can be respectively inserted in the same expression vector or in different expression vectors.

Chimeric gene-inserted expression vector(s) thus prepared are introduced into myelomas that do not produce antibodies, for example, P3X63.Ag8.653 cells or SP210 cells by protoplast fusion method, DEAE-dextran method, calcium phosphate method, or electroporation method. The transformants are screened by cultivating in media containing a drug corresponding to the drug resistance gene inserted into the expression vector and, then, cells producing desired chimeric monoclonal antibodies are obtained.

Desired chimeric monoclonal antibodies are obtained from the culture supernatant of antibody-producing cells thus screened.

The "humanized monoclonal antibody (CDR-grafted antibody)" of the present invention is a monoclonal antibody prepared by genetic engineering and specifically means a humanized monoclonal antibody wherein a portion or the whole of the complementarity determining regions of the hypervariable region are derived from the complementarity determining regions of the hypervariable region from a monoclonal antibody of an non-human mammal (mouse, rat, hamster, etc.), the framework regions of the variable region are derived from the frame work regions of the variable region from human immunoglobulin, and the constant region is derived from human a constant region from immunoglobulin.

The complementarity determining regions of the hypervariable region exists in the hypervariable region in the variable region of an antibody and means three regions which directly and complementary binds to an antigen (complementarity-determining residues, CDR1, CDR2, and CDR3). The framework regions of the variable region mean four comparatively conserved regions lying upstream, downstream or between the three complementarity determining regions (framework region, FR1, FR2, FR3, and FR4).

In other words, a humanized monoclonal antibody means that in which all the regions except a portion or the whole of the complementarity determining regions of the hypervariable region of a non-human mammal-derived monoclonal antibody have been replaced with their corresponding regions derived from a human immunoglobulin.

The constant region derived from human immunoglobulin has the amino acid sequence inherent in each isotype such as IgG (IgG1, IgG2, IgG3, IgG4), IgM, IgA, IgD, and IgE. The constant region of a humanized monoclonal antibody in the present invention can be that from human immunoglobulin belonging to any isotype. Preferably, it is the constant region of human IgG. The framework regions of the constant region derived from human immunoglobulin are not particularly limited.

The humanized monoclonal antibody can be produced, for example, as follows. Needless to say, the production method is not limited thereto.

For example, a recombinant humanized monoclonal antibody derived from mouse monoclonal antibody can be prepared by genetic engineering, referring to Published Japanese Translation of International Publication (JP-WA) No. Hei 4-506458 and JP-A Sho 62-296890. Namely, at least one mouse H chain CDR gene and at least one mouse L chain CDR gene corresponding to the mouse H chain CDR gene are isolated from hybridomas producing mouse monoclonal antibody, and human H chain gene encoding the whole regions except human H chain CDR corresponding to mouse H chain CDR mentioned above and human L chain gene encoding the whole region except human L chain CDR corresponding to mouse L chain CDR mentioned above are isolated from human immunoglobulin genes.

The mouse H chain CDR gene(s) and the human H chain gene(s) so isolated are operably inserted into an appropriate vector so that they can be expressed. Similarly, the mouse L chain CDR gene(s) and the human L chain gene(s) are operably inserted into another appropriate vector so that they can be expressed. Alternatively, the mouse H chain CDR gene (s)/human H chain gene (s) and mouse L chain CDR gene (s)/human L chain gene(s) can be operably inserted into the same expression vector so that they can be expressed.

Host cells are transformed with the expression vector thus prepared to obtain transformants producing humanized monoclonal antibody. By cultivating the transformants, desired humanized monoclonal antibody is obtained from culture supernatant.

The "human monoclonal antibody" is immunoglobulin in which the entire regions comprising the variable and constant region of H chain, and the variable and constant region of L chain constituting immunoglobulin are derived from the genes encoding human immunoglobulin.

The human antibody (preferably human monoclonal antibody) can be produced in the same way as the production method of polyclonal or monoclonal antibodies mentioned above by immunizing, with an antigen, a transgenic animal which for example, at least human immunoglobulin gene(s) have been integrated into the locus of a non-human mammal such as a mouse by the usual method.

For example, a transgenic mouse producing human antibodies is prepared by the methods described in Nature Genetics, Vol. 7, pp. 13-21 (1994); Nature Genetics, Vol. 15, pp. 146-156 (1997); JP-WA Hei 4-504365; JP-WA Hei 7-509137; Nikkei Science, No. 6, pp. 40-50 (1995); WO94/25585; Nature, Vol. 368, pp. 856-859 (1994); and JP-WA No. Hei 6-500233.

In addition, recently developed technique for producing a human-derived protein from the milk of a transgenic cow or pig can also be applied (Nikkei Science, pp. 78-84 (April, 1997)).

The "portion of an antibody" used in the present invention means a partial region of the monoclonal antibody as mentioned above, and specifically, means $F(ab')_2$, Fab', Fab, Fv (variable fragment of antibody), sFv, dsFv (disulfide stabilized Fv), or dAb (single domain antibody) (Exp. Opin. Ther. Patents, Vol. 6, No. 5, pp. 441-456 (1996)).

"F $(ab')_2$" and "Fab'" can be produced by treating immunoglobulin (monoclonal antibody) with a protease such as pepsin and papain, and means an antibody fragment generated by digesting immunoglobulin near the disulfide bonds in the hinge regions existing between each of the two H chains. For example, papain cleaves IgG upstream of the disulfide bonds in the hinge regions existing between each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma1$ ($\gamma1$ region in the constant region of H chain) are connected at their C terminal regions through a disulfide bond. Each of such two homologous antibody fragments is called Fab'. Pepsin also cleaves IgG downstream of the disulfide bonds in the hinge regions existing between each of the two H chains to generate an antibody fragment slightly larger than the fragment in which the two above-mentioned Fab' are connected at the hinge region. This antibody fragment is called $F(ab')_2$.

"A pharmaceutical composition" of the present invention is the pharmaceutical composition comprising "the substance" defined above, specifically "a substance having an activity in modulating the signal transduction mediated by AILIM", more specifically "a substance having an activity in inhibiting proliferation of AILIM-expressing cells, or in inhibiting production of a cytokine by AILIM-expressing cells" as well as a pharmaceutically acceptable carrier. Specifically, the pharmaceutical composition of the present invention is a pharmaceutical composition comprising "the protein substance" or "the non-protein substance" defined above and a pharmaceutically acceptable carrier. More specifically, the pharmaceutical composition of the present invention is a pharmaceutical composition comprising any one of the polypeptide, a portion of the polypeptide (a fragment), the fusion polypeptide, the polyclonal antibody, the monoclonal antibody or a portion of the monoclonal antibody defined above, and a pharmaceutically acceptable carrier.

The "pharmaceutically acceptable carrier" includes a excipient, a diluent, an expander, a decomposition agent, a stabilizer, a preservative, a buffer, an emulsifier, an aromatic, a colorant, a sweetener, a viscosity increasing agent, a flavor, a solubility increasing agent, or other additives. Using one or more of such carriers, a pharmaceutical composition can be formulated into tablets, pills, powders, granules, injections, solutions, capsules, troches, elixirs, suspensions, emulsions, or syrups. The pharmaceutical composition can be administered orally or parenterally. Other forms for parenteral administration include a solution for external application, suppository for rectal administration, and pessary, prescribed by the usual method, which comprises one or more active ingredient.

The dosage can vary depending on the age, sex, weight, and symptom of a patient, effect of treatment, administration route, period of treatment, or the kind of active ingredient (polypeptide or antibody mentioned above) contained in the pharmaceutical composition. Usually, the pharmaceutical composition can be administered to an adult in a dose of 10 μg to 1000 mg (or 10 μg to 500 mg) per one administration. Depending on various conditions, the dosage less than that mentioned above may be sufficient in some cases, and the dosage more than that mentioned above may be necessary in other cases.

In particular, the injection can be produced by dissolving or suspending the antibody in a non-toxic, pharmaceutically acceptable carrier such as physiological saline or commercially available distilled water for injection with adjusting a concentration to 0.1 μg antibody/ml carrier to 10 mg antibody/ml carrier. The injection thus produced can be administered to a human patient in need of treatment in a dose of 1 μg to 100 mg/kg body weight, preferably 50 μg to 50 mg/kg body weight once or more times a day. Examples of administration route are medically appropriate administration routes such as intravenous injection, subcutaneous injection, intradermal injection, intramuscular injection, or intraperitoneal injection, preferably intravenous injection.

The injection can also be prepared into a non-aqueous diluent (for example, propylene glycol, polyethylene glycol, vegetable oil such as olive oil, and alcohol such as ethanol), suspension, or emulsion.

The injection can be sterilized by filtration with a bacteria-non-penetrated filter, by mixing bacteriocide, or by irradiation. The injection can be produced in the form that is prepared upon use. Namely, it is freeze-dried to be a sterile solid composition, and can be dissolved in sterile distilled water for injection or another solvent before use.

The pharmaceutical composition of the present invention is useful for treating or prophylaxis of various autoimmune diseases, allergic diseases, or inflammatory diseases caused by the activation of lymphocytes such as T cells and the abnormality of regulation of activated lymphocyte functions.

Examples of the diseases are arthrosis (for example, rheumatoid arthritis, osteoarthritis), inflammation [for example, cerebritis, bronchitis, angiitis, pneumonia, hepatitis, myocarditis, pancreatis, intestinal enteritis, gastritis, peritonitis, nephritis (for example, glomerular nephritis), arthritis (for example, rheumatoid arthritis), inflammation in postischemic reperfusion injury (myocardial ischemic reperfusion injury), inflammation attributed to immune rejection, inflammatory bowel diseases, burn, inflammation in multiple organ failure, inflammation after operation of PTCA or PTCR, inflammation accompanying arteriosclerosis], various conditions caused by bacterial or viral infection (for example, inflammation), graft versus host reaction, immune rejection accompanying graft versus host reaction, transplantation of tissue(s) and organ(s), various diseases accompanied by excessive production of an antibody against a foreign antigen, caused by immunization with the foreign antigen, multiple sclerosis, autoimmune thyroiditis, various skin inflammation (allergic contact-type dermatitis, lichen planus which is chronic inflammatory skin disorder, psoriasis, scleroderma), and systemic lupus erythematosus.

Both acute and chronic inflammations are included in "inflammation" of the present invention. In general, acute inflammation is the inflammation in which the expression of inflammatory response is relatively rapid and the progression is also rapid, and the termination thereof is obvious. On the other hand, chronic inflammation means the inflammation in which the expression of inflammatory response is relatively slow, or gradual, or even the presence of the expression is too weak to be detected clearly and the expression prolongs from several weeks to several years and the termination is unclear.

Inflammation caused in an arbitrary tissue is included in the inflammation of the present invention. Specifically, inflammation in tissues in, for example, brain, eye, bronchi, blood vessel, lung, liver, heart, pancreas, stomach, intestine, mesentery, kidney, skin, nasal mucosa, or joint.

The therapeutic effect of the pharmaceutical composition of the present invention for symptom of various diseases can be tested by the usual method by administering it to a known disease model animal.

Sub figure (a) shows the expression pattern of CD3 and AILIM (alternatively called ThA). Sub figure (b) shows the expression pattern of CD3 and CD28.

Figure 2:
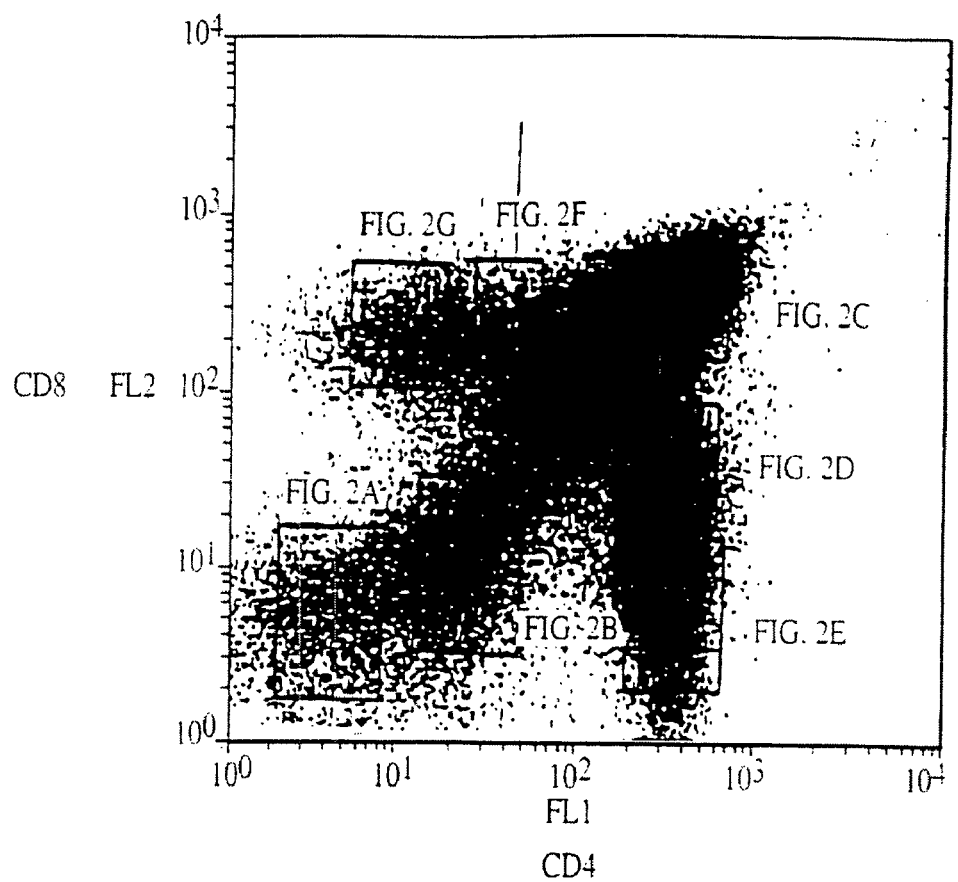
Figure 2A:
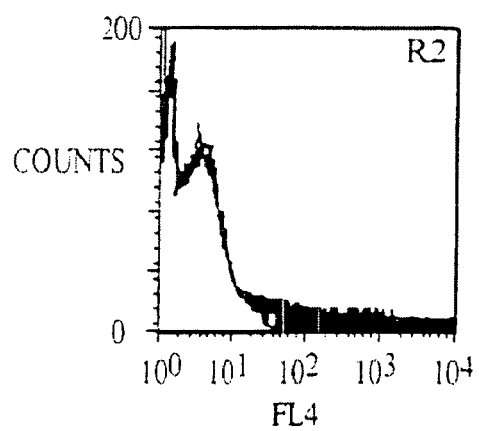
Figure 2B:
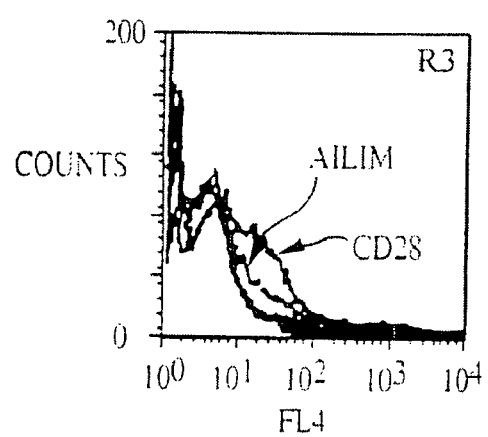
Figure 2C:
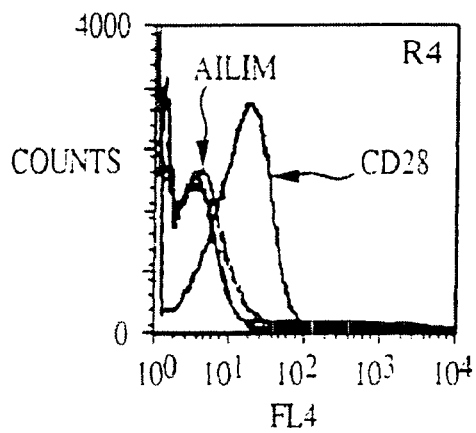
Figure 2D:
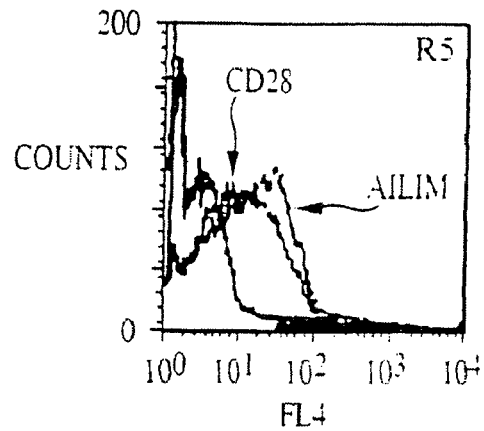
Figure 2E:
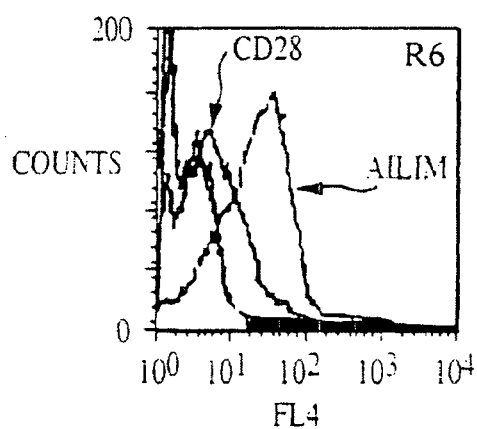
Figure 2F:
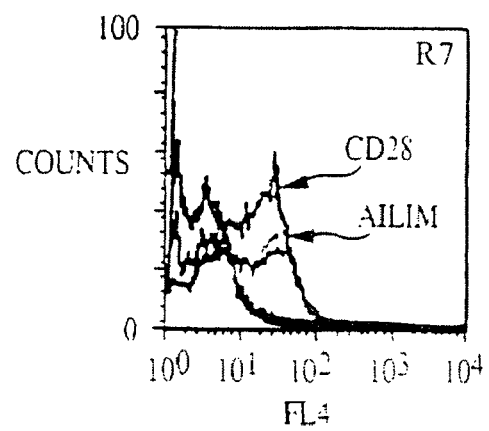
Figure 2G:
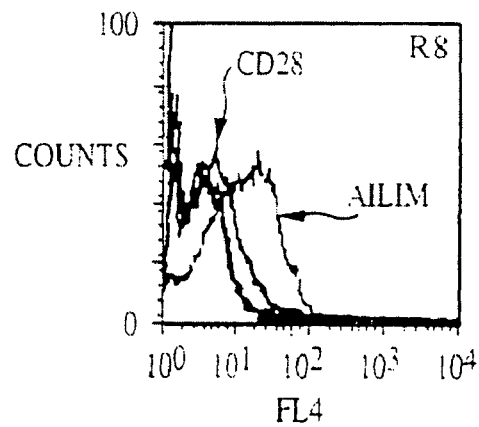

FIG. 2 shows the expression pattern of CD28 and AILIM in normal mouse thymus derived T cells at each differentiation stage of T cells, graded using the expression of CD4 and CD8 as an index.

R2 to R8 show the following:

R2: The expression pattern of AILIM and CD28 in CD4-negative CD8-negative T cells.

R3: The expression pattern of AILIM and CD28 in CD4-weakly positive CD8-weakly positive T cells.

R4: The expression pattern of AILIM and CD28 in CD4-positive CD8-positive cells.

R5: The expression pattern of AILIM and CD28 in CD4-positive CD8-weakly positive T cells.

R6: The expression pattern of AILIM and CD28 in CD4-positive CD8-negative cells.

R7: The expression pattern of AILIM and CD28 in CD4-weakly positive CD8-positive T cells.

R8: The expression pattern of AILIM and CD28 in CD4-negative CD8-positive T cells.

Figure 3:
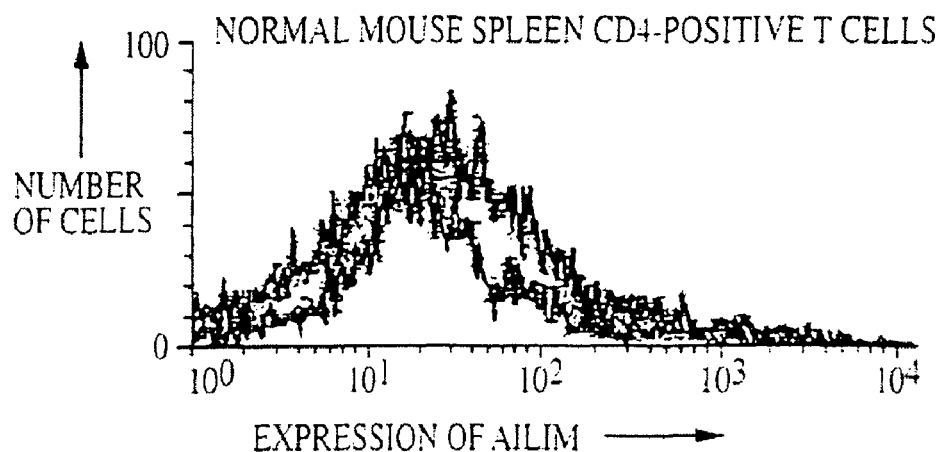

FIG. 3 shows the expression pattern for AILIM in CD4-positive T cells contained in normal mouse spleen tissues.

Figure 4:
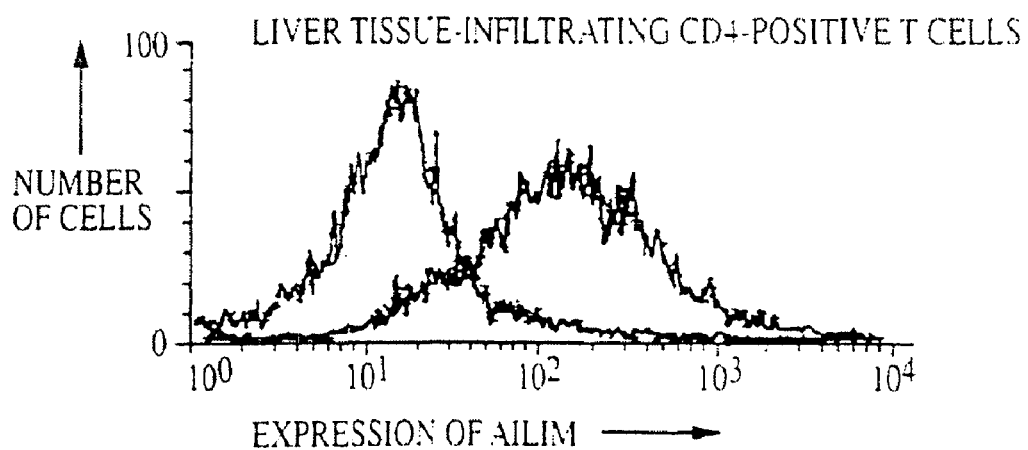
Figure 5A:
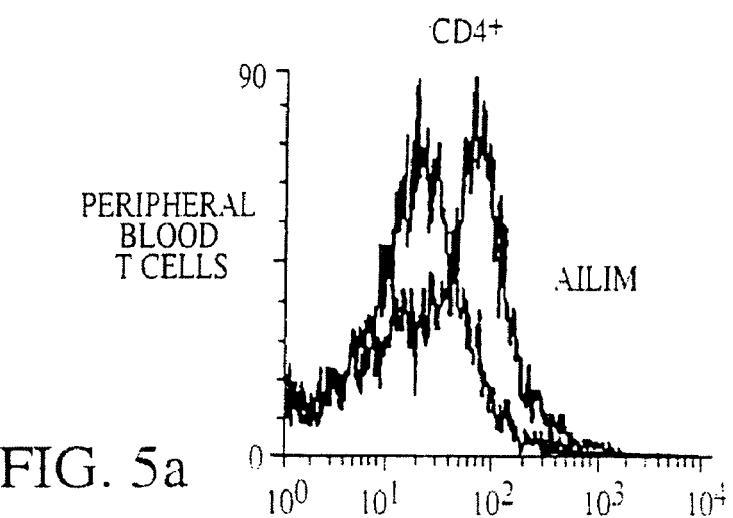
Figure 5B:
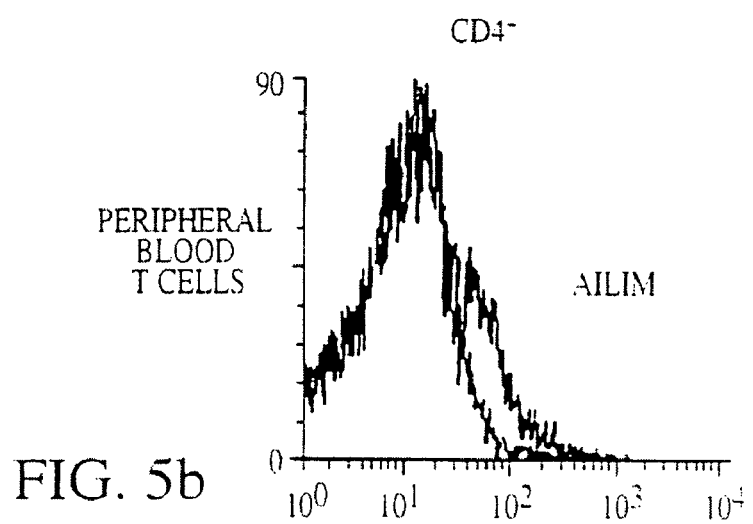
Figure 5C:
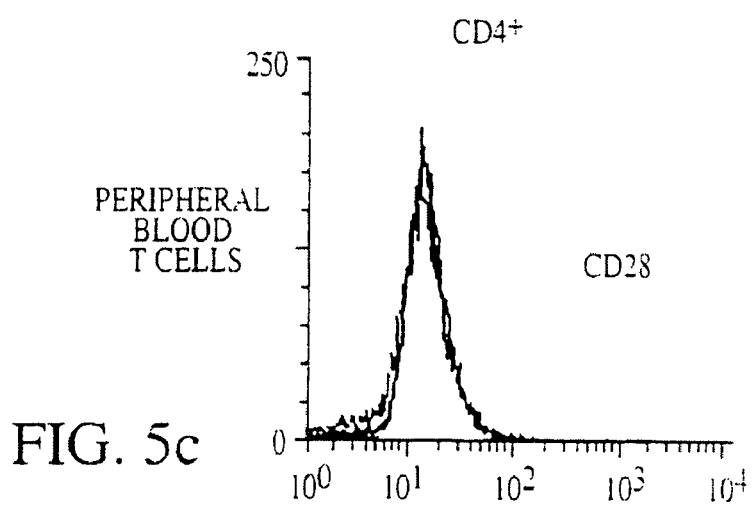
Figure 5D:
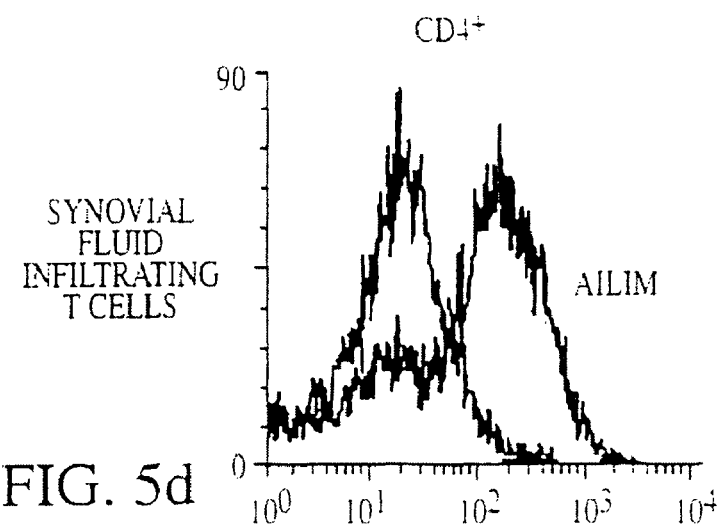
Figure 5E:
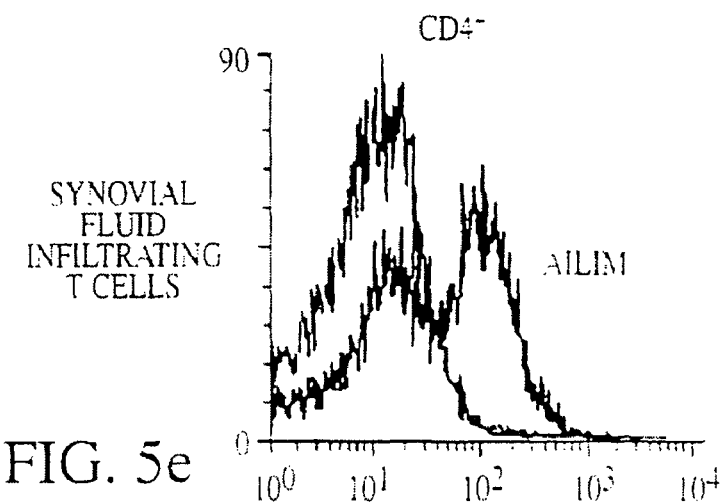
Figure 5F:
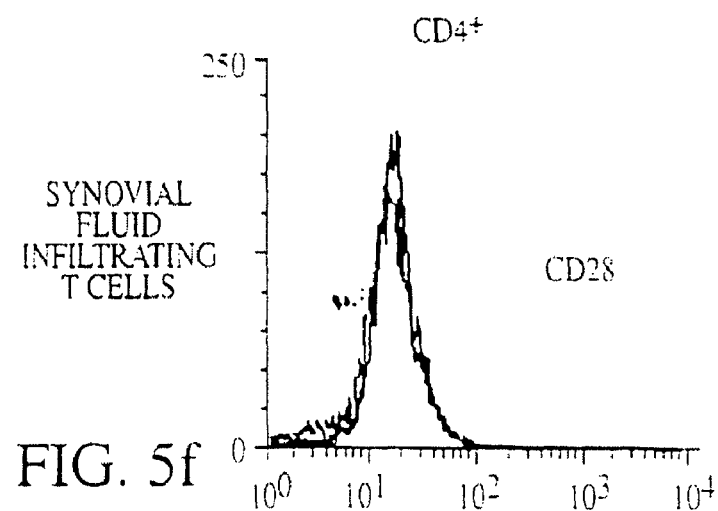
Figure 6A:
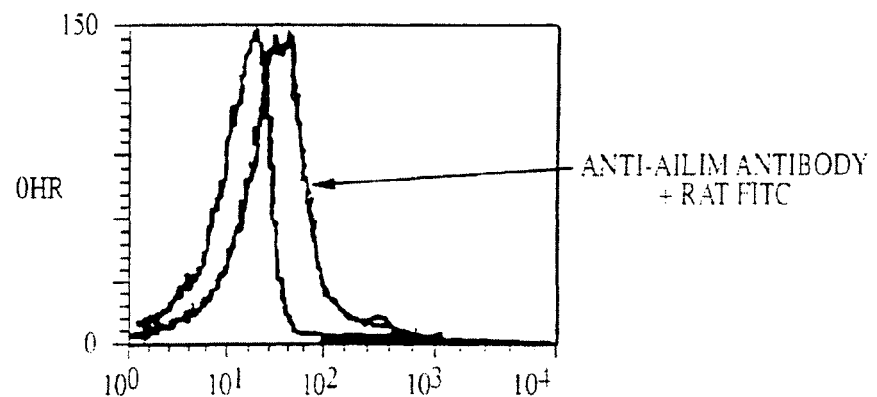
Figure 6B:
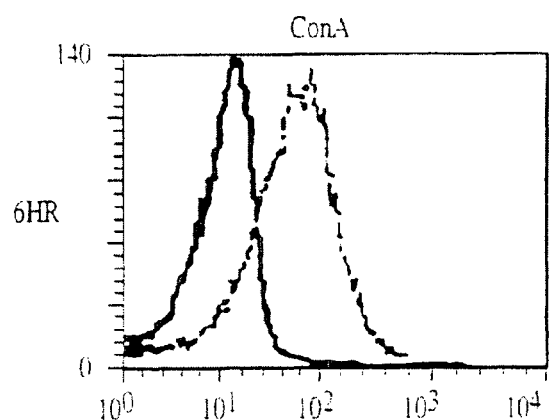
Figure 6C:
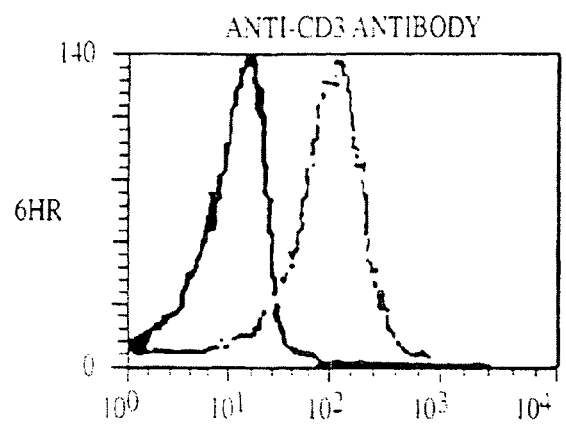
Figure 6D:
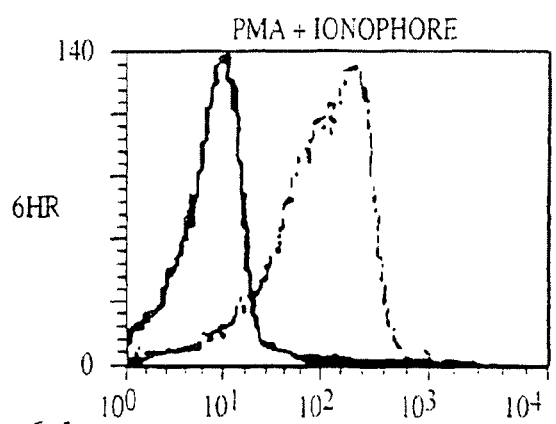
Figure 6E:
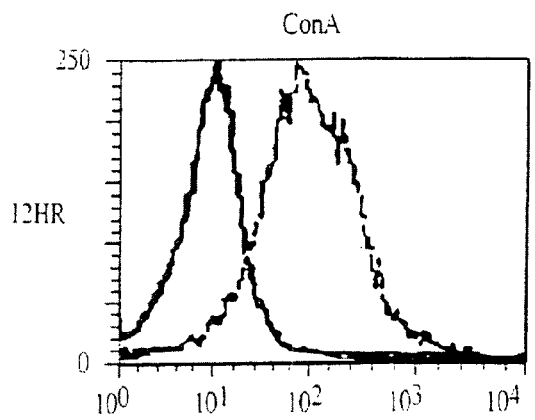
Figure 6H:
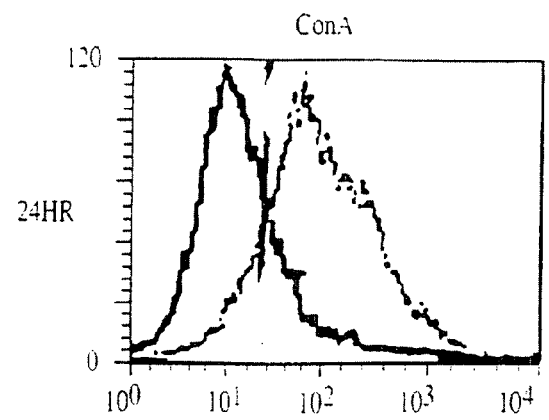
Figure 6F:
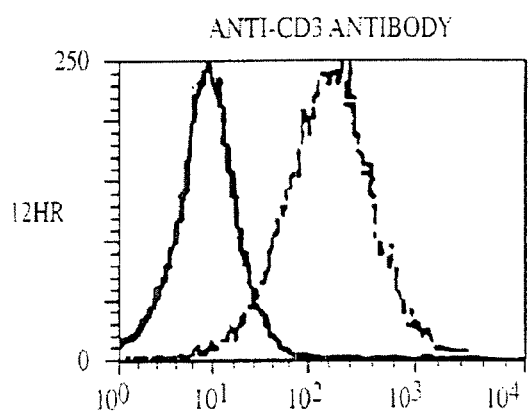
Figure 6I:
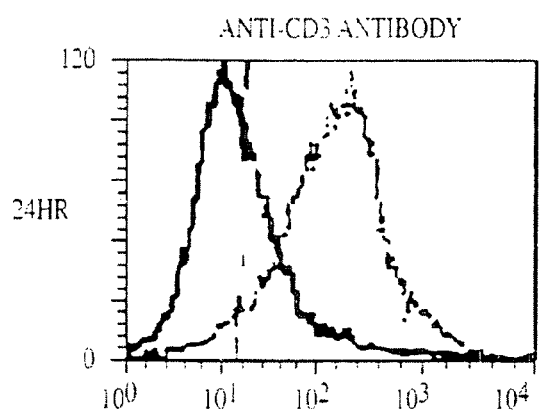
Figure 6G:
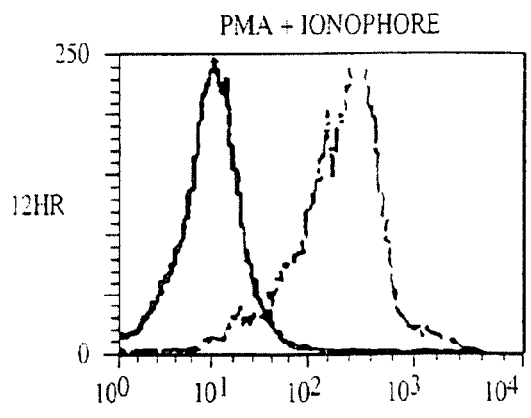
Figure 6J:
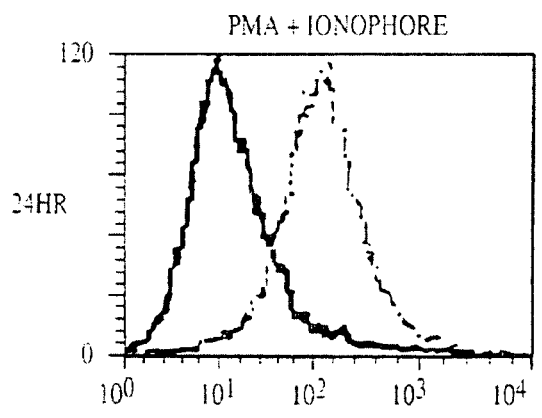

FIG. 4 shows the expression pattern for AILIM in liver tissue-infiltrating CD4-positive T cells in a host suffering from hepatitis.

FIG. 5 shows the expression pattern for AILIM and CD28 in each of CD4-positive T cells and CD4-negative T cells contained in peripheral blood T cells and synovial fluid-infiltrating T cells from a patient suffering from rheumatoid arthritis, respectively.

FIG. 6 shows the expression pattern for AILIM in the time course in lymphoid tissue-derived T cells from a normal mouse activated by stimulating with various stimulators.

FIG. 7 schematically shows the expression pattern and various properties for AILIM in various T cell strains and T cell derived hybridoma from a mouse.

Figure 8:
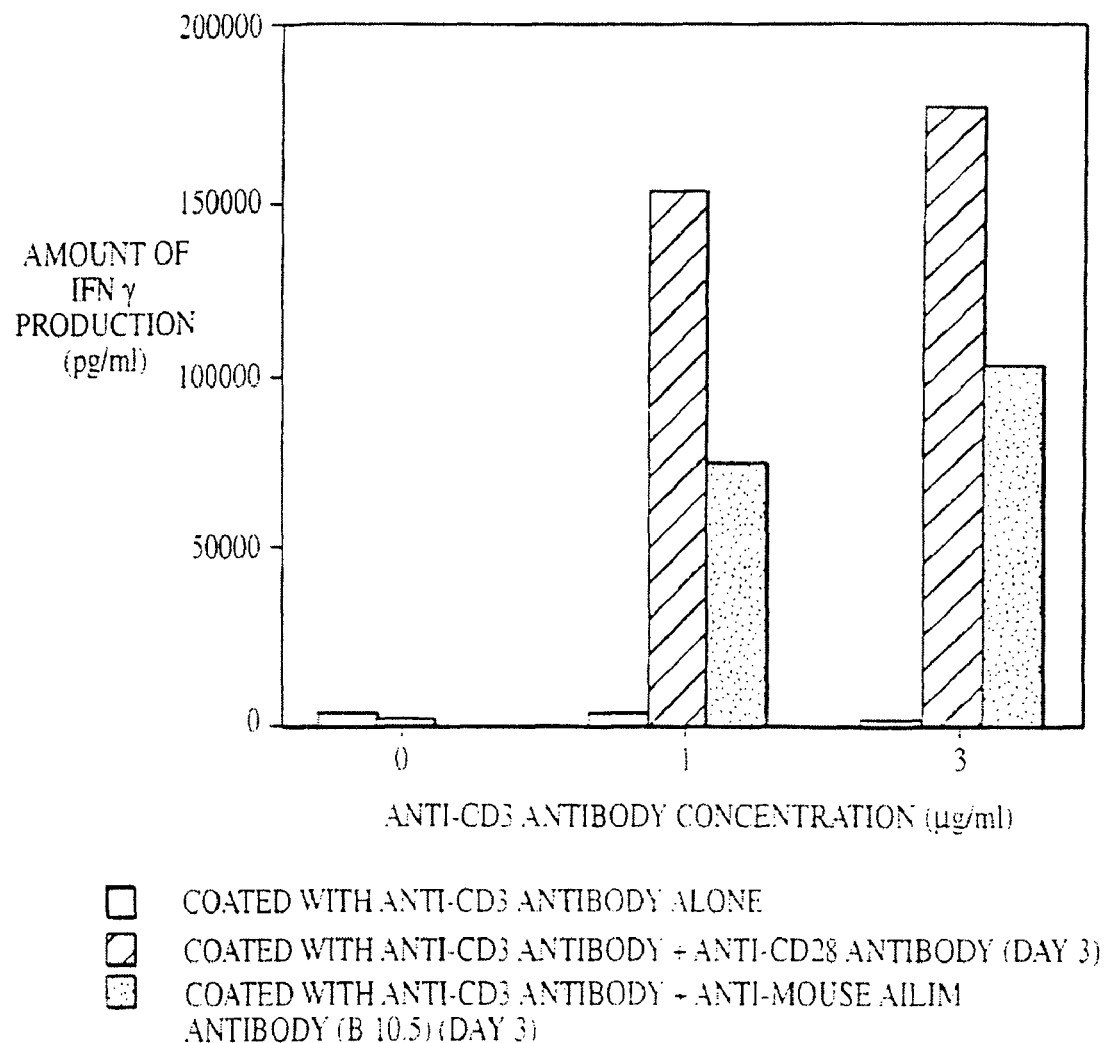

FIG. 8 shows the activation (induction of IFNγ production) of mouse spleen-derived T cells by crosslink of CD3 and AILIM realized by using a plate coated with anti-CD3 antibody and anti-AILIM antibody.

Figure 9:
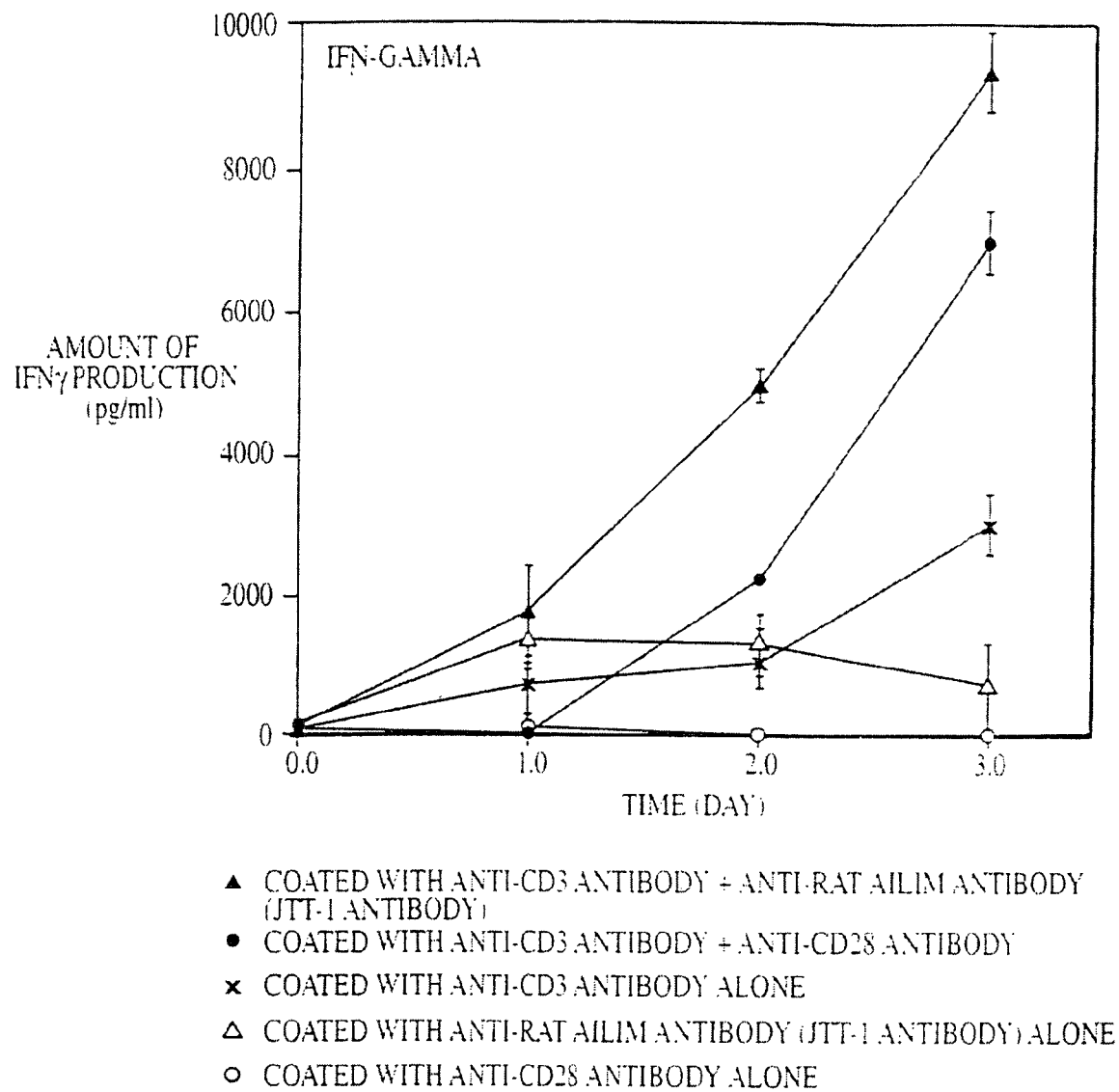

FIG. 9 shows the activation (induction of IFNγ production) of rat spleen-derived T cells by crosslink of CD3 and AILIM realized by using a plate coated with anti-CD3 antibody and anti-AILIM antibody.

Figure 10:
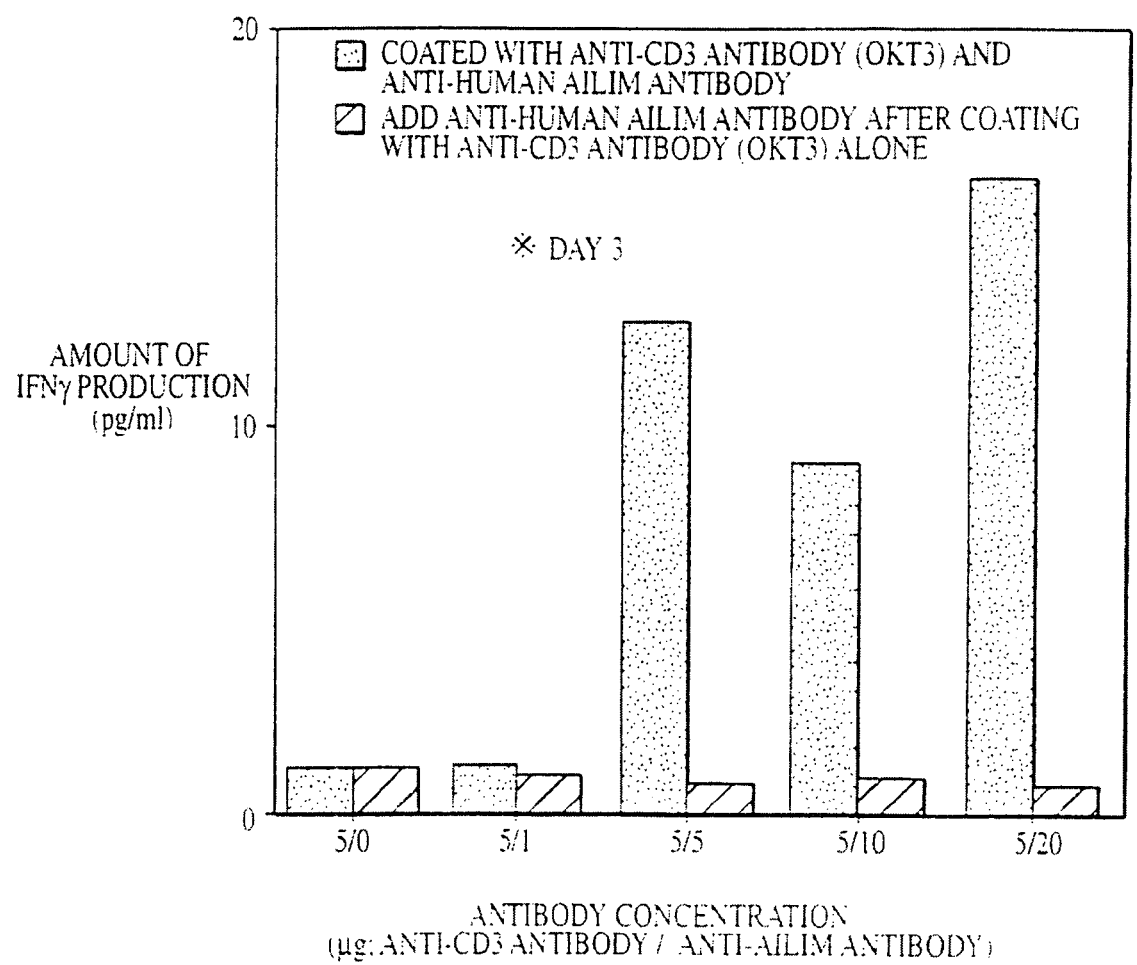

FIG. 10 shows the activation (induction of IFNγ production) of human peripheral blood-derived T cells by crosslink of CD3 and AILIM realized using a plate coated with anti-CD3 antibody and anti-AILIM antibody.

Figure 11:
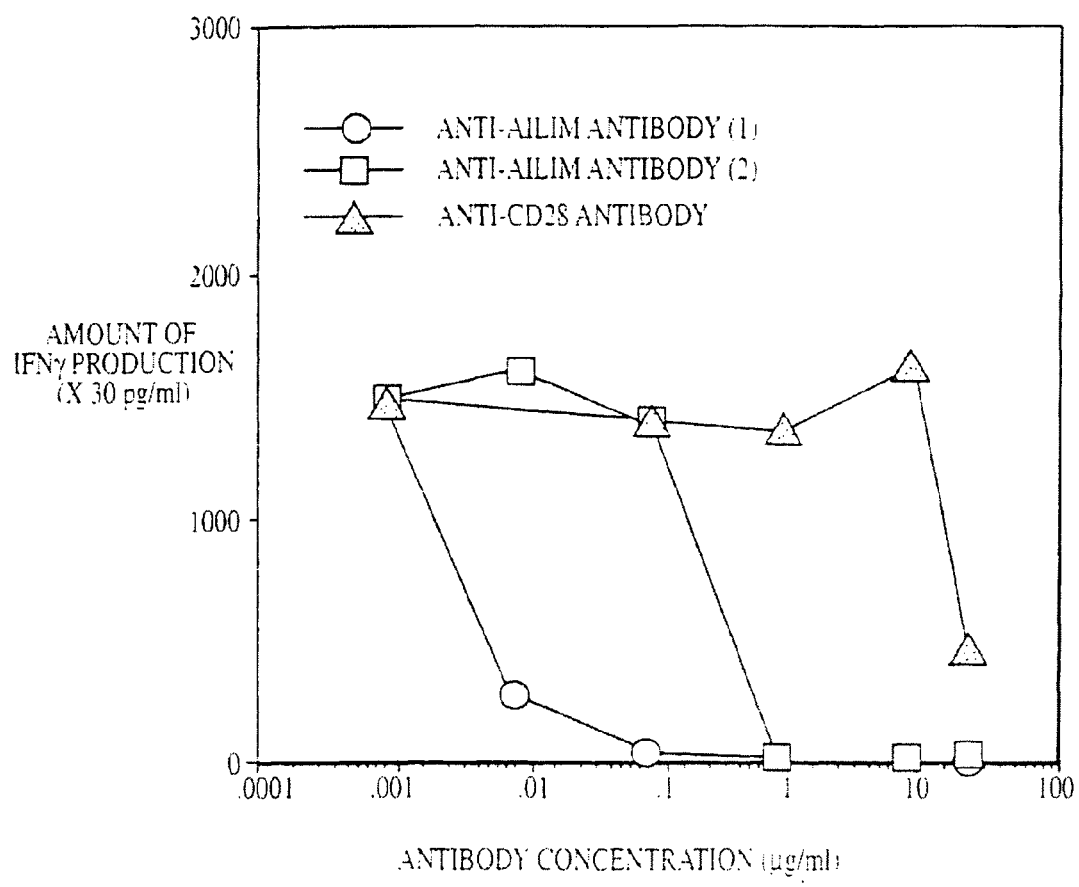

FIG. 11 shows the inhibitory effect of anti-AILIM antibody on the increased production of IFN γ, one of the T-cell responses, in human peripheral blood-derived T cells activated by stimulating with anti-CD3 antibody.

Figure 12:
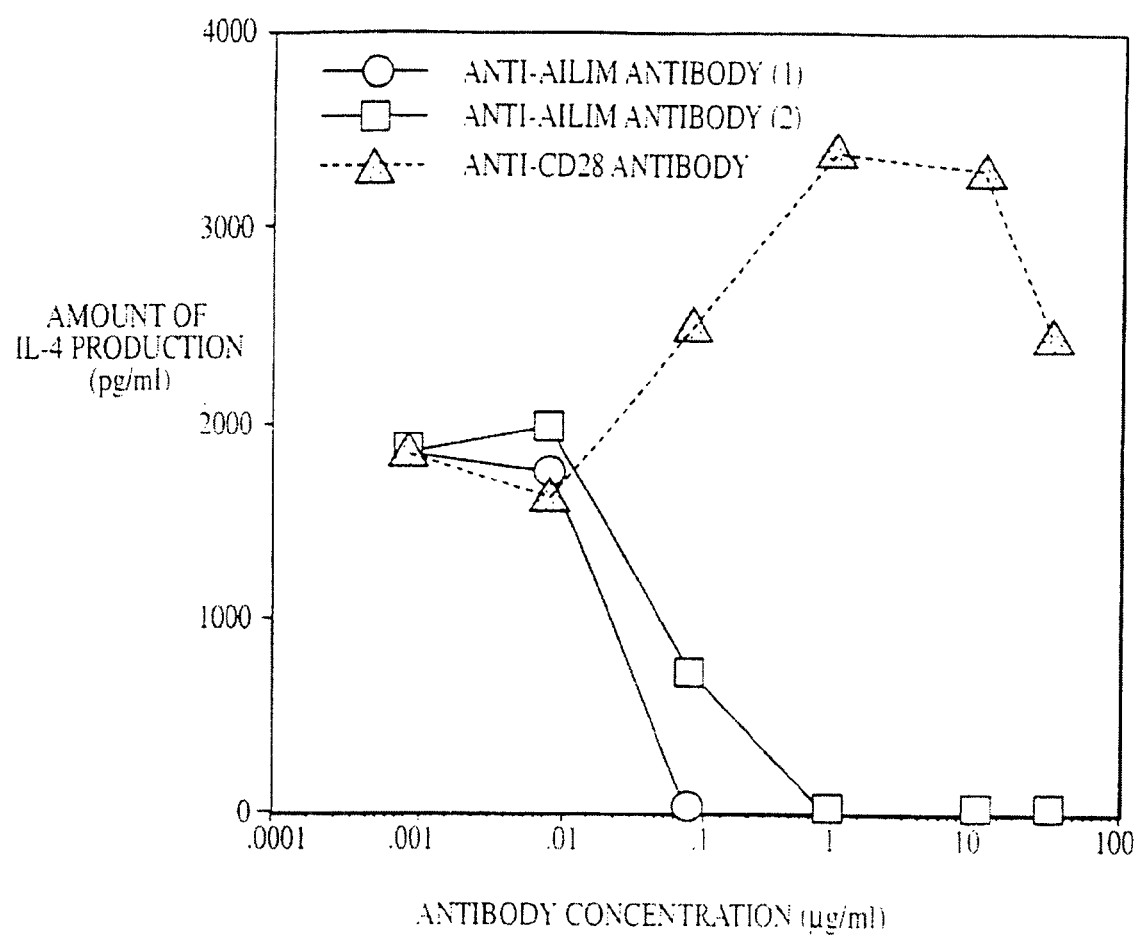

FIG. 12 shows the inhibitory effect of anti-AILIM antibody on the increased production of IL-4, one of the T-cell responses, in human peripheral blood-derived T cells activated by stimulating with anti-CD3 antibody.

Figure 13:
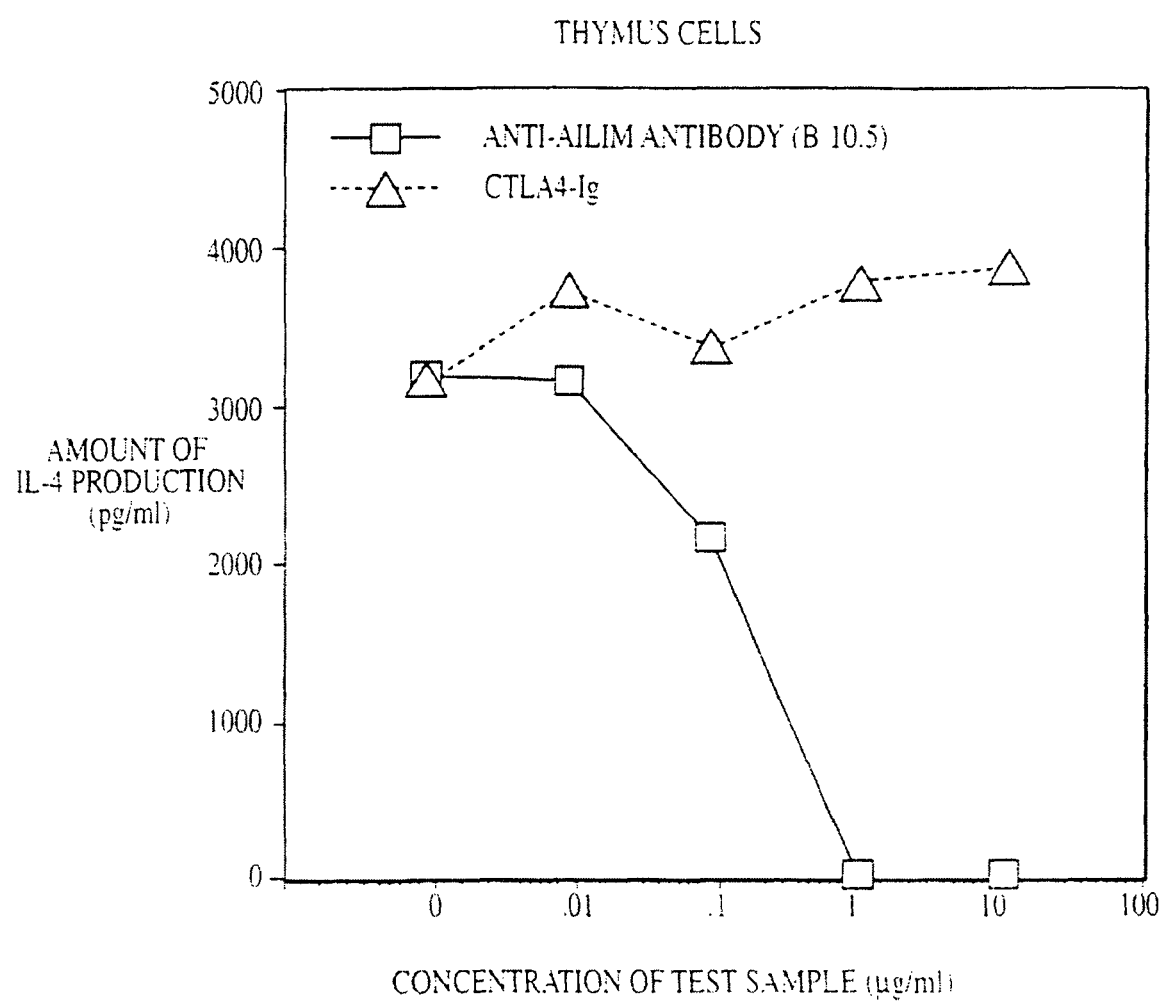

FIG. 13 shows the inhibitory effect of anti-AILIM antibody on the increased production of IL-4, one of the T-cell responses, in mouse thymus-derived T cells activated by stimulating with anti-CD3 antibody.

Figure 14:
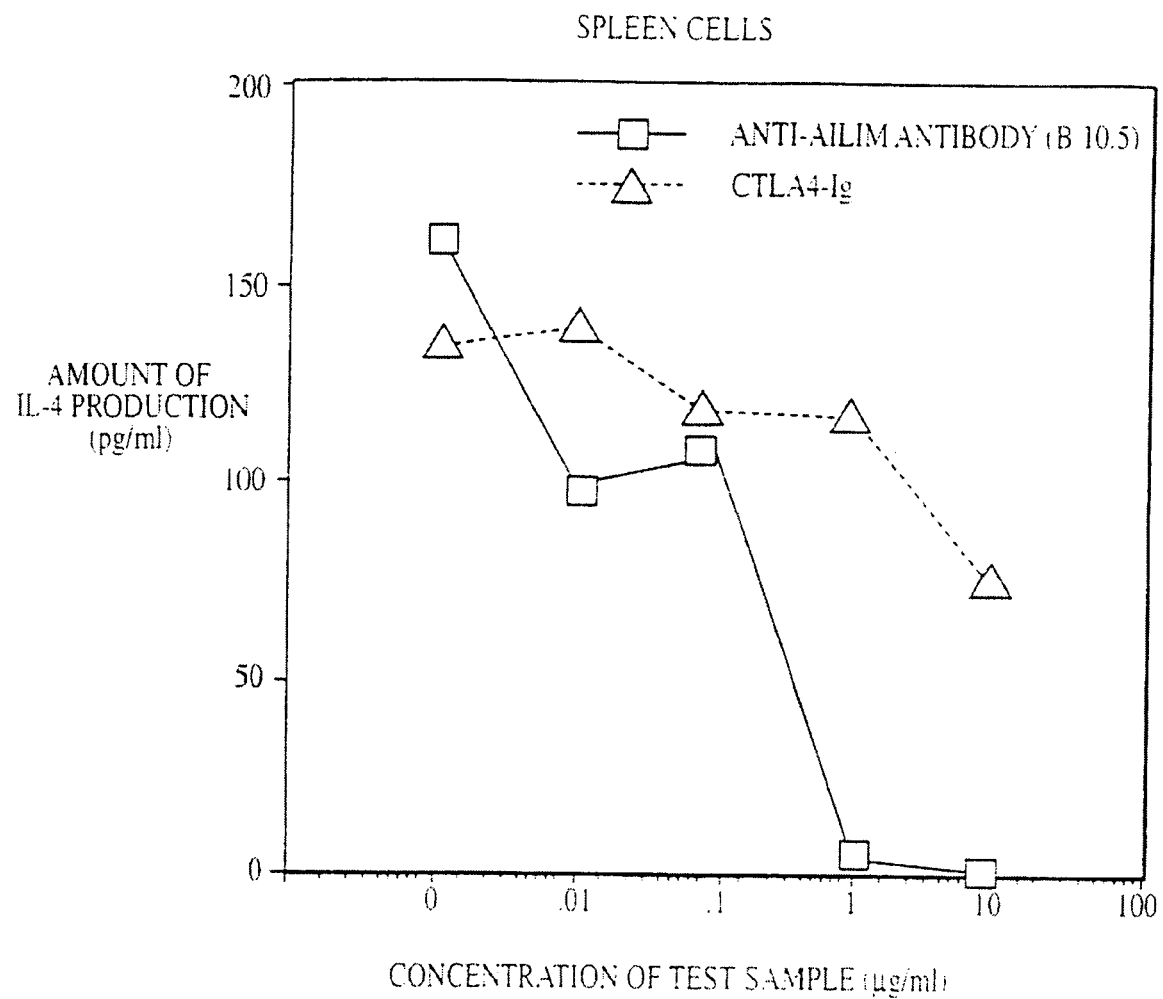

FIG. 14 shows the inhibitory effect of anti-AILIM antibody on the increased production of IL-4, one of the T-cell responses, in mouse spleen-derived T cells activated by stimulating with anti-CD3 antibody.

Figure 15:
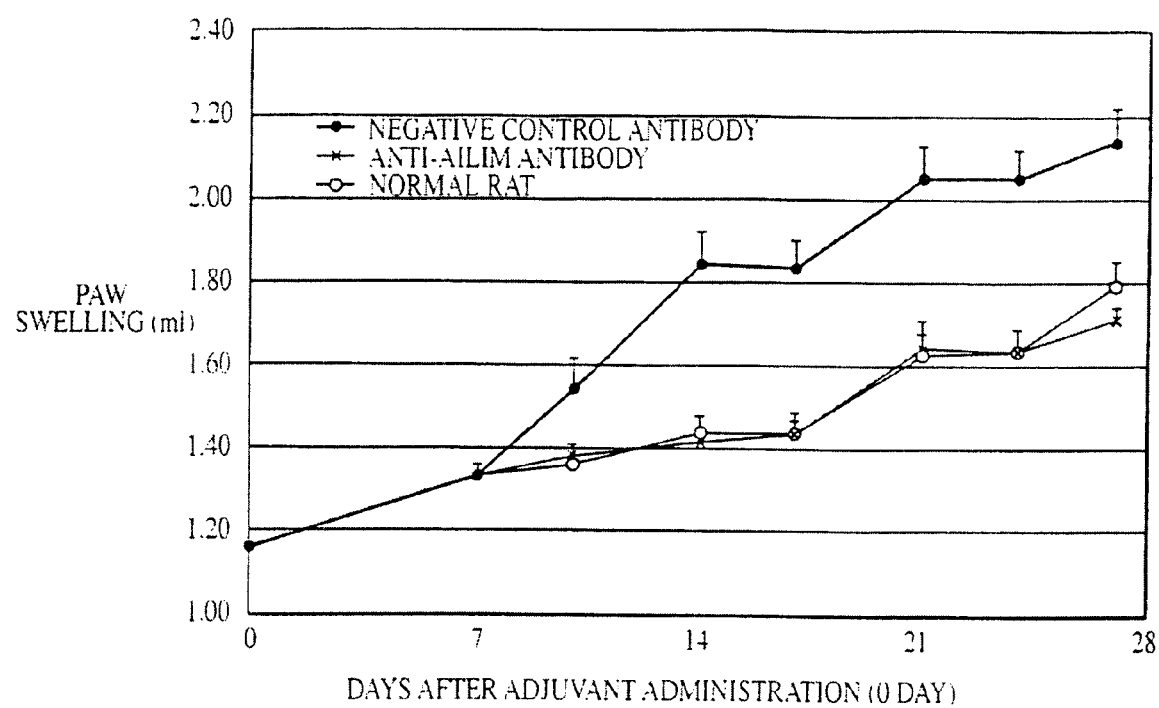

FIG. 15 shows the therapeutic effect on paw swelling which is a parameter of arthrosis in a host suffering from arthrosis by administering anti-AILIM antibody several times.

Figure 16A:
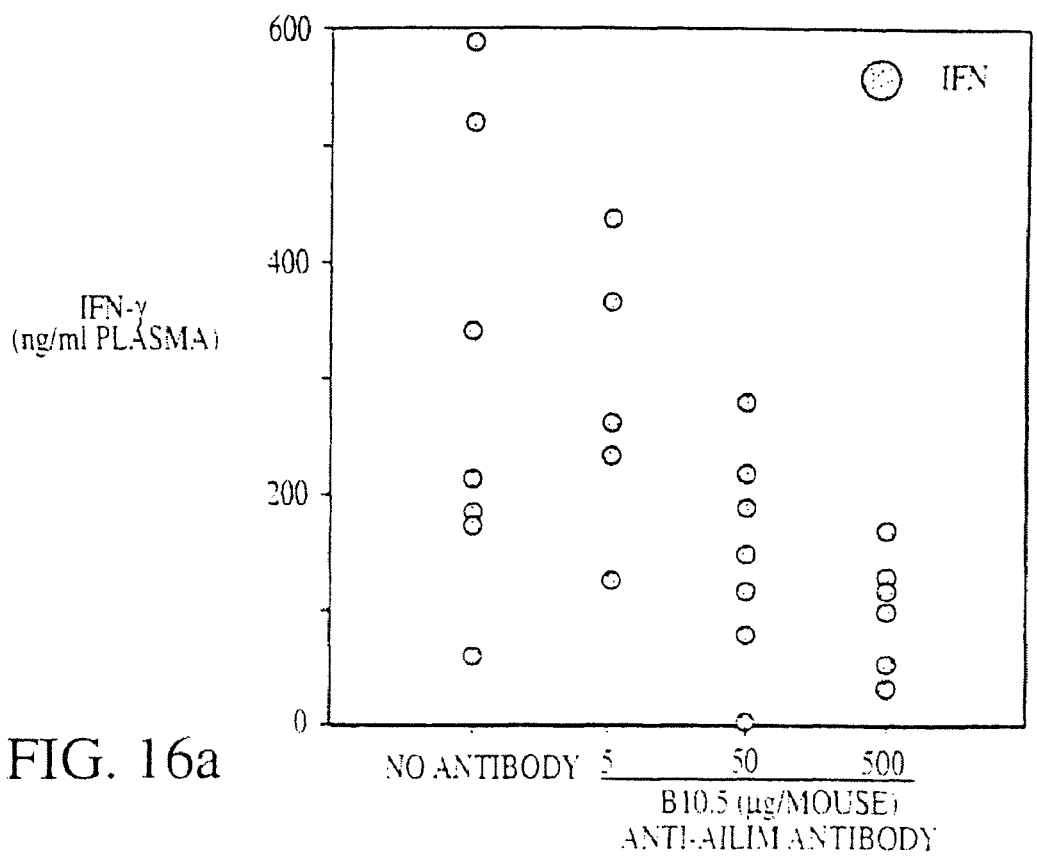
Figure 16B:
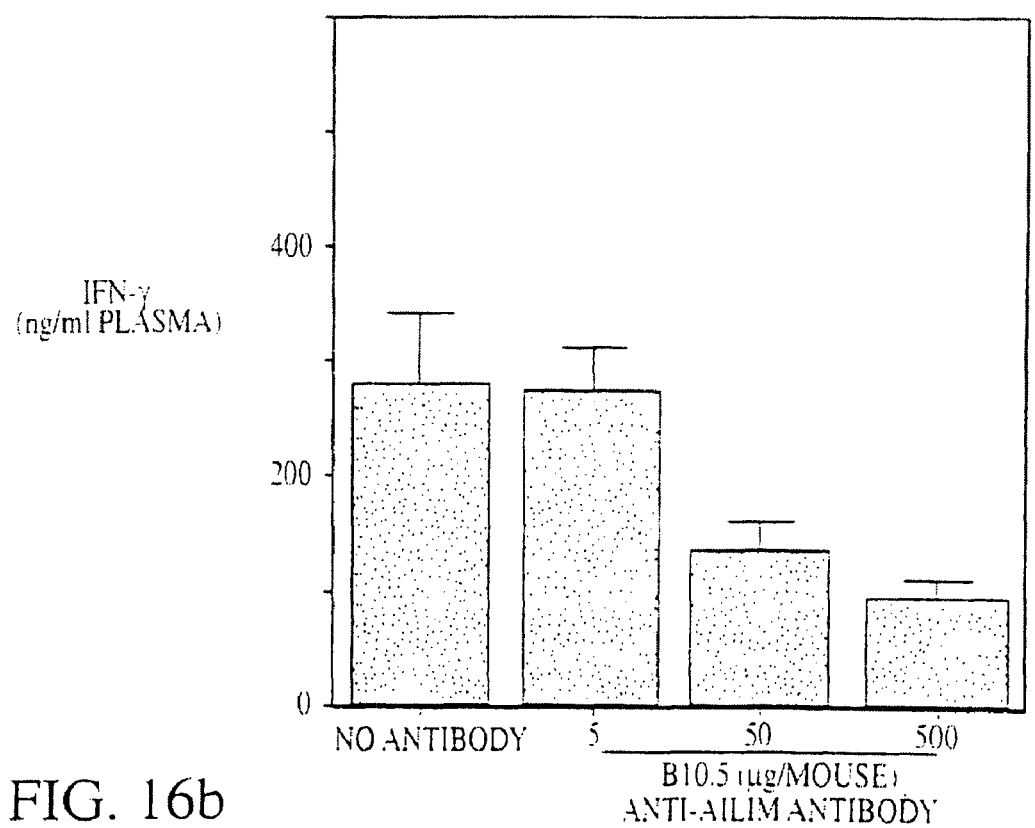

FIG. 16 shows the therapeutic effect of anti-AILIM antibody on increased production of IFNγ which is a parameter for the worsen condition in a host suffering from hepatitis.

Figure 17A:
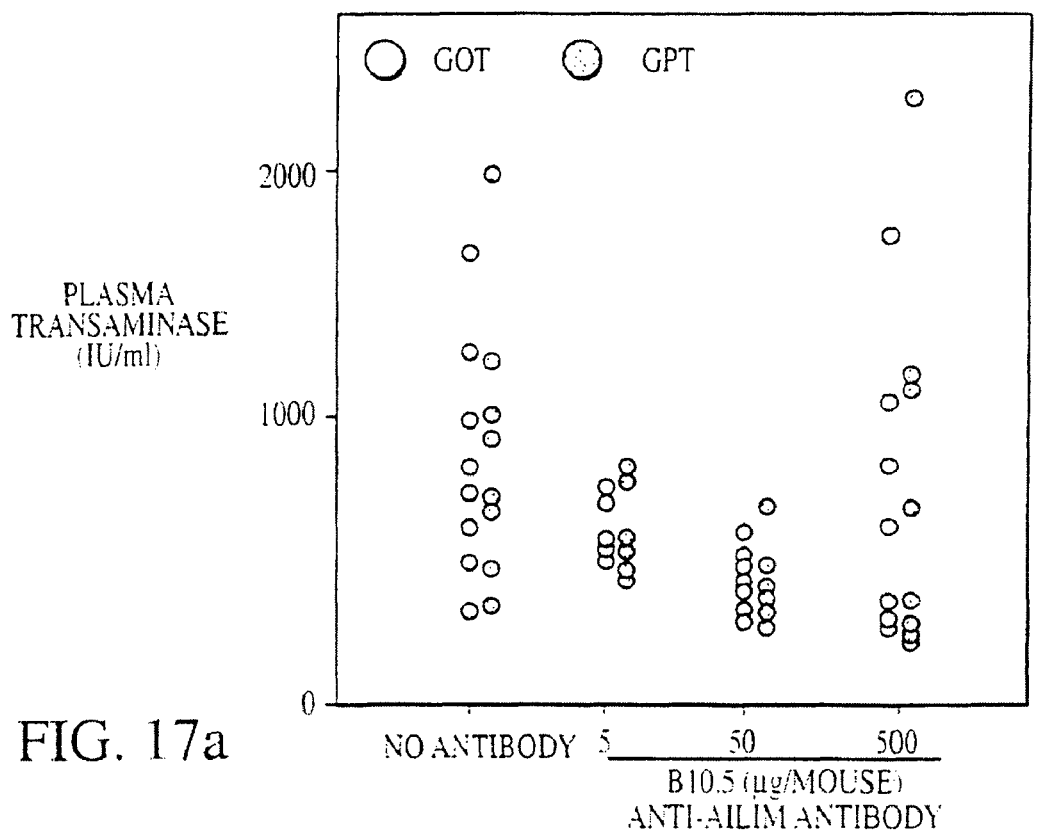
Figure 17B:
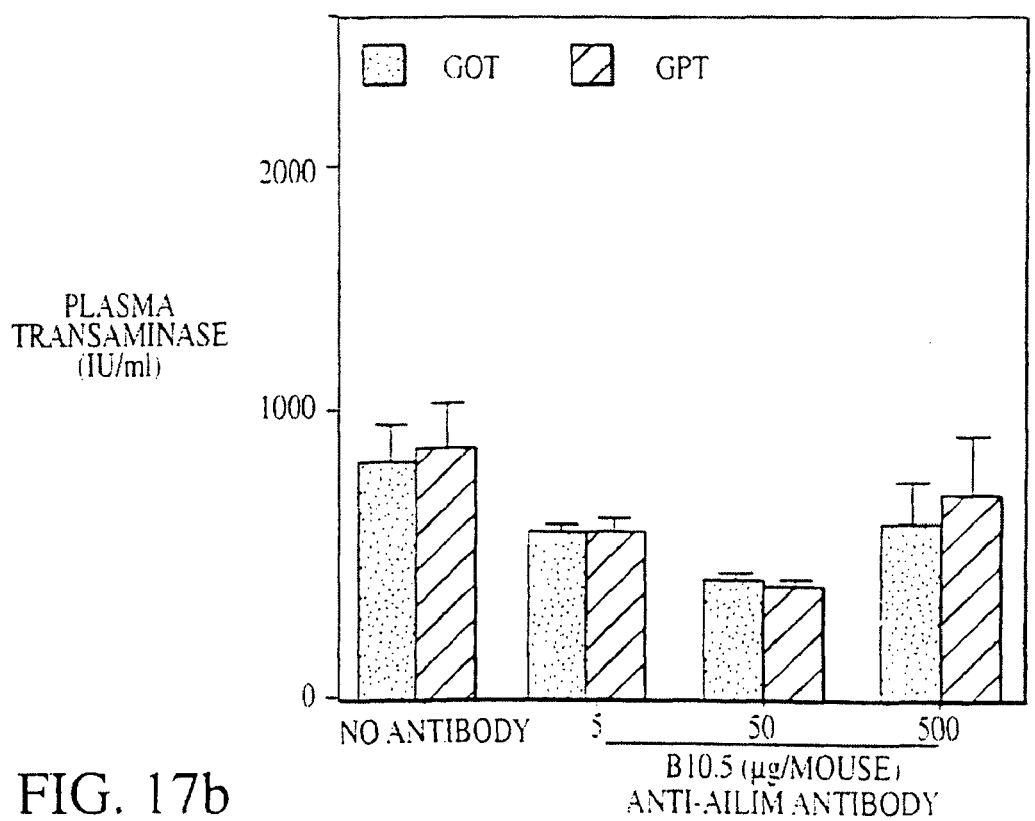

FIG. 17 shows the inhibitory effect of anti-AILIM antibody on increased production of GPT and GOT which are a parameter for the worsen condition in a host suffering from hepatitis.

Figure 18:
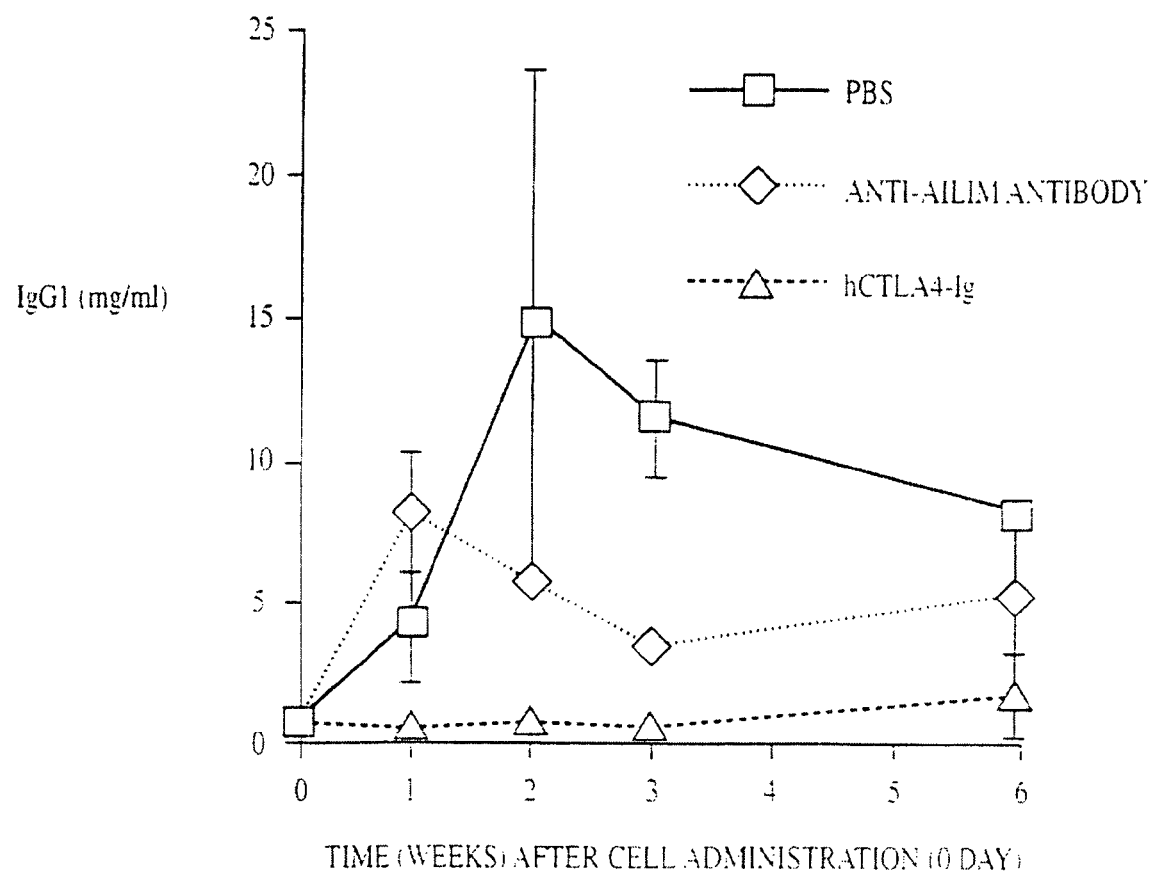

FIG. 18 shows the inhibitory effect of anti-AILIM antibody on increased production of IgG which is one of graft versus host reactions (GVH reactions) in graft versus host disease (GVHD).

Figure 19:
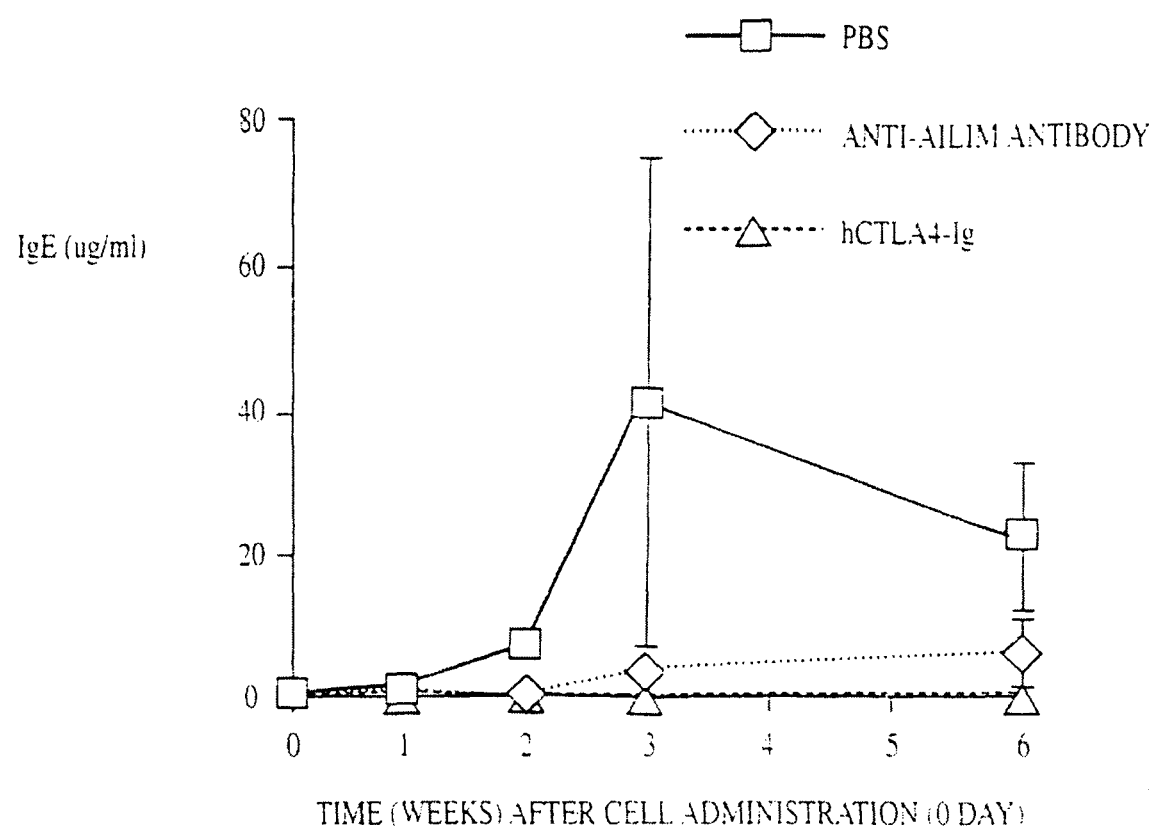

FIG. 19 shows the inhibitory effect of anti-AILIM antibody on increased production of IgE which is one of graft versus host reactions (GVH reactions) in graft versus host disease (GVHD).

Figure 20:
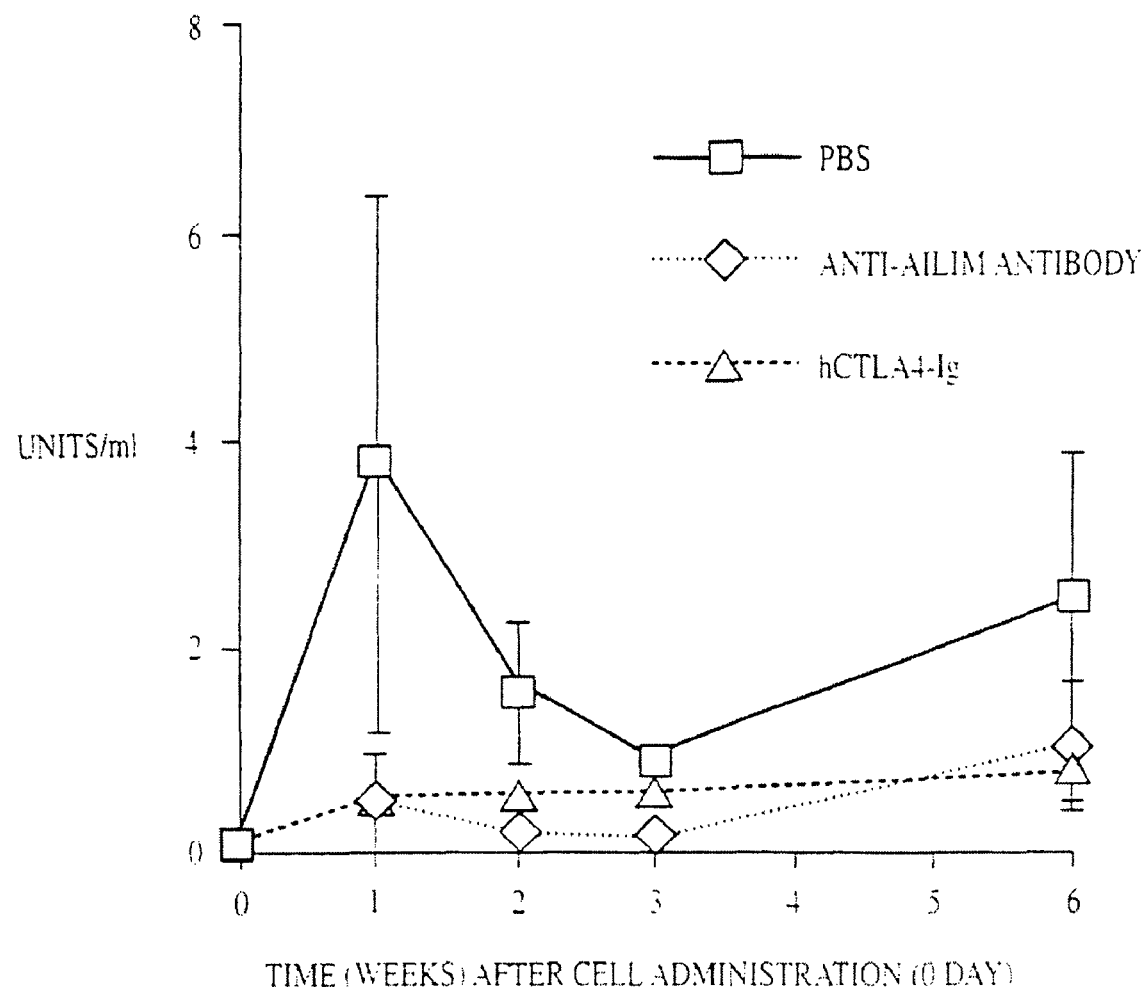

FIG. 20 shows the inhibitory effect of anti-AILIM antibody on increased anti-dsDNA antibody titer which is one of graft versus host reactions (GVH reactions) in graft versus host disease (GVHD).

Figure 21:
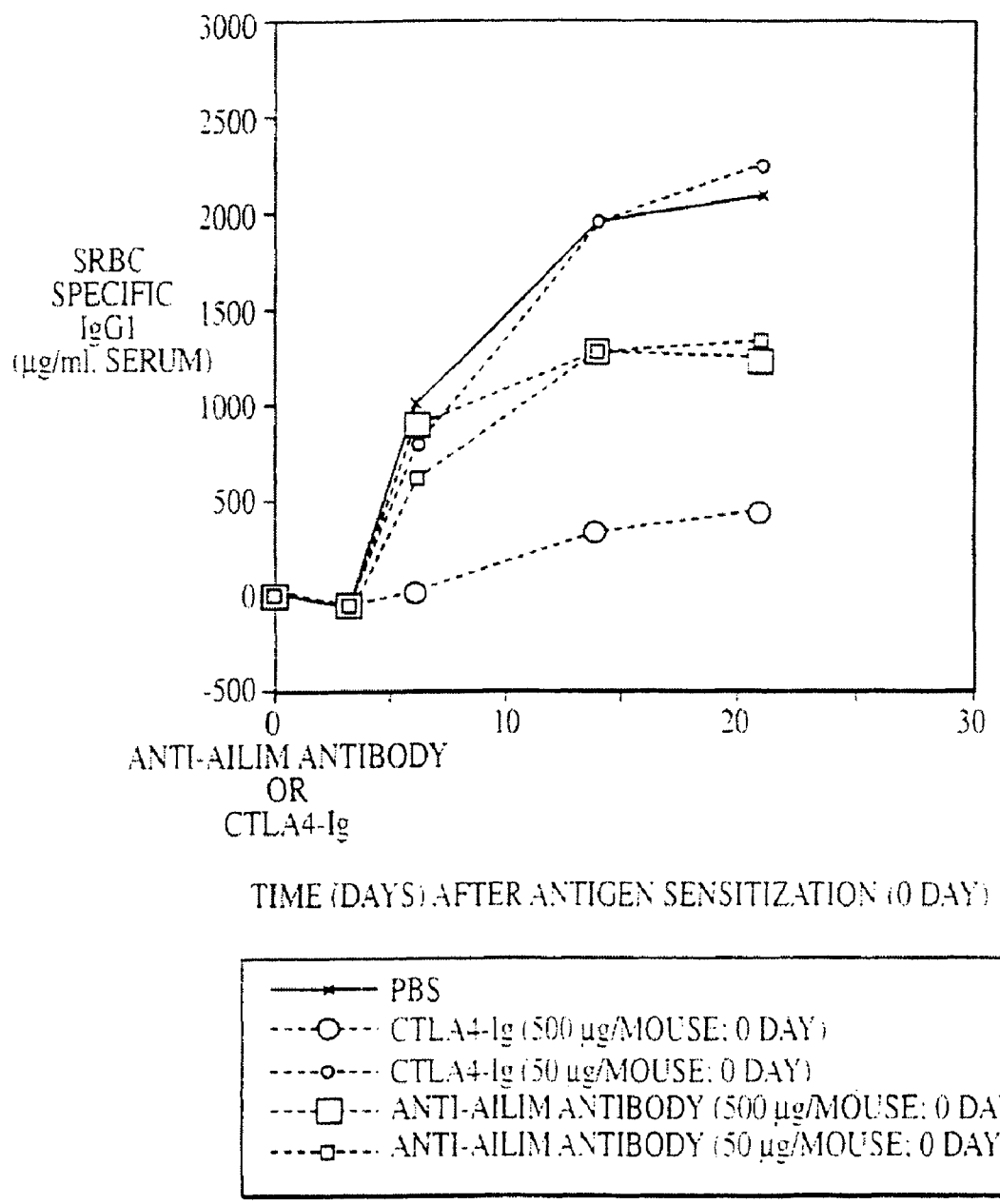

FIG. 21 shows the inhibitory effect of anti-AILIM antibody in vivo in a host immunized with SRBC which is a foreign antigen on production of an antibody (administered immediately after antigen sensitization) against the foreign antigen.

Figure 22:
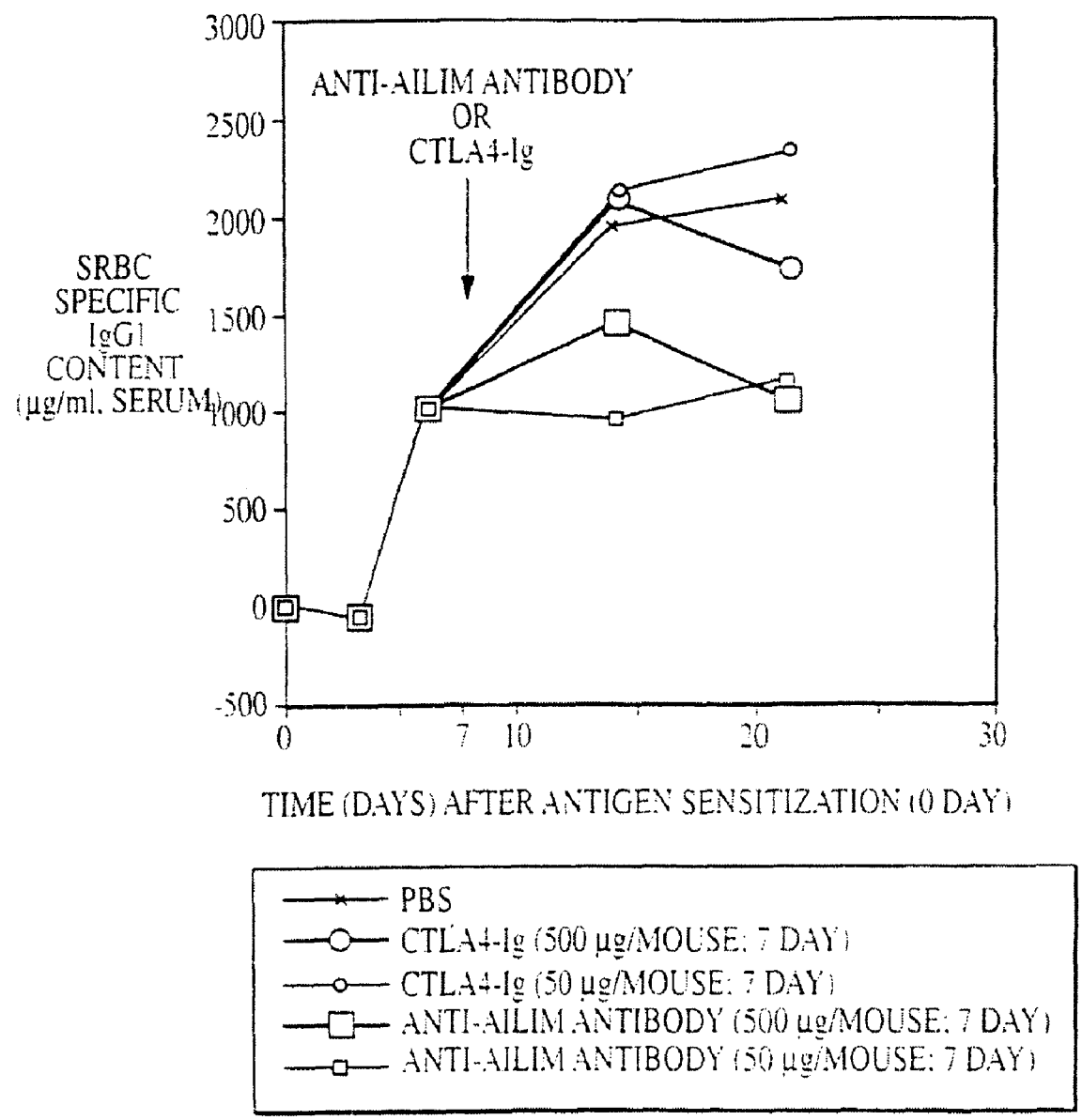

FIG. 22 shows the inhibitory effect of anti-AILIM antibody in vivo in a host sensitized with SRBC which is a foreign antigen on production of an antibody (administered 7 days after antigen sensitization) against a foreign antigen.

Figure 23:
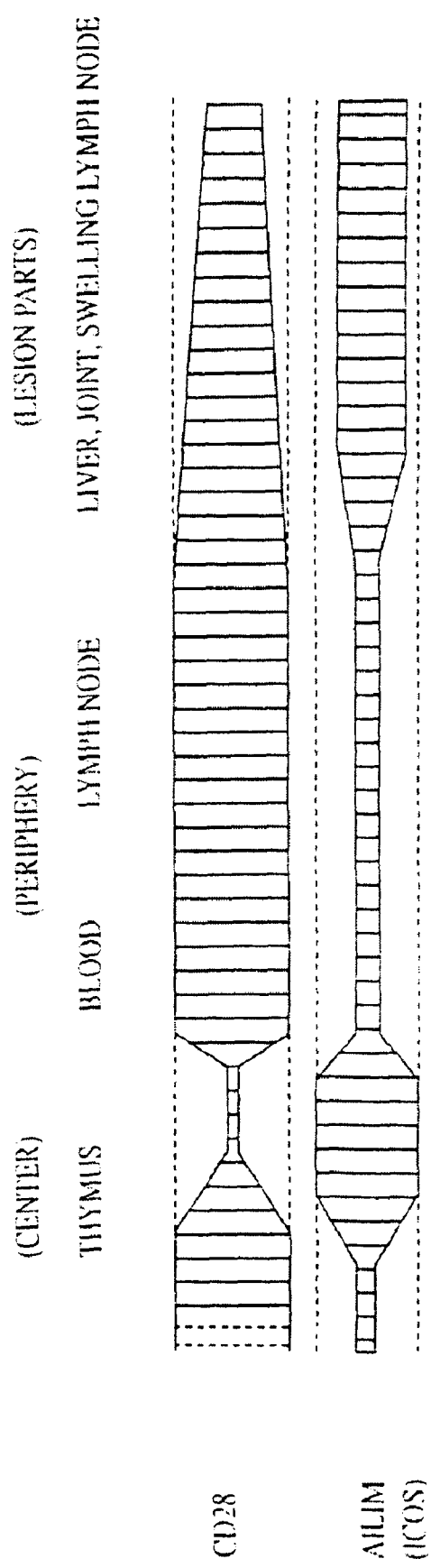
Figure 24A:
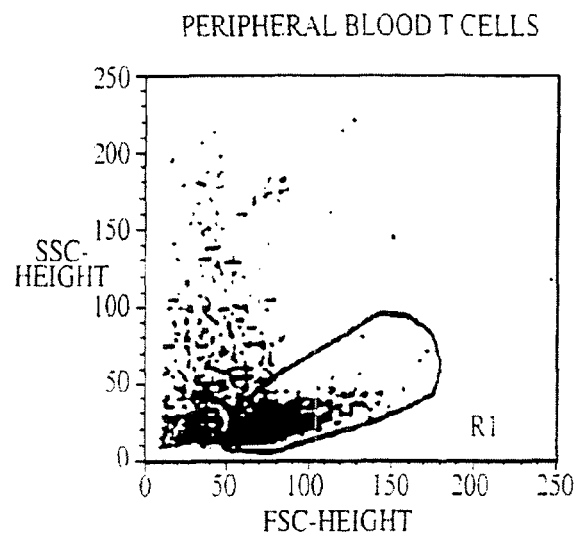
Figure 24B:
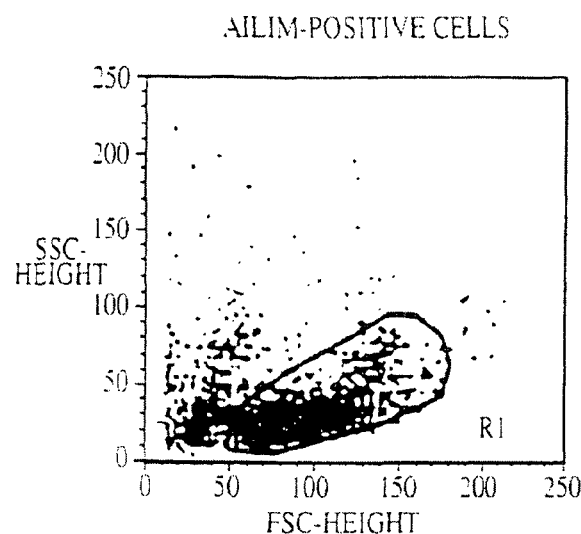
Figure 24C:
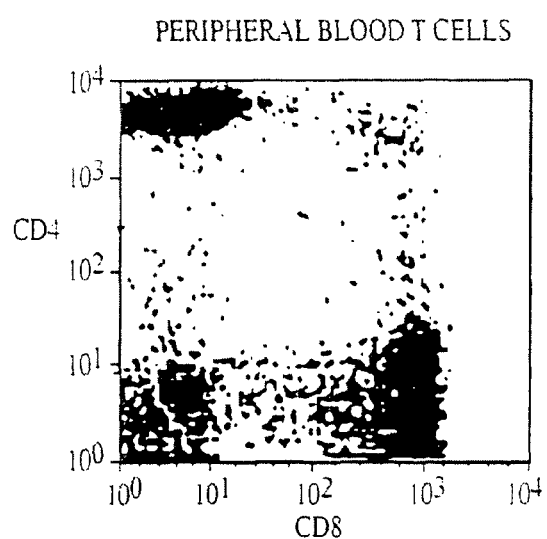
Figure 24D:
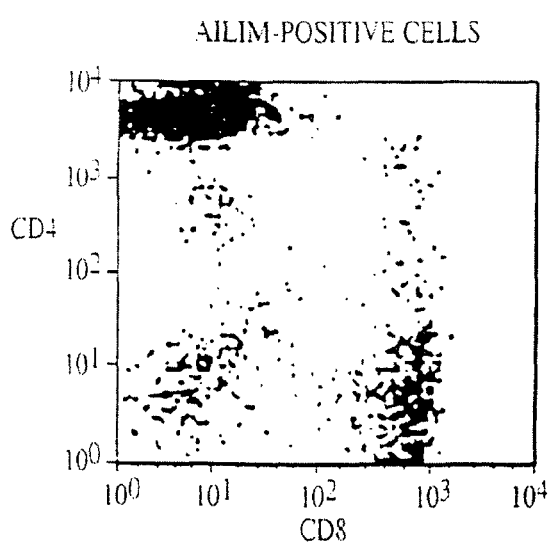
Figure 24E:
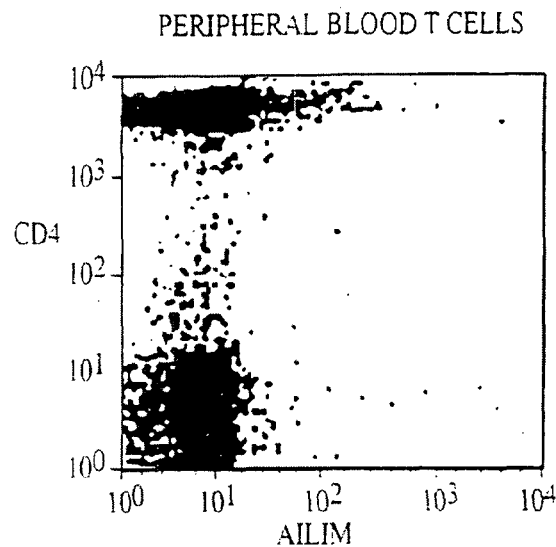
Figure 24F:
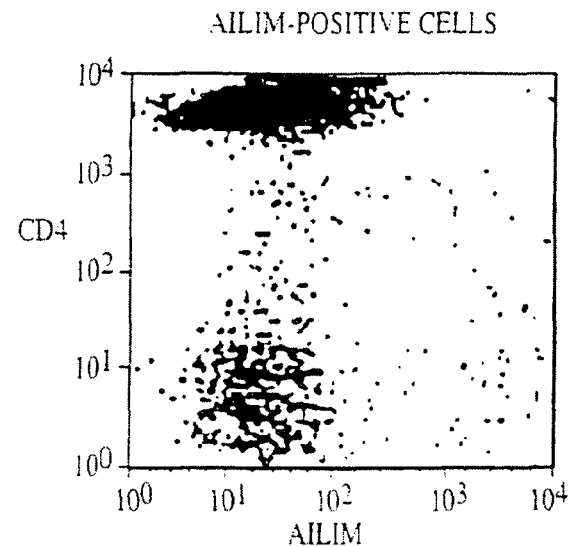
Figure 24G:
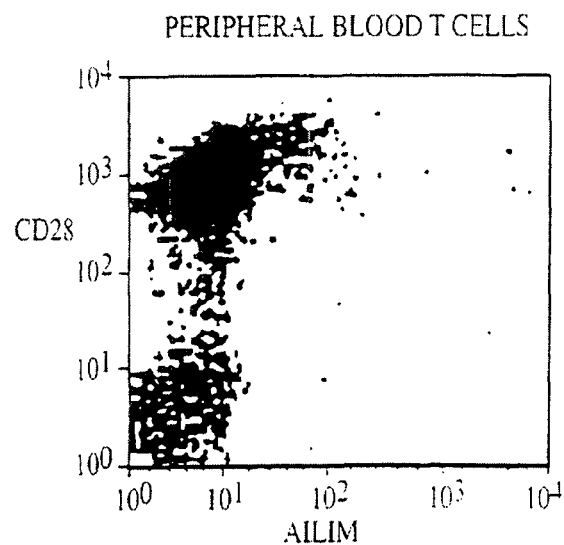
Figure 24H:
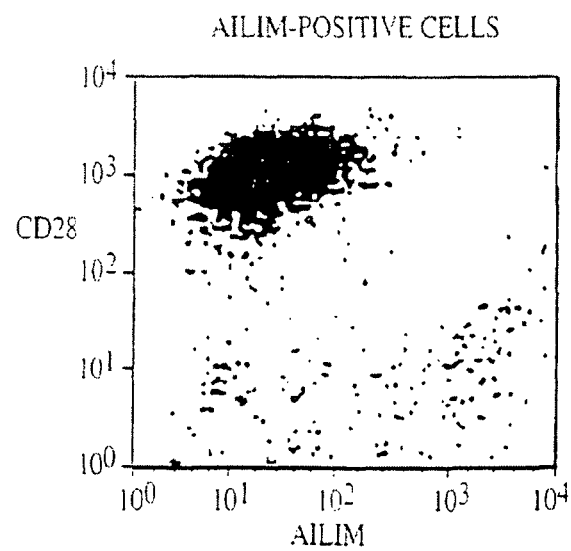
Figure 24I:
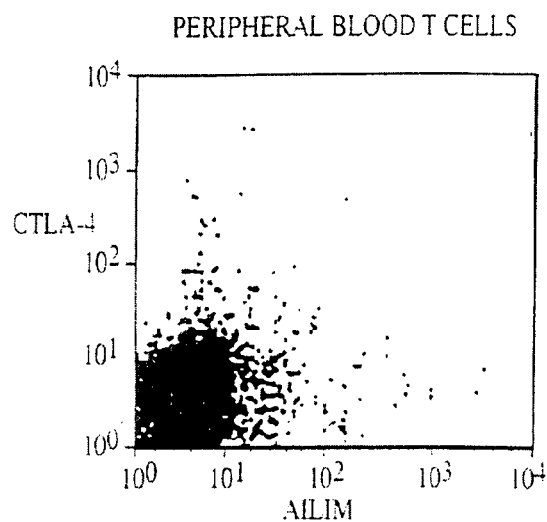
Figure 24J:
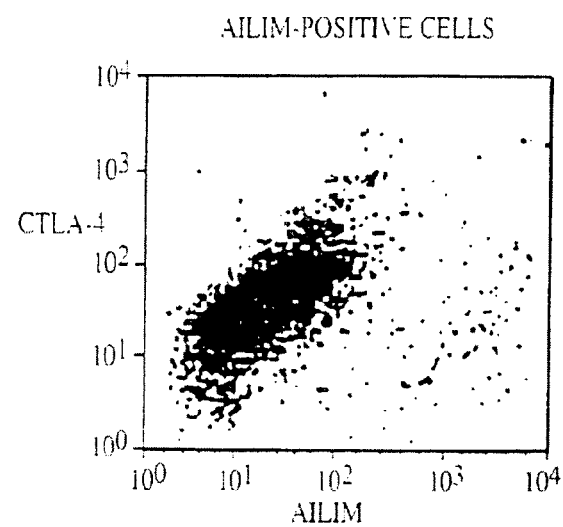
Figure 24K:
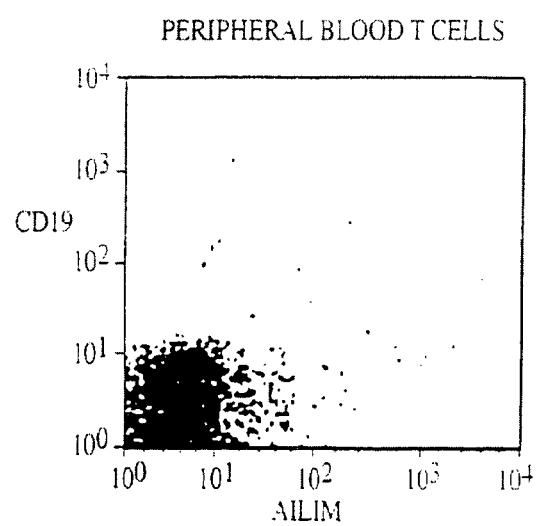
Figure 24L:
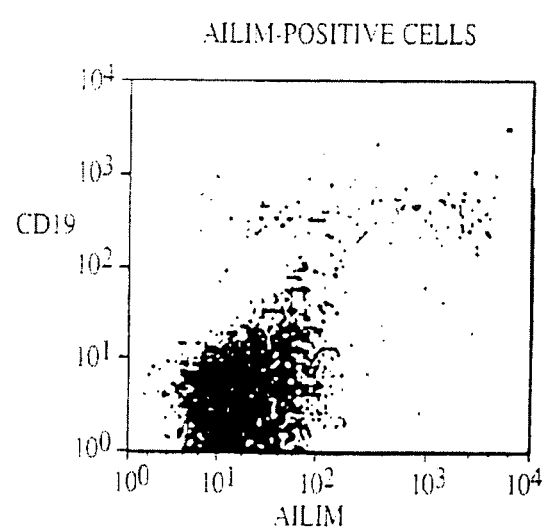

FIG. 23 schematically shows the expression pattern of AILIM and of CD28 in normal tissues (thymus, lymph node and peripheral blood) and lesion parts.

FIG. 24 shows the expression patterns for AILIM, CD28, CD4, CD8, CD19, and CTLA-4 in T cells derived from peripheral blood of a normal healthy person and in AILIM-positive cells separated from the T cells, respectively.

Sub figure (a) shows the distribution of various peripheral blood-derived T cells.

Sub figure (b) shows the distribution of AILIM-positive cells isolated from peripheral blood-derived T cells.

Sub figure (c) shows the expression pattern of CD4 and CD8 in peripheral blood-derived T cells.

Sub figure (d) shows the expression patterns of CD4 and CD8 in AILIM-positive cells separated from peripheral blood derived T cells.

Sub figure (e) shows the expression patterns of AILIM and CD4 in peripheral blood-derived T cells.

Sub figure (f) shows the expression patterns of AILIM and CD4 in AILIM-positive cells separated from peripheral blood-derived T cells.

Sub figure (g) shows the expression patterns of AILIM and CD28 in the peripheral blood-derived T cells.

Sub figure (h) shows the expression patterns of AILIM and CD28 in AILIM-positive cells separated from the peripheral blood-derived T cells.

Sub figure (i) shows the expression patterns of AILIM and CTLA-4 in the peripheral blood-derived T cells.

Sub figure (j) shows the expression patterns of AILIM and CTLA-4 in AILIM-positive cells separated from the peripheral blood-derived T cells.

Sub figure (k) shows the expression patterns of AILIM and CD19 in the peripheral blood-derived T cells.

Sub figure (l) shows the expression patterns of AILIM and CD19 in AILIM-positive cells separated from the peripheral blood-derived T cells.

Figure 25A:
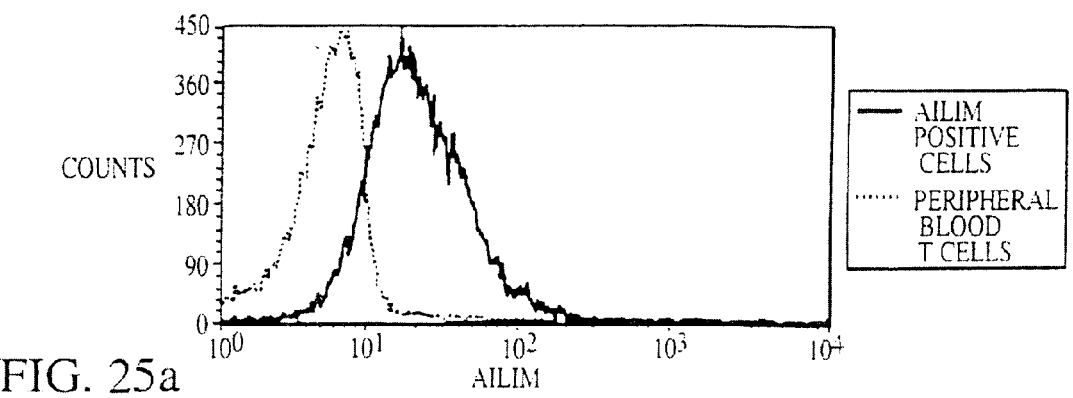
Figure 25B:
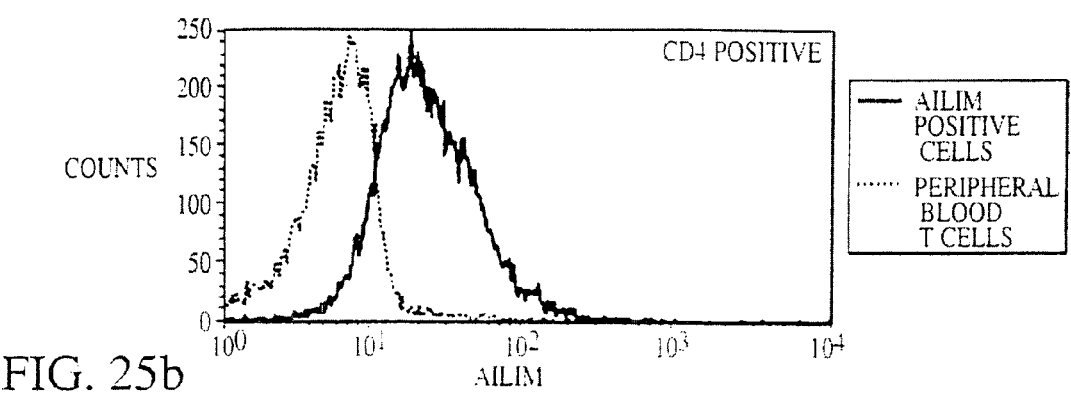
Figure 25C:
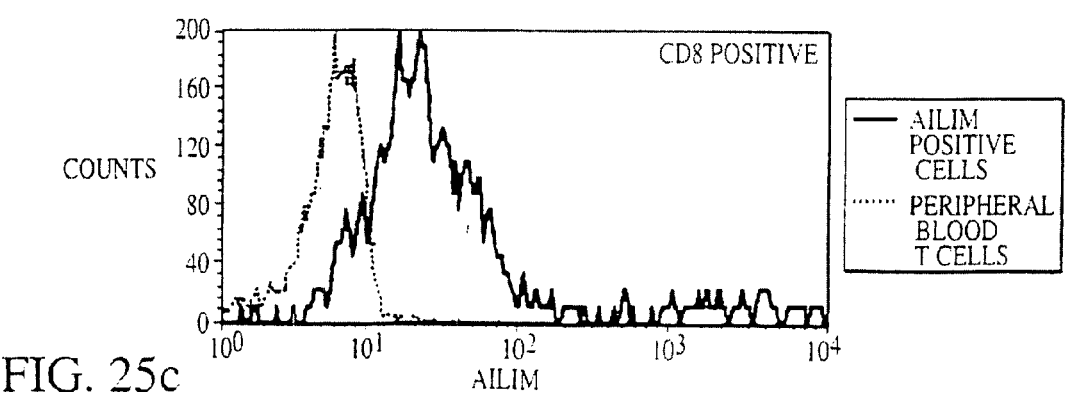

FIG. 25 shows strength of AILIM expression in T cells derived from peripheral blood of a normal healthy person, CD4-positive T cell, CD8-positive T cells, and each AILIM-positive cells separated from each of the T cells.

Sub figure (a) shows the strength of AILIM expression in peripheral blood T cells, and AILIM-positive cells separated from the T cells, respectively.

Sub figure (b) shows the strength of AILIM expression in peripheral blood CD4 positive T cells, and CD4-positive AILIM-positive T cells separated from the T cells, respectively.

Sub figure (c) shows the strength of AILIM expression in peripheral blood CD8 positive T cells, and CD8-positive AILIM-positive T cells separated from the T cells, respectively.

Figure 26A:
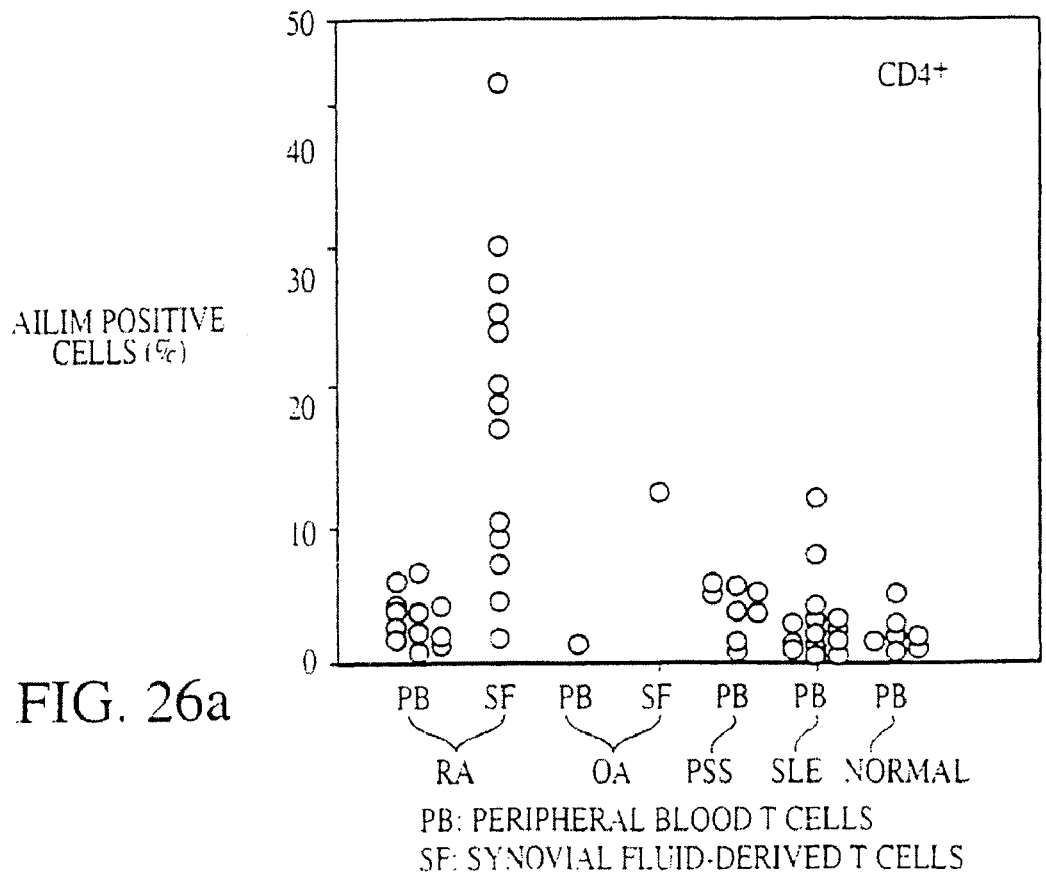
Figure 26B:
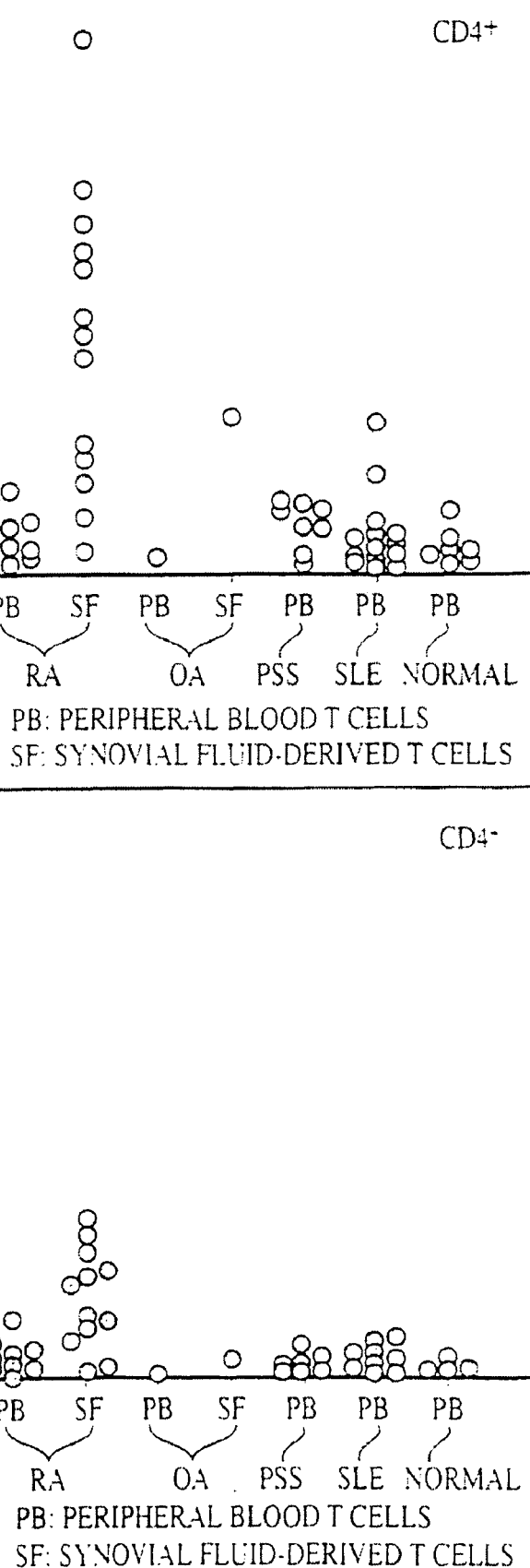
Figure 27:
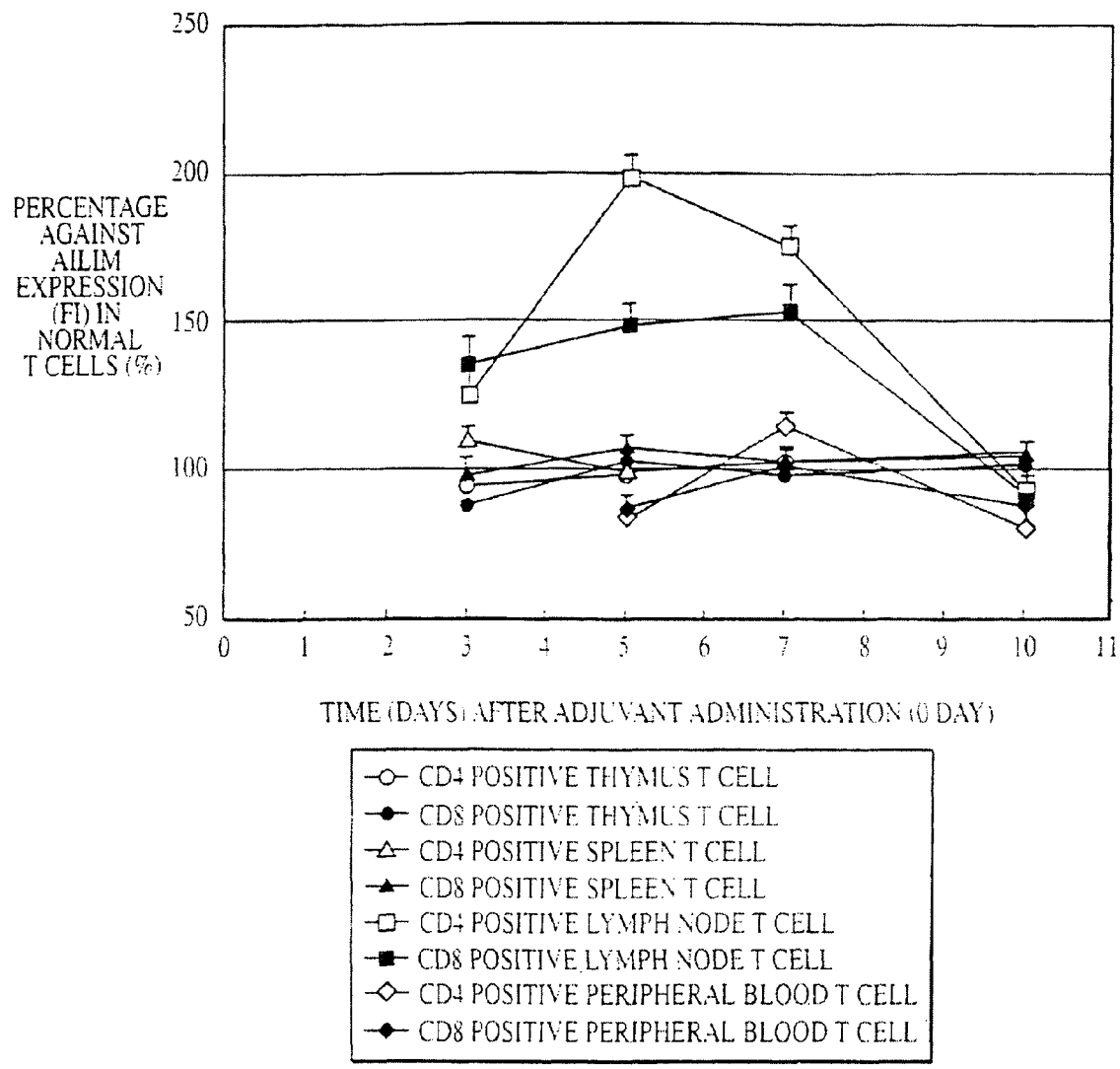
Figure 28A:
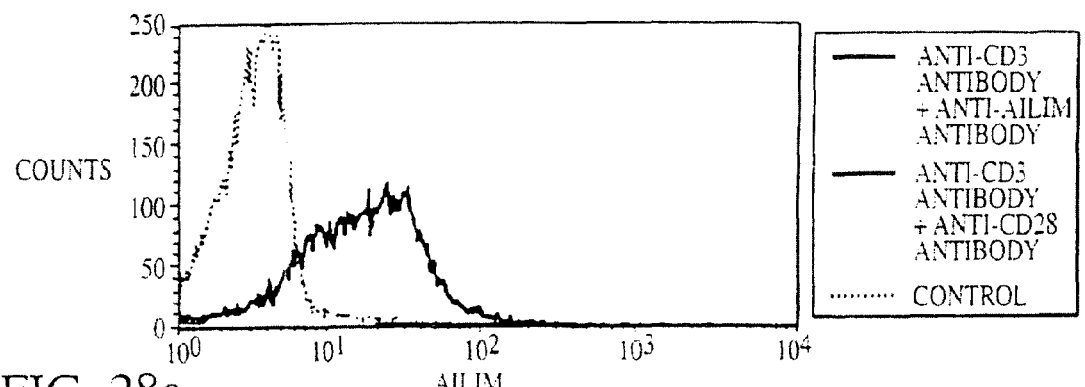
Figure 28B:
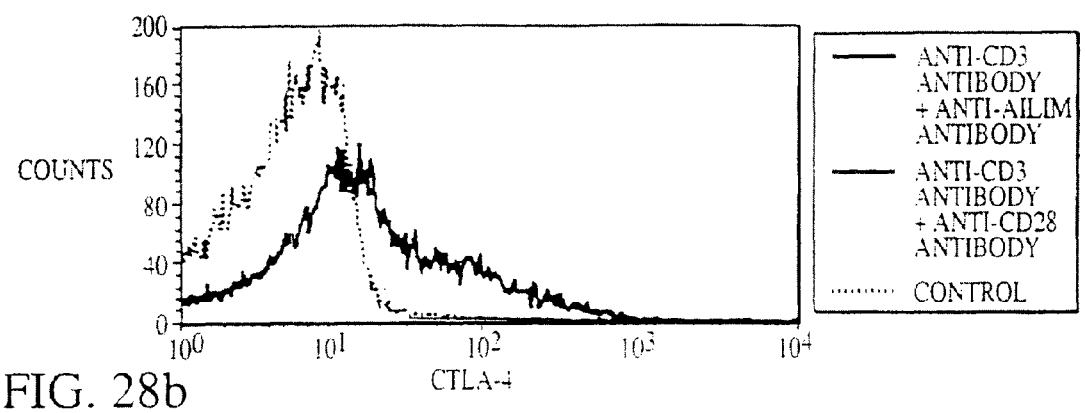
Figure 28C:
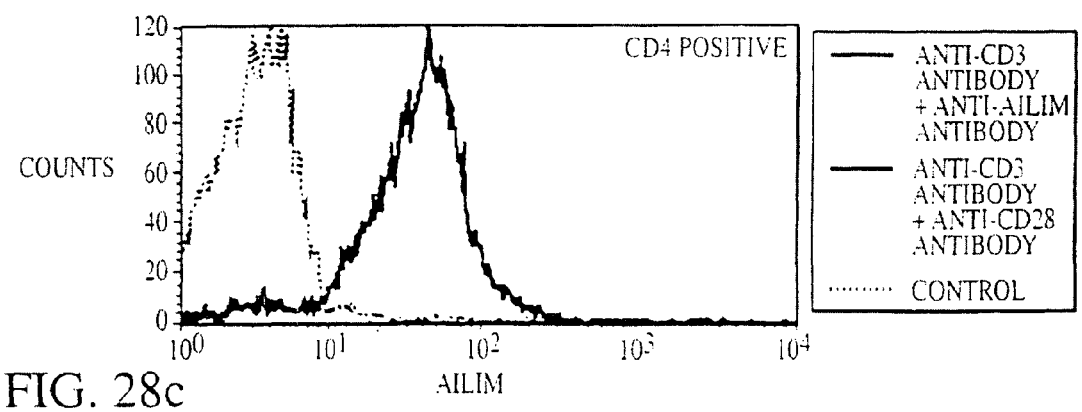
Figure 28D:
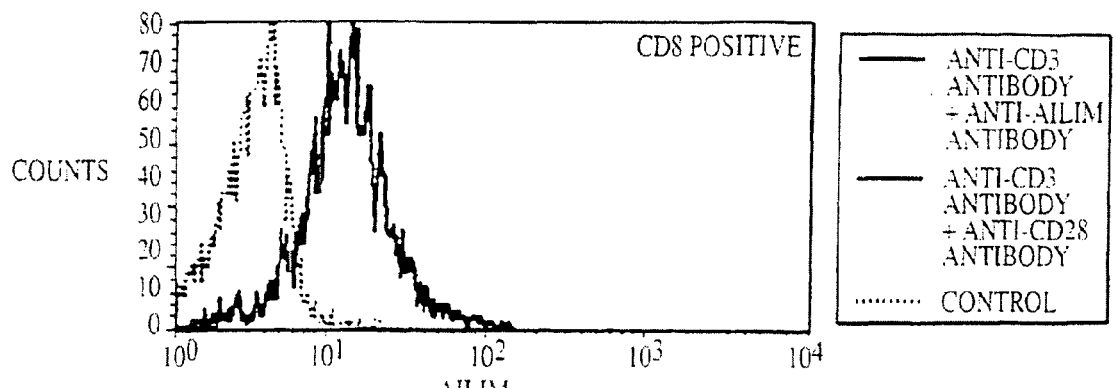
Figure 28E:
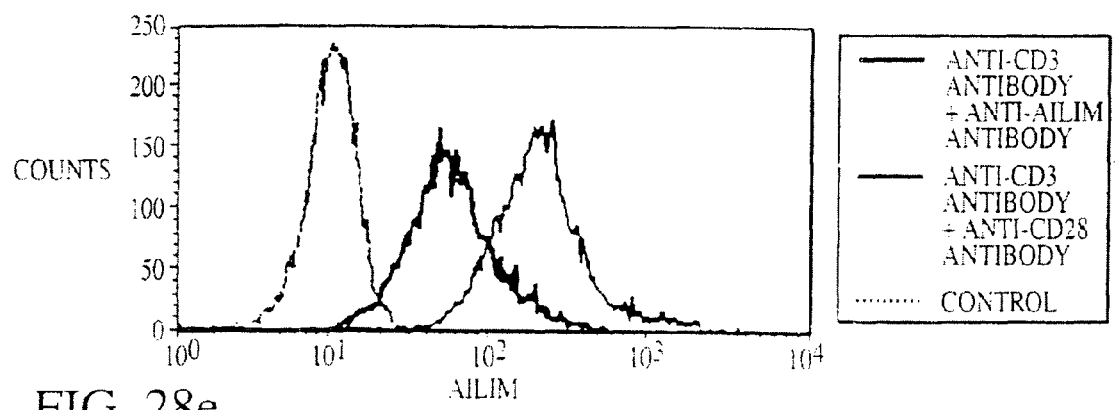
Figure 28F:
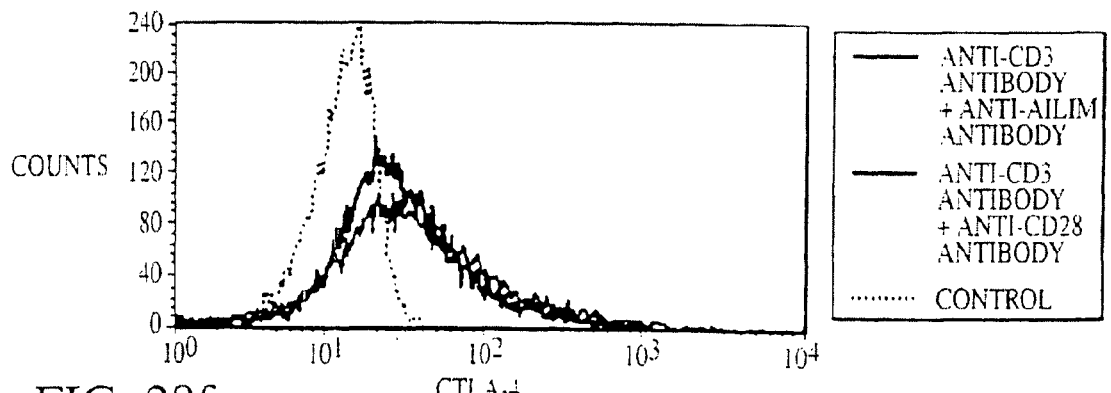
Figure 29A:
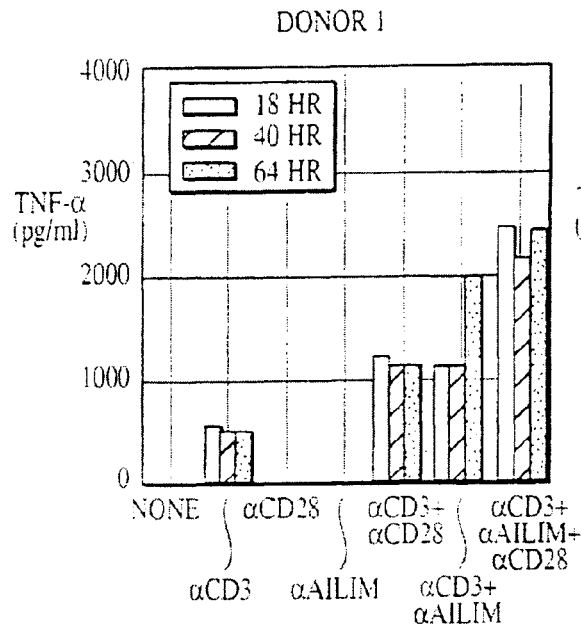
Figure 29B:
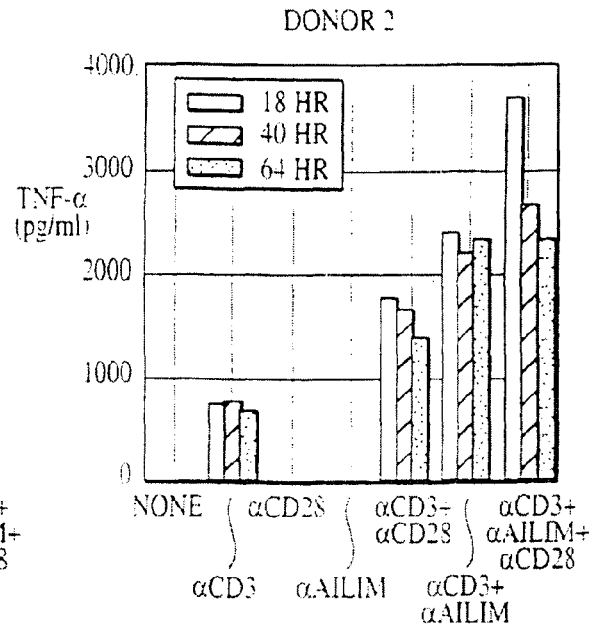
Figure 29C:
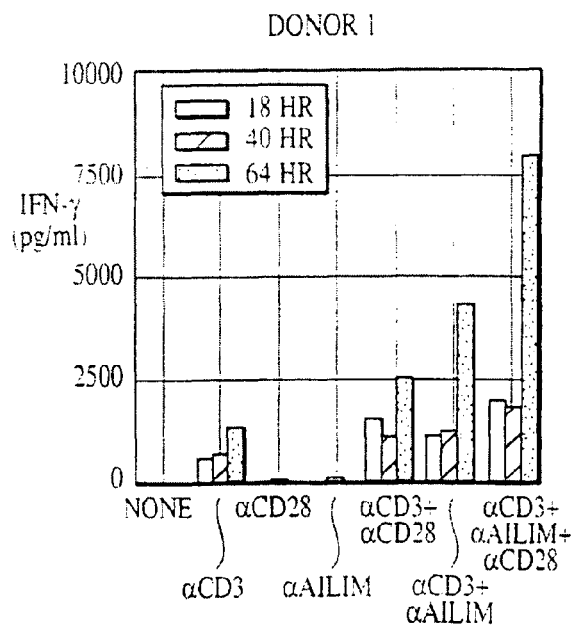
Figure 29D:
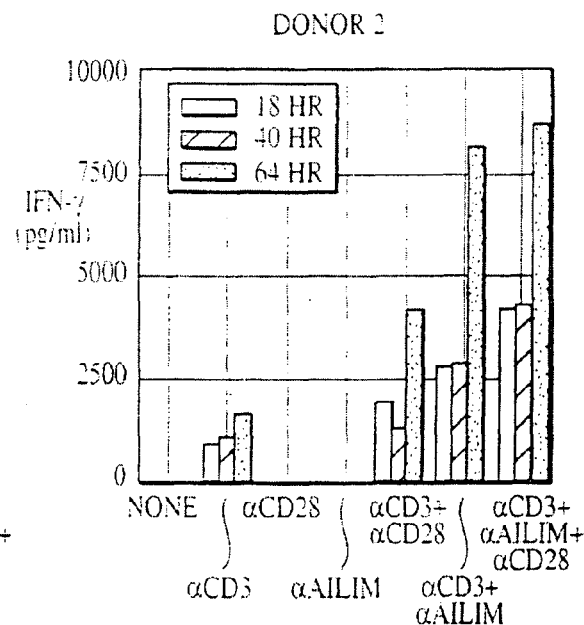
Figure 29E:
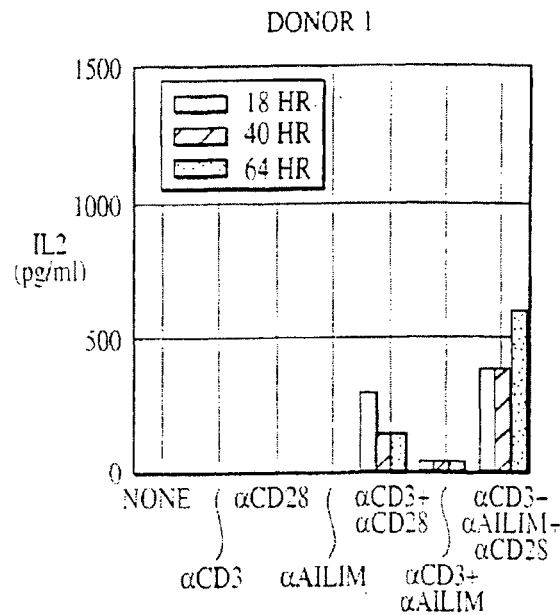
Figure 29F:
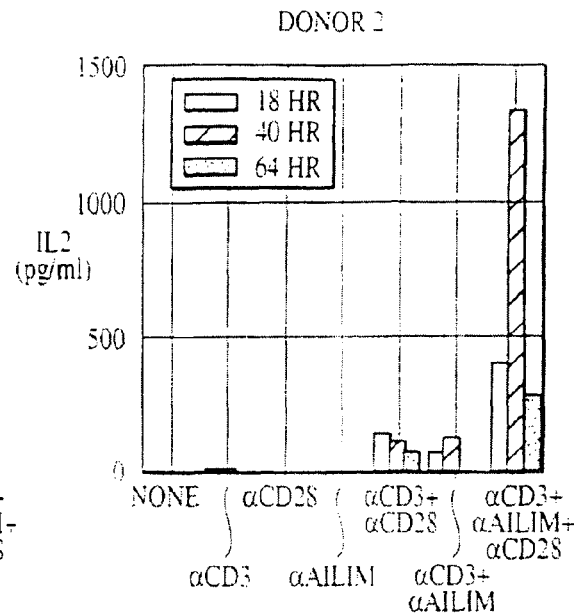
Figure 29G:
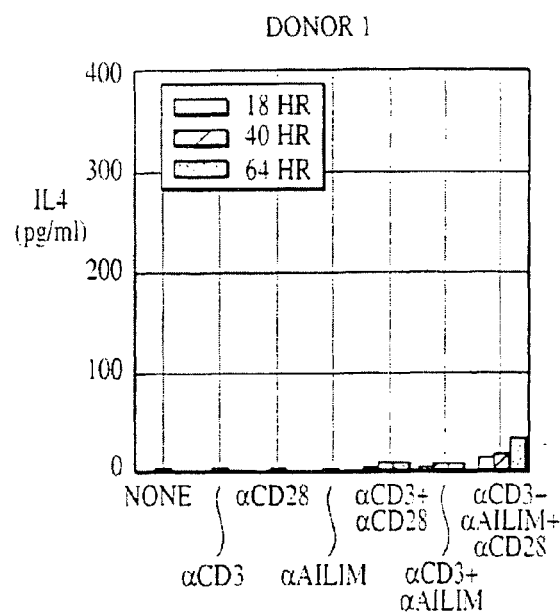
Figure 29H:
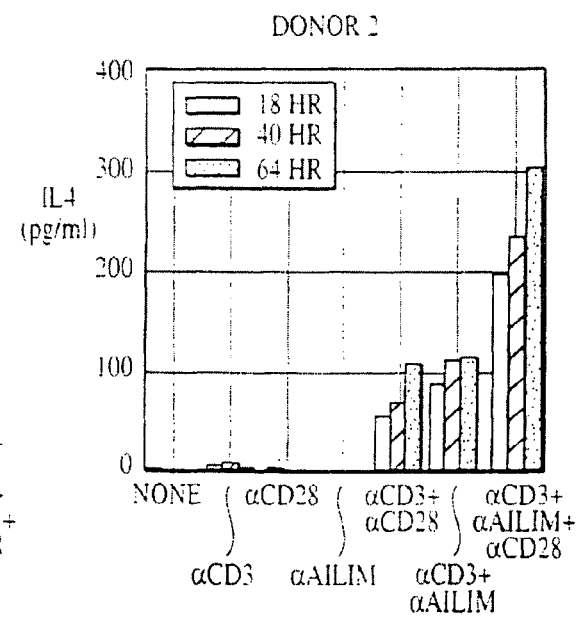
Figure 29I:
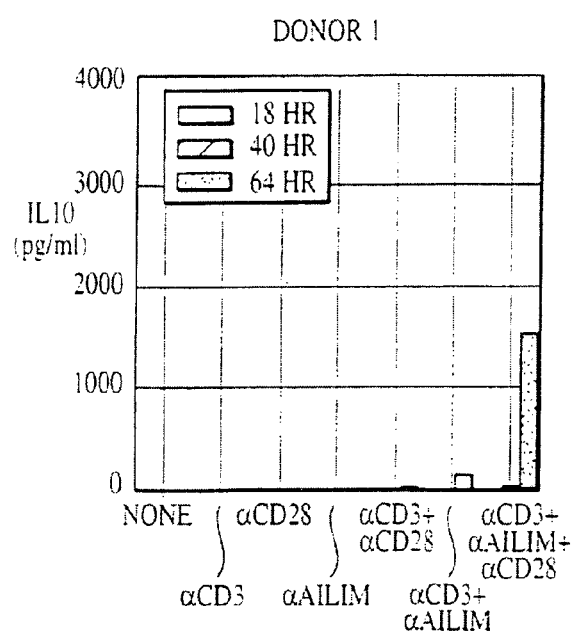
Figure 29J:
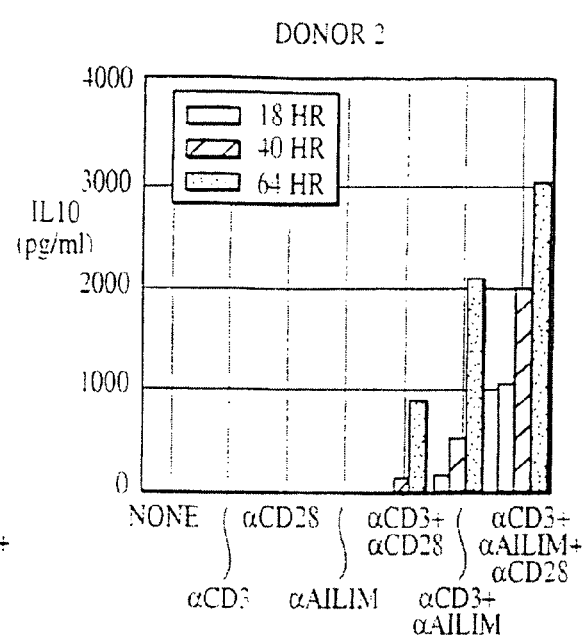

FIG. 26 shows the expression patterns of AILIM in peripheral blood-derived T cells and synovial fluid-derived T cells from each patient suffering from chronic rheumatoid arthritis (RA) and osteoarthritis (OA), and in peripheral blood T cells from each patient suffering from progressive systemic sclerosis (scleroderma; PSS) and systemic lupus erythematosus (SLE), respectively FIG. 27 shows the expression patterns of AILIM in T cells (CD4-positive T cells, CD8-positive T cells) derived from each thymus, spleen, lymph node and peripheral blood in adjuvant-induced arthritis model rats.

FIG. 28 shows expression patterns of each AILIM and CTLA-4 in normal healthy person peripheral blood-derived T cells activated by various stimuli.

Sub figure (a) shows the expression strength of AILIM in T cells activated by stimulating with PMA and Ionophore.

Sub figure (b) shows the expression strength of CTLA-4 in T cells activated by stimulating with PMA and Ionophore.

Sub figure (c) shows the expression strength for AILIM in CD4-positive T cells activated by stimulating with PMA and Ionophore.

Sub figure (d) shows the expression strength for CTLA-4 in CD4-positive T cells activated by stimulating with PMA and Ionophore.

Sub figure (e) shows the expression strength of AILIM in T cells activated by stimulating with either anti-CD3 antibody and anti-AILIM antibody or anti-CD3 antibody and anti-CD28 antibody.

Sub figure (f) shows the expression strength of CTLA-4 in T cells activated by stimulating with either anti-CD3 antibody and anti-AILIM antibody or anti-CD3 antibody and anti-CD28 antibody.

FIG. 29 shows the induction of production of various cytokines from each human peripheral blood T cell by stimulating with various antibodies.

Figure 30:
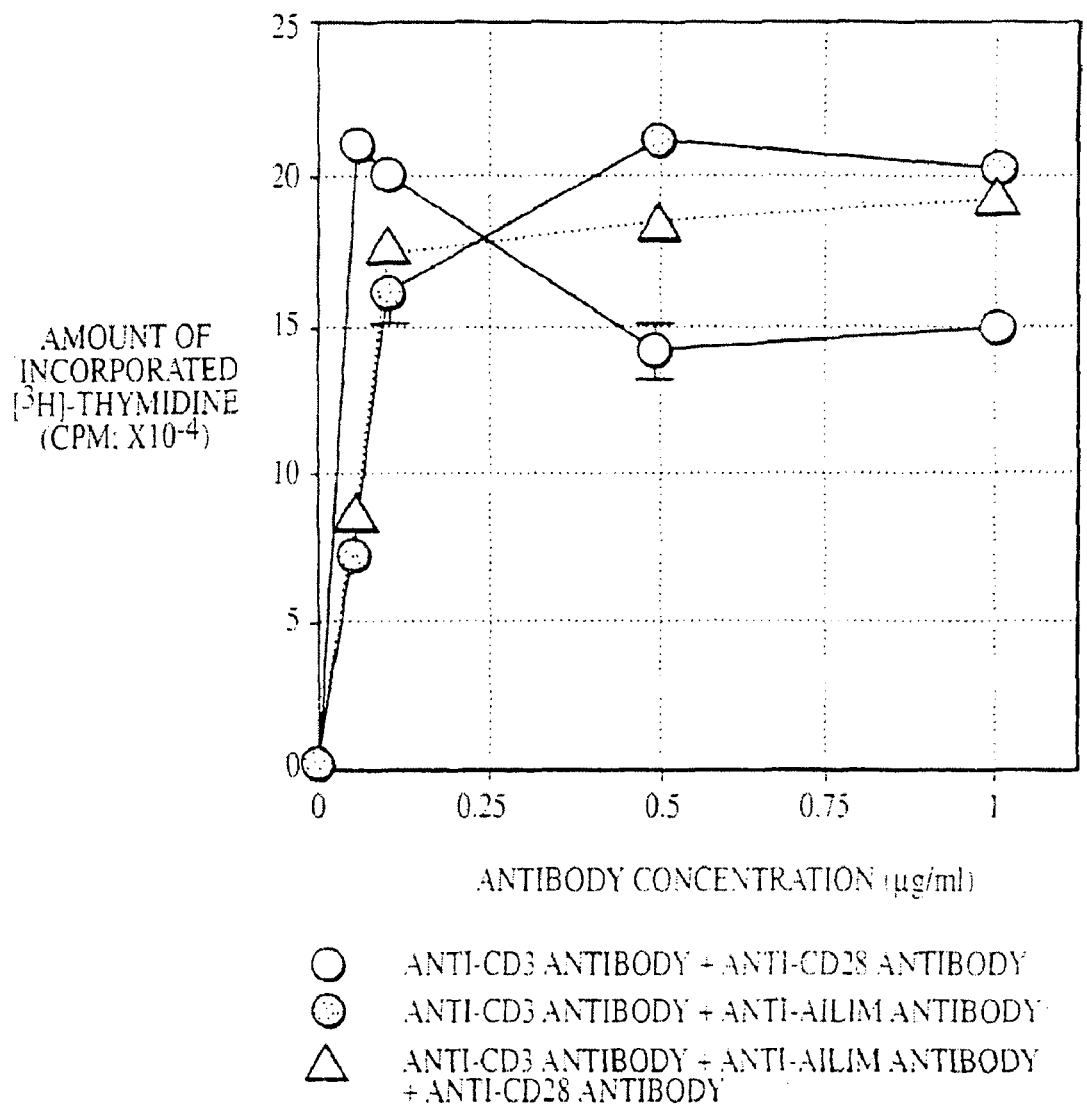

FIG. 30 shows induction of cell proliferation of each human peripheral blood T cell by stimulating with various antibodies at the various concentrations.

Figure 31:
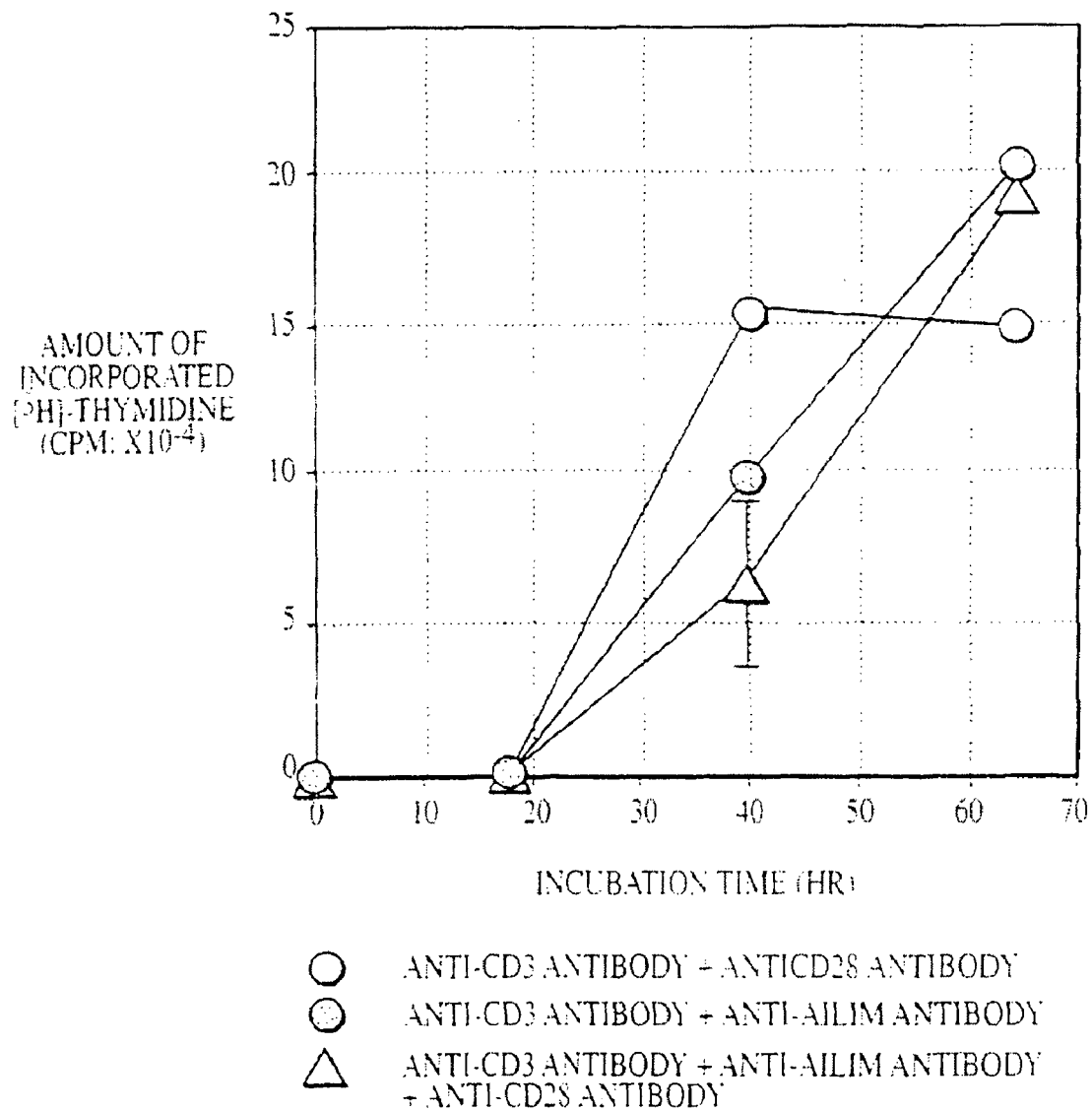

FIG. 31 shows induction of cell proliferation in a time course of each human peripheral blood T cells by stimulating with various antibodies.

Figure 32A:
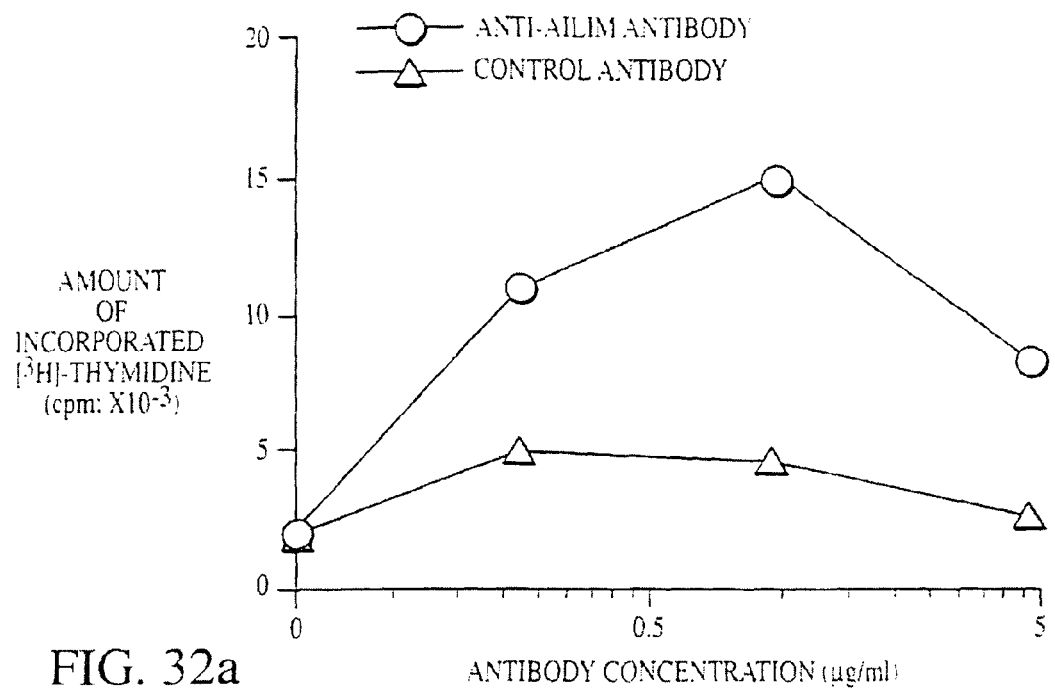
Figure 32B:
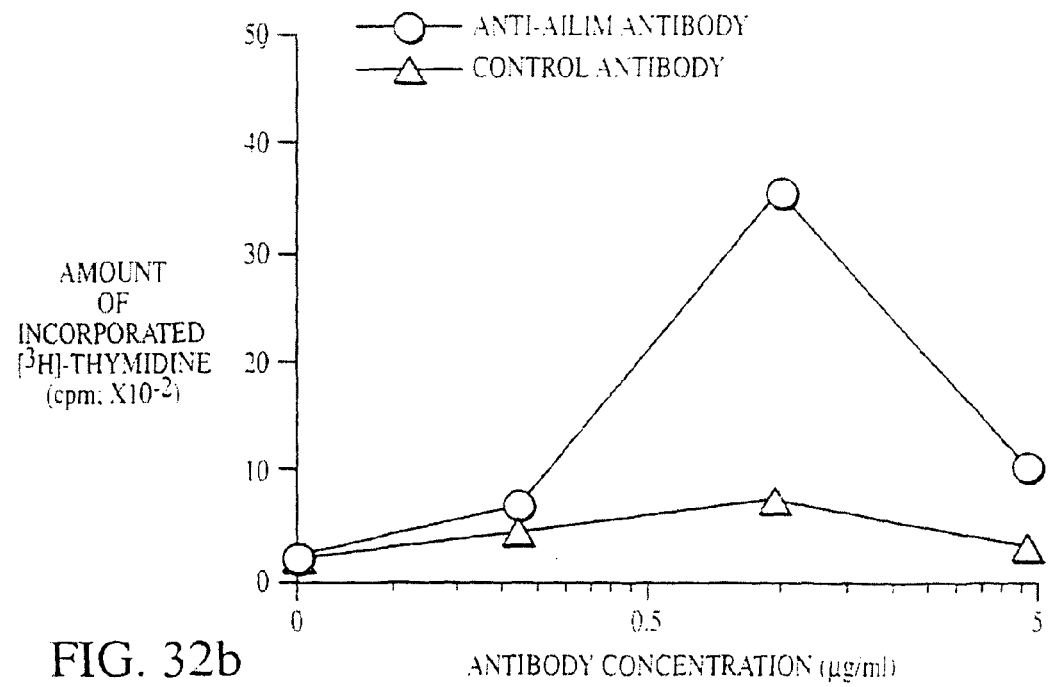

FIG. 32 shows the levels of cell proliferation in each mouse spleen cells and mouse spleen-derived T cells cultured on a microplate coated with anti-CD3 antibody and anti-AILIM antibody.

Sub figure (a) shows the levels of proliferation of mouse spleen cells.

Sub figure (b) shows levels of proliferation of mouse spleen-derived T cells.

Figure 33:
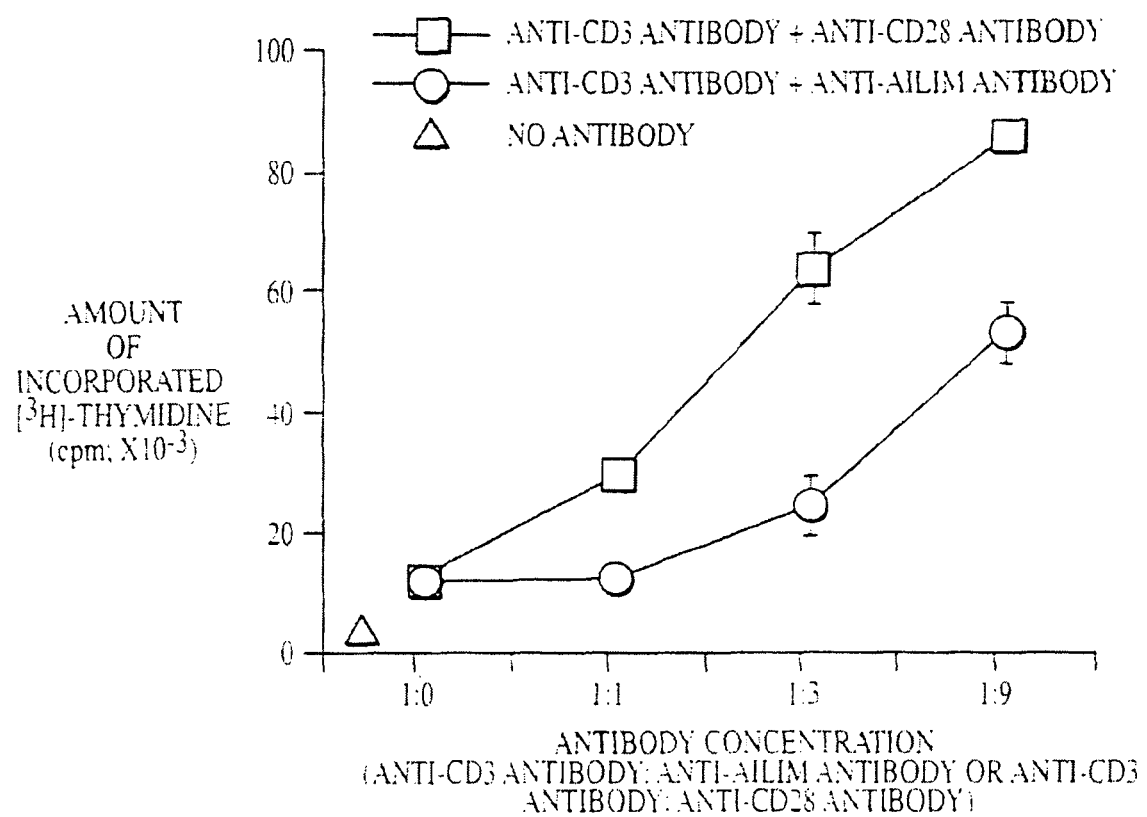

FIG. 33 shows levels of proliferation of each mouse spleen cell cultured using microbeads (constant concentration), coated with anti-CD3 antibody (constant concentration), and anti-AILIM antibody (various concentration).

Figure 34:
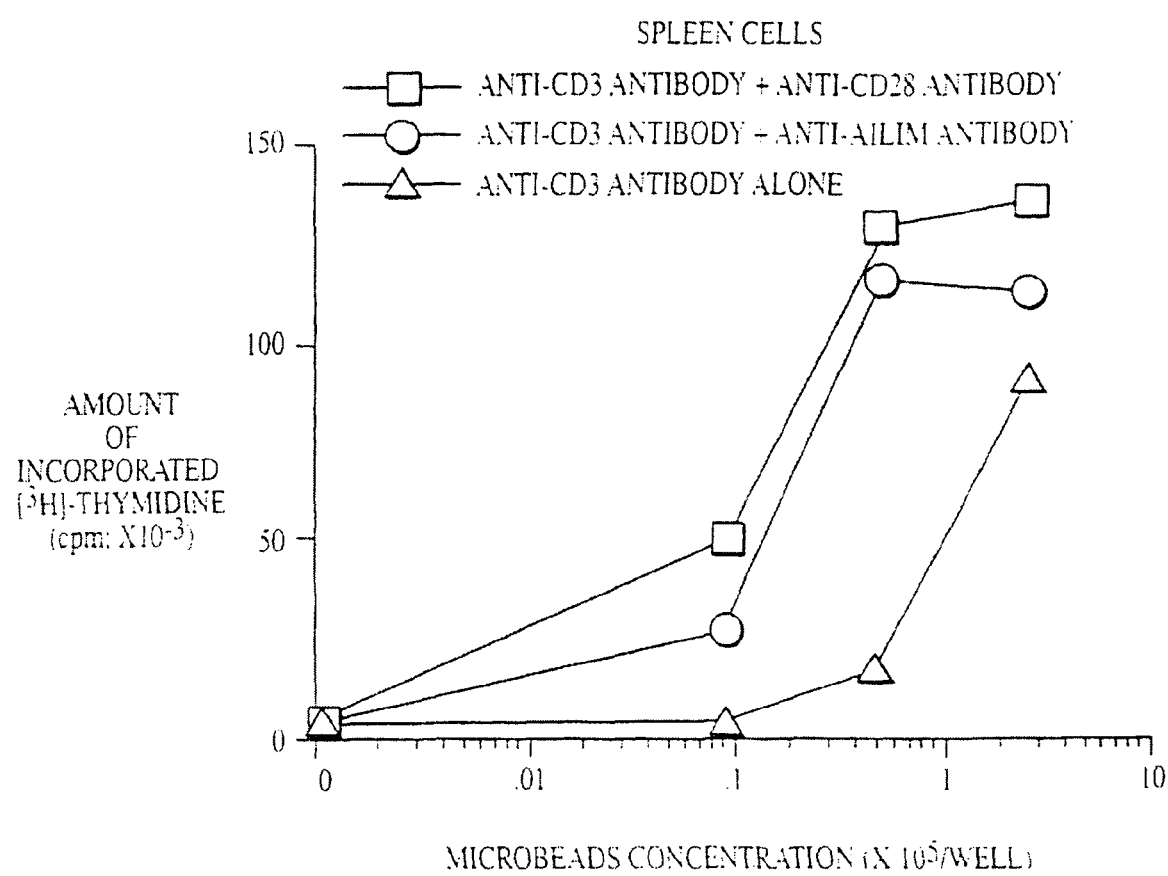

FIG. 34 shows levels of proliferation of each mouse spleen cell cultured using microbeads (various concentrations), coated with anti-CD3 antibody (constant concentration), and anti-AILIM antibody (constant concentration).

Figure 35:
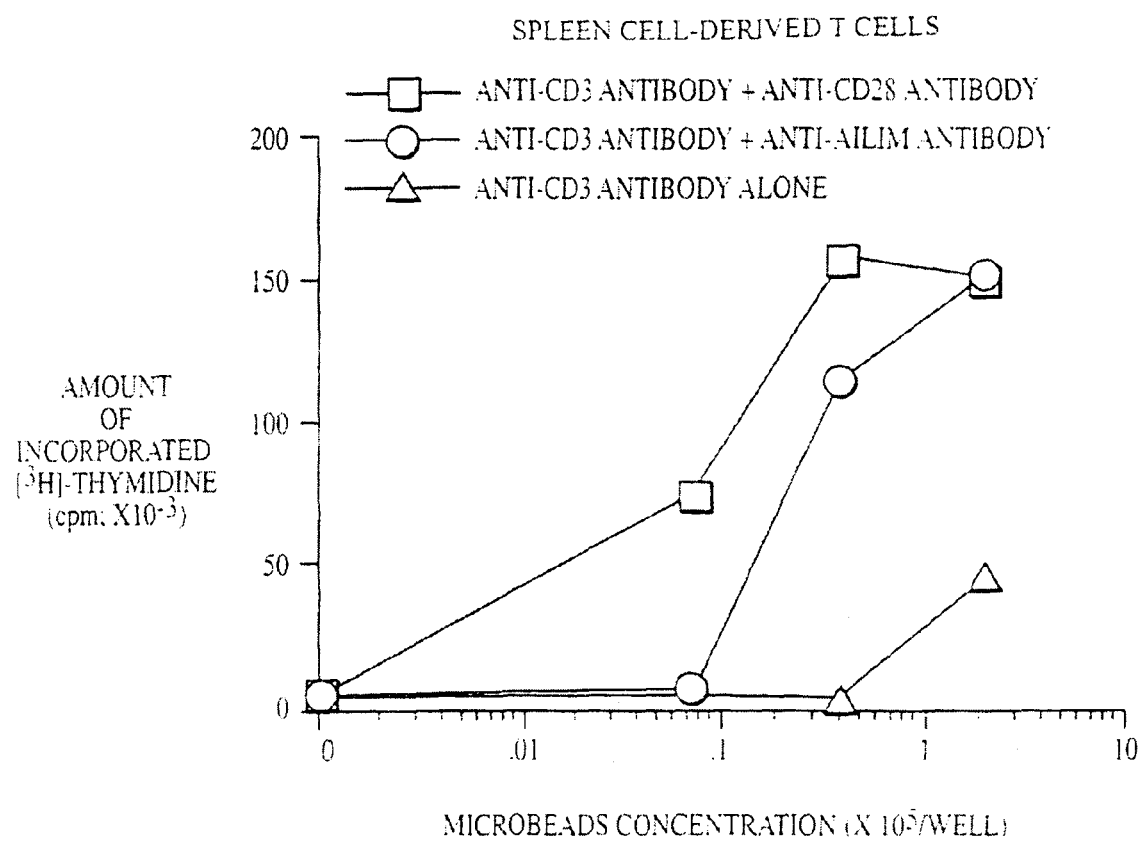

FIG. 35 shows levels of proliferation of each mouse spleen-derived T cell cultured using microbeads (various concentrations), coated with anti-CD3 antibody (constant concentration), and anti-AILIM antibody (constant concentration).

Figure 36:
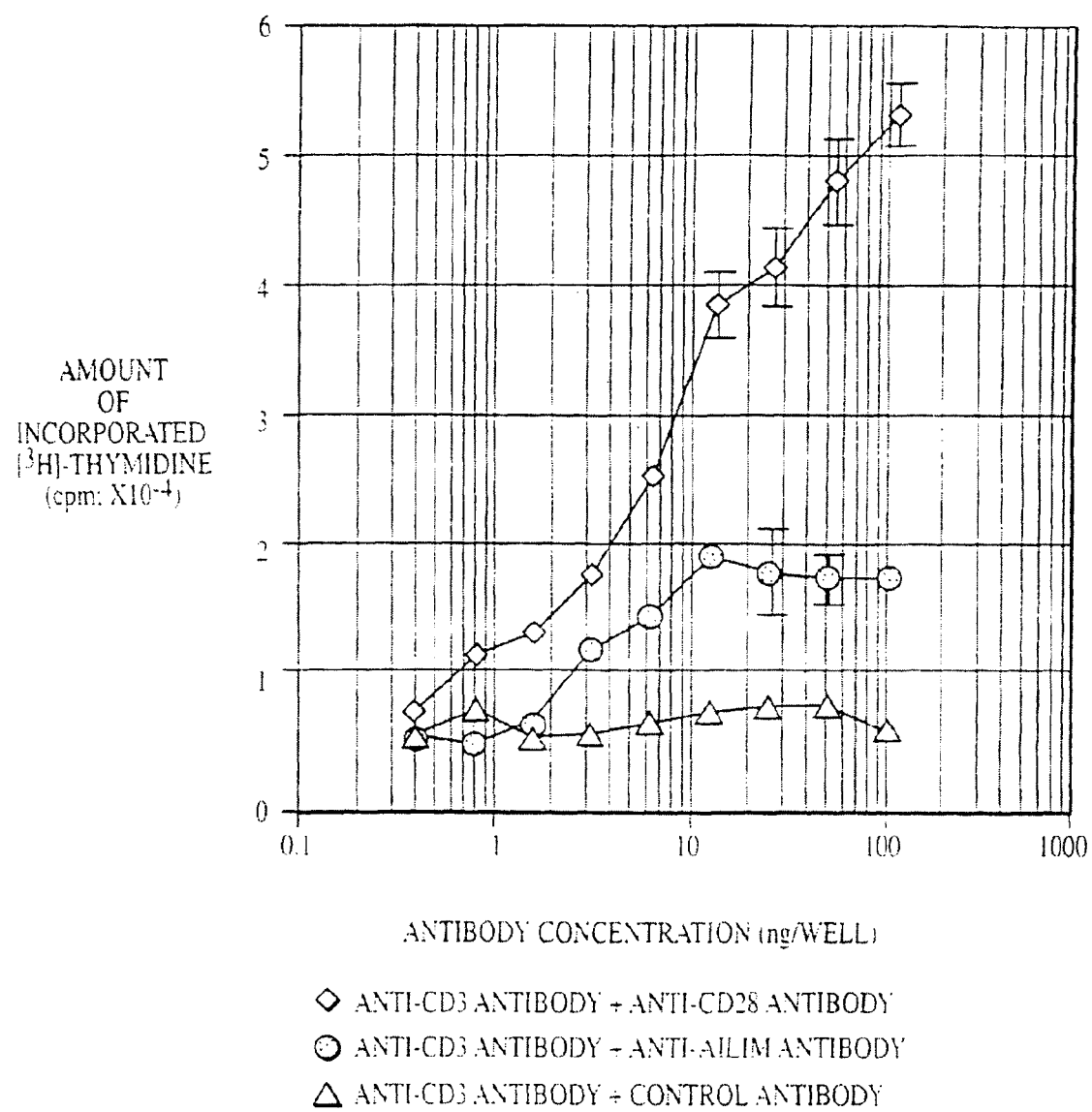

FIG. 36 shows the induction of cell proliferation of each rat lymph node-derived T cell by the stimulating with various antibodies at the various concentrations.

Figure 37:
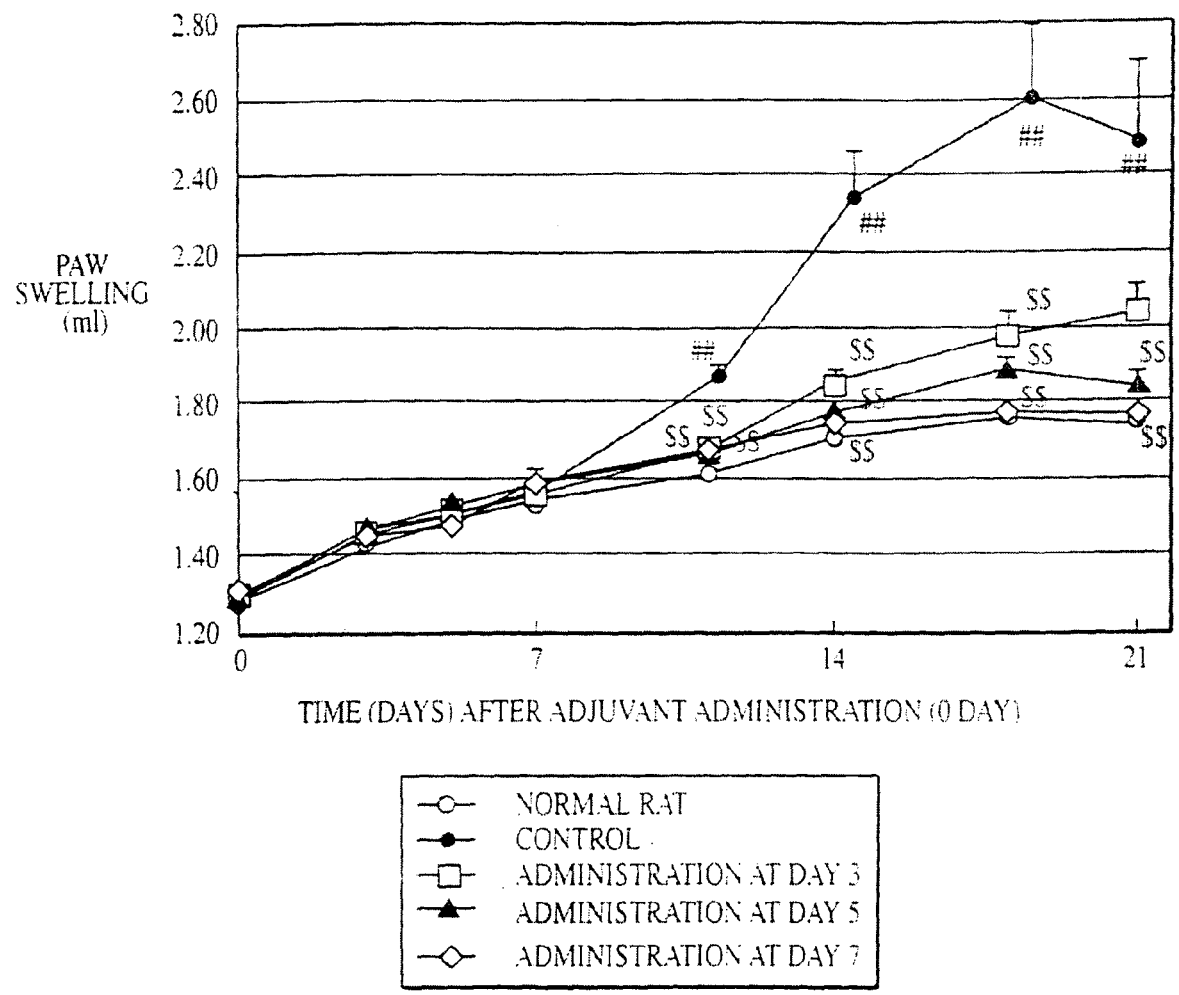

FIG. 37 shows the therapeutic effect of the single administration (constant concentration) of anti-AILIM antibody on paw swelling which is a parameter for arthrosis in a host suffering from arthrosis.

Figure 38:
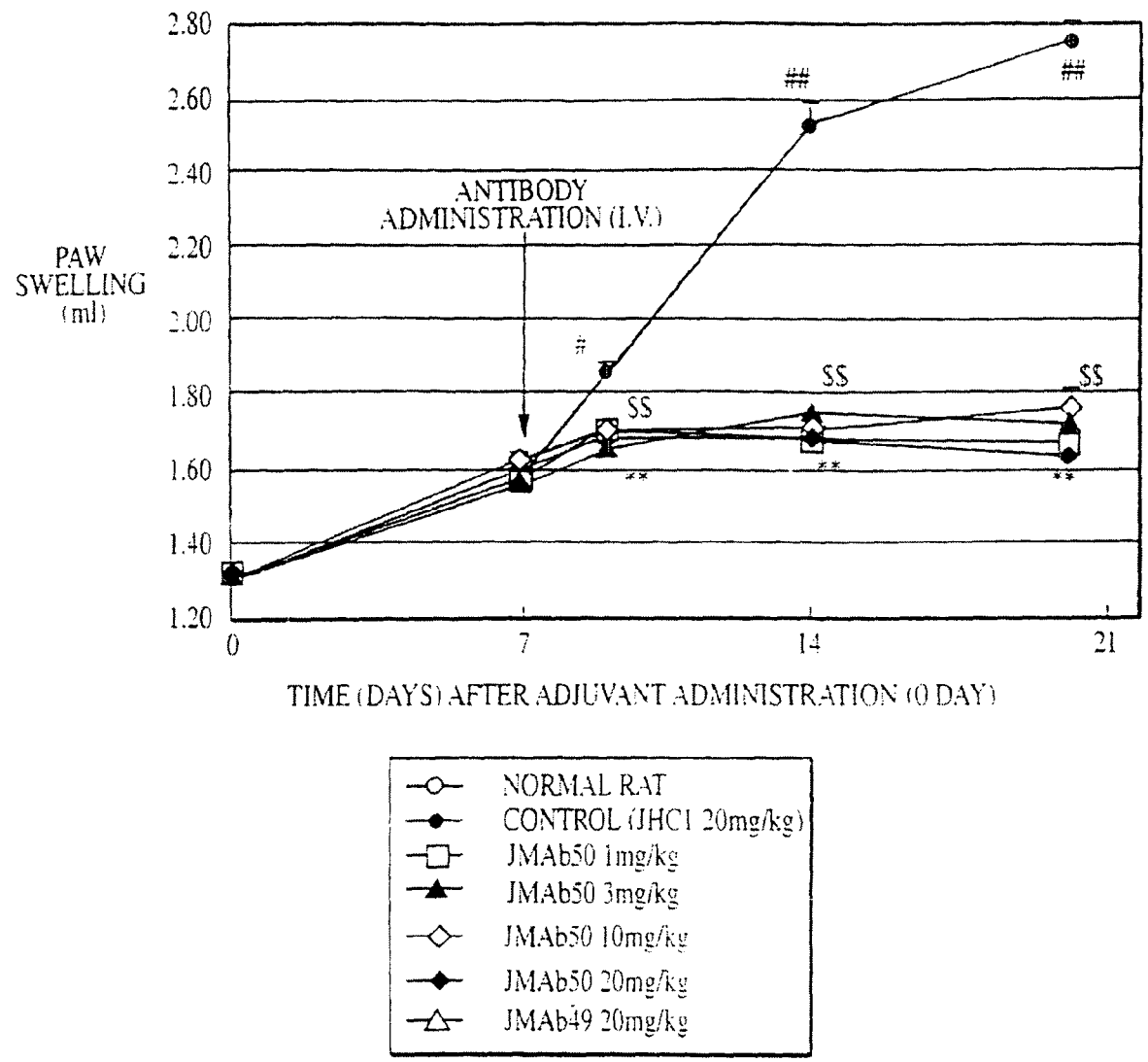

FIG. 38 shows the therapeutic effect of the single administration (various concentration) of anti-AILIM antibody on paw swelling which is a parameter for arthrosis in a host suffering from arthrosis.

Figure 39:
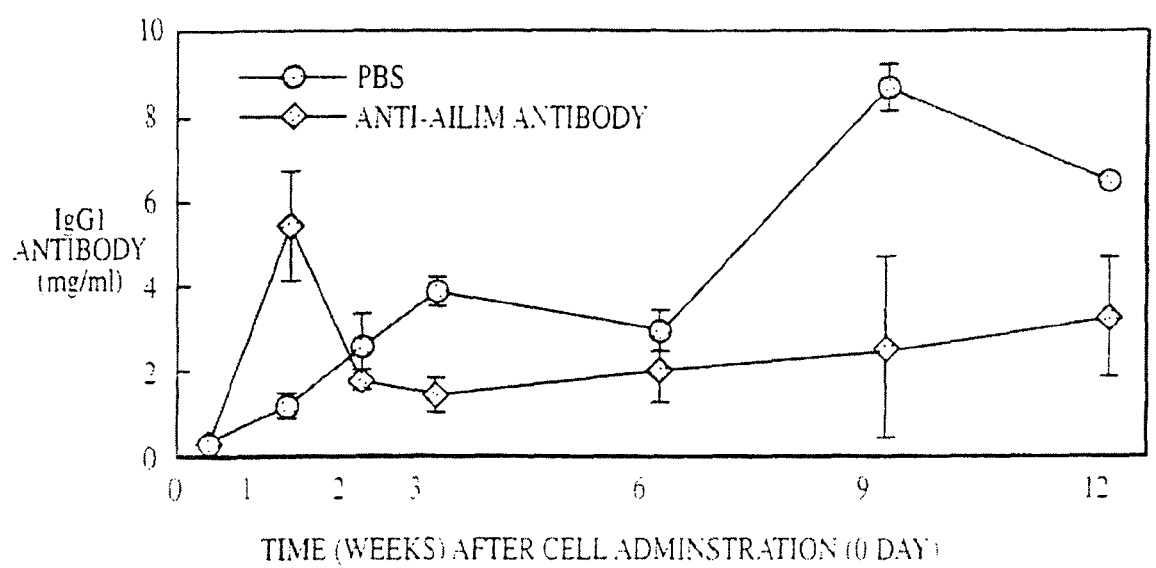

FIG. 39 shows the inhibitory effect of anti-AILIM antibody on the increased production of IgG which is one of the graft versus host reactions (GVH reactions) in graft versus host disease (GVHD).

Figure 40:
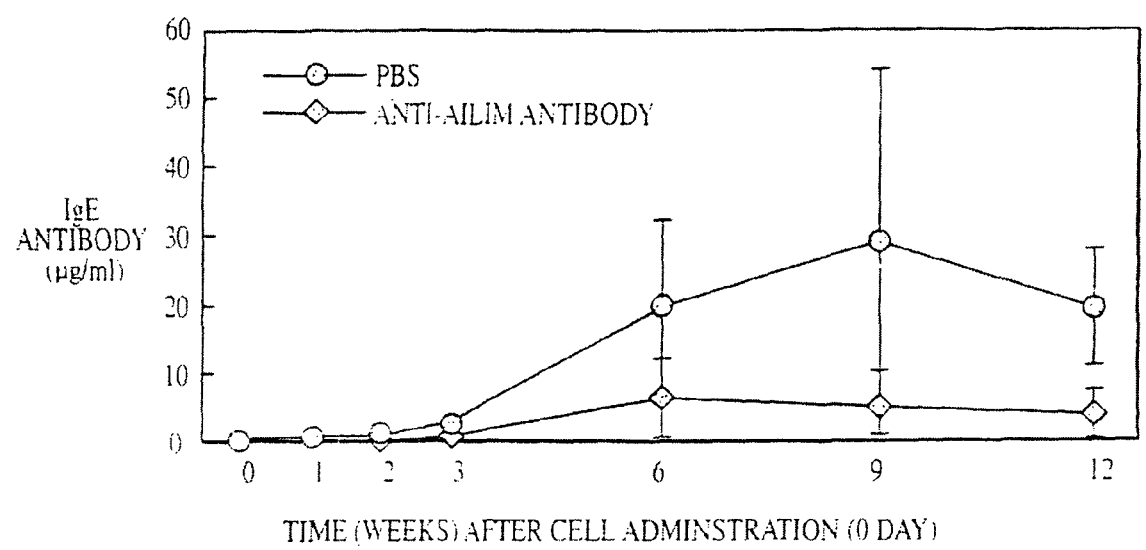

FIG. 40 shows the inhibitory effect of anti-AILIM antibody on the increased production of IgE which is one of the graft versus host reactions (GVH reactions) in graft versus host disease (GVHD).

Figure 41:
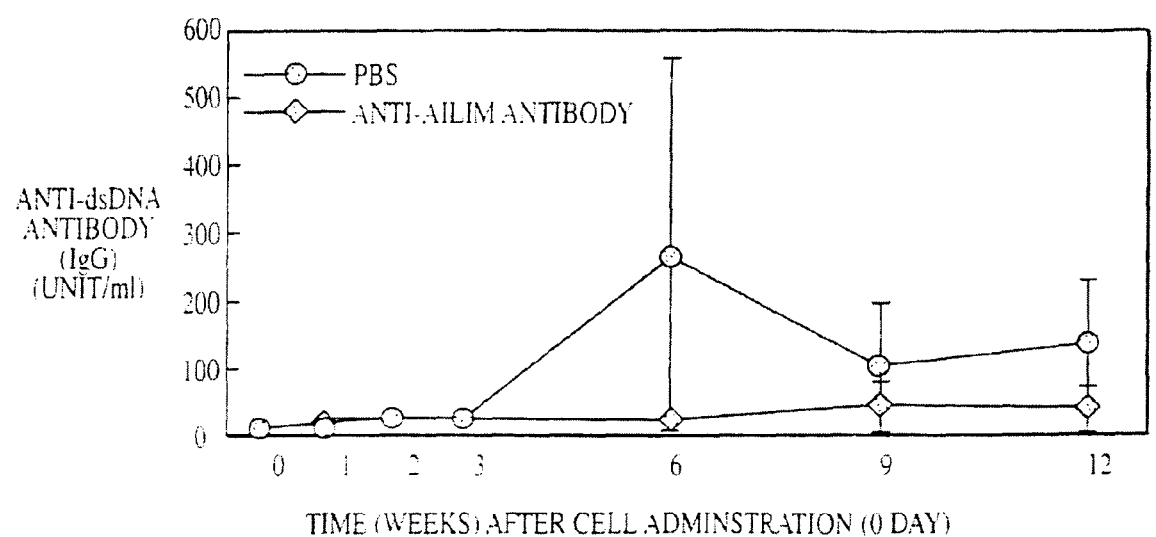

FIG. 41 shows the inhibitory effect of anti-AILIM antibody on the increased anti-dsDNA antibody titer which is one of the graft versus host reactions (GVH reactions) in graft versus host disease (GVHD).

Figure 42:
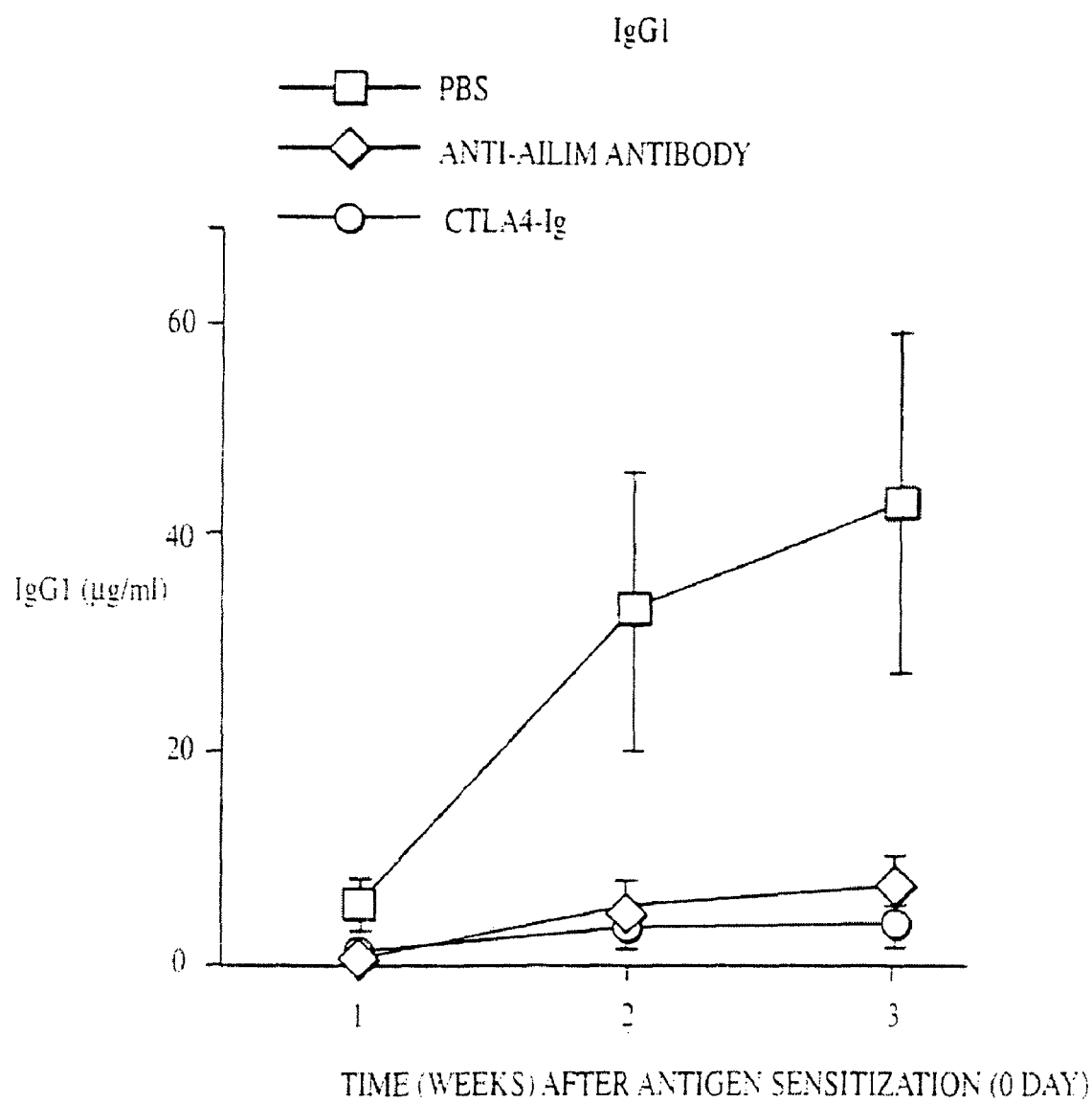

FIG. 42 shows the inhibitory effect of anti-AILIM antibody in a host in vivo sensitized with NP-KLH which is a foreign antigen on the production of IgG1 antibody against the foreign antigen.

Figure 43:
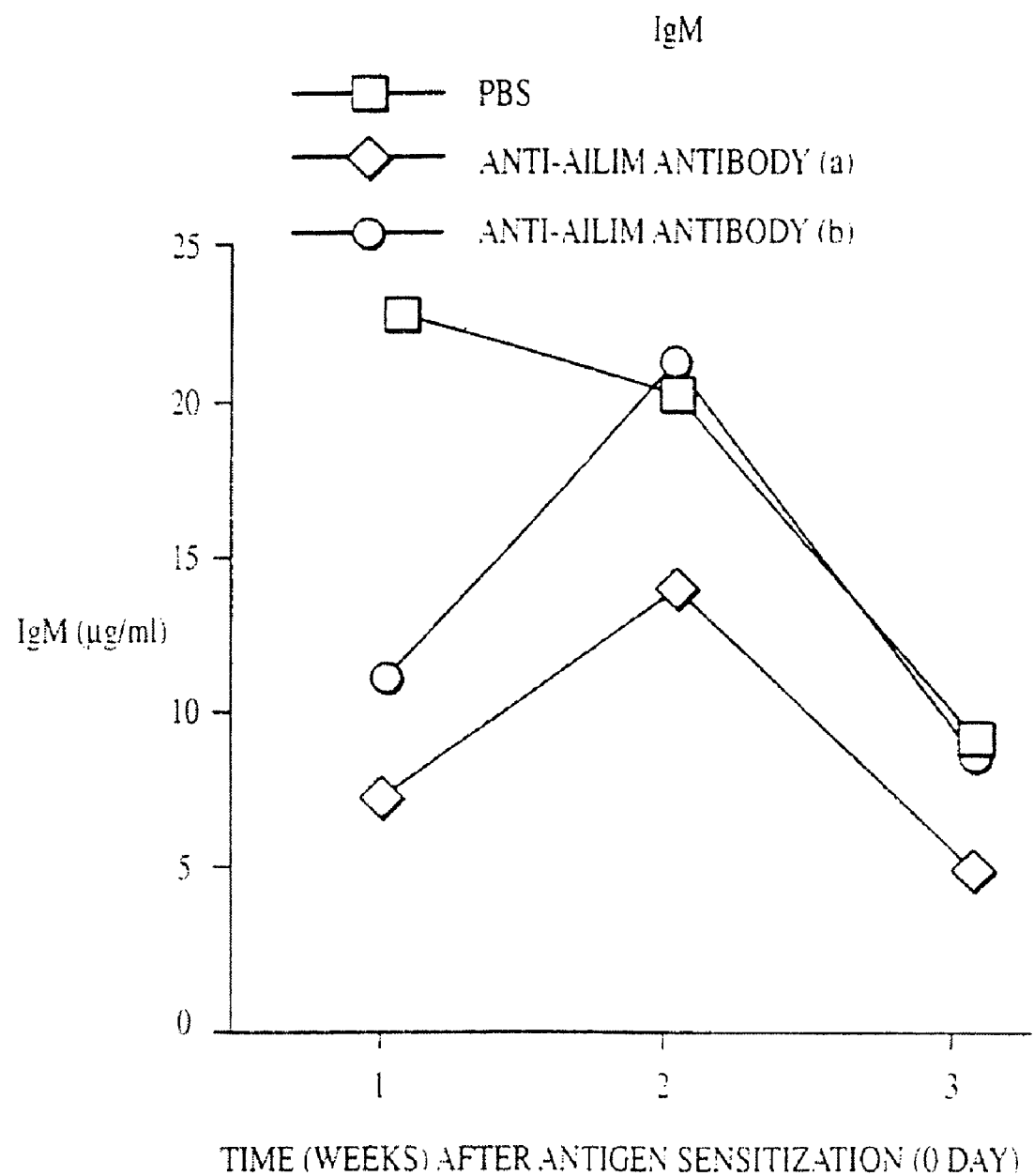

FIG. 43 shows the inhibitory effect of anti-AILIM antibody in a host in vivo sensitized with NP-KLH which is the foreign antigen on the production of IgM antibody against the foreign antigen.

Figure 44:
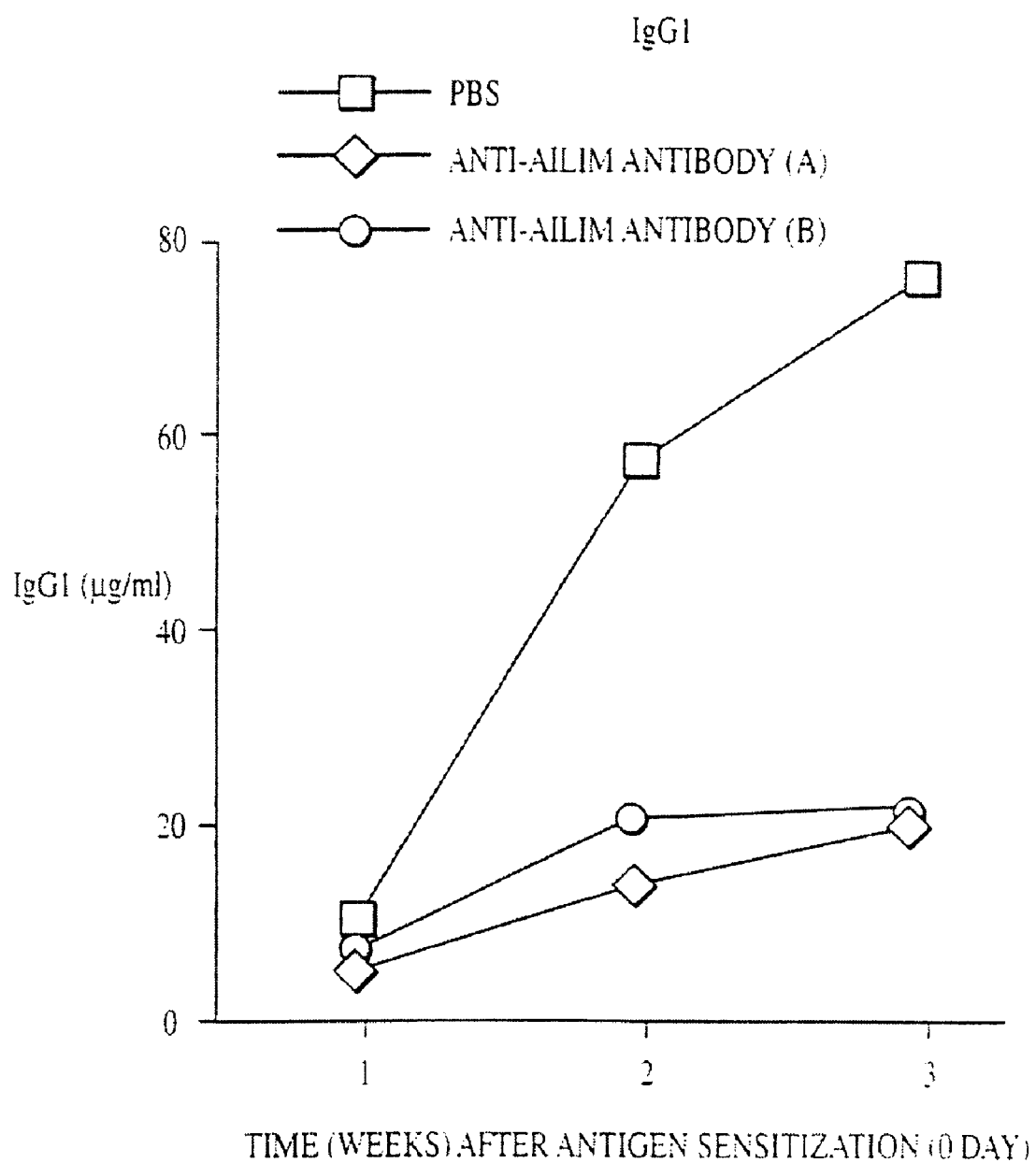

FIG. 44 shows the inhibitory effect of anti-AILIM antibody in a host in vivo sensitized with NP-KLH which is the foreign antigen on the production of IgG1 antibody against the foreign antigen.

Figure 45:
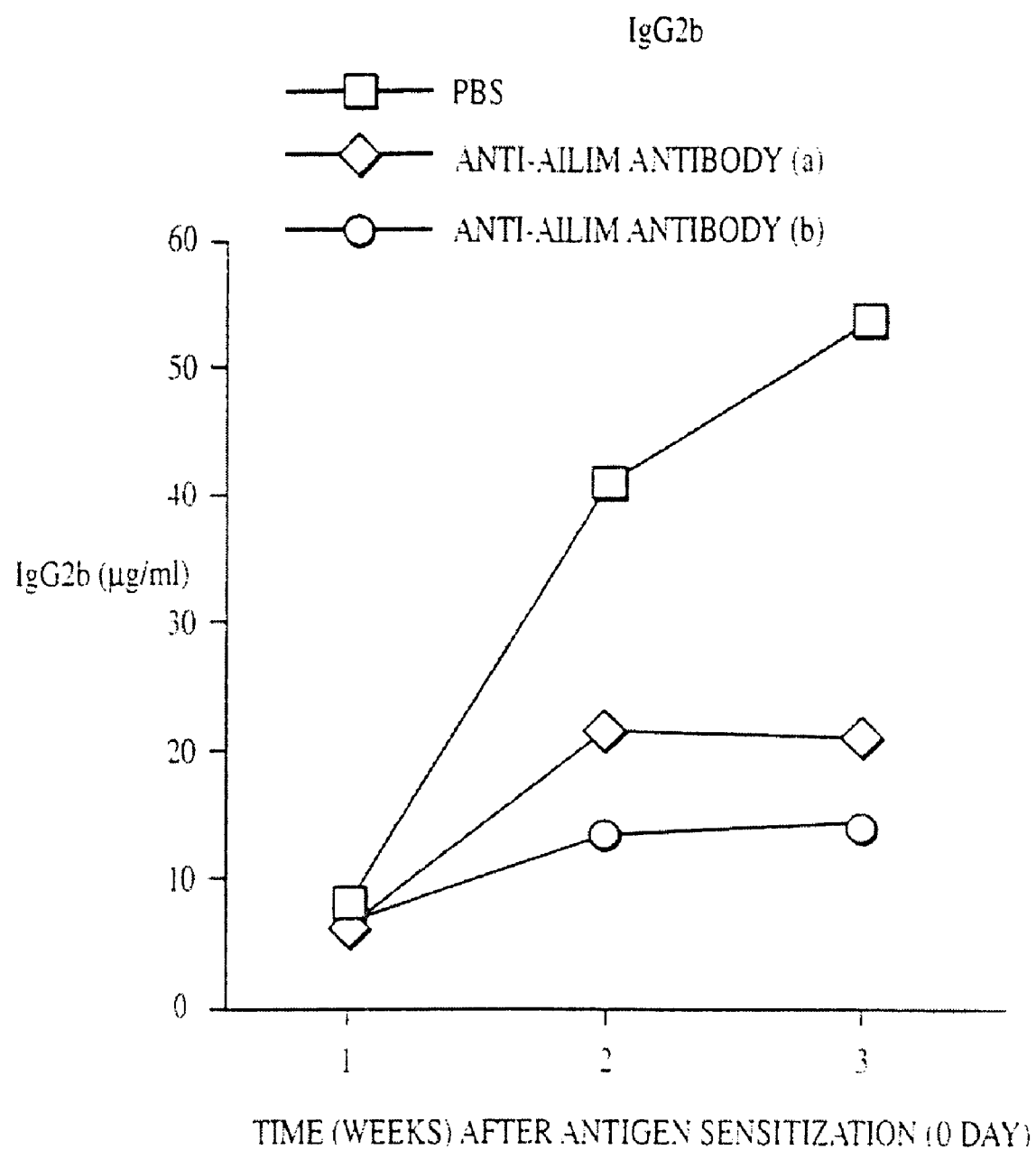

FIG. 45 shows the inhibitory effect of anti-AILIM antibody in a host in vivo sensitized with NP-KLH which is the foreign antigen on the production of IgG2b antibody against the foreign antigen.

Figure 46:
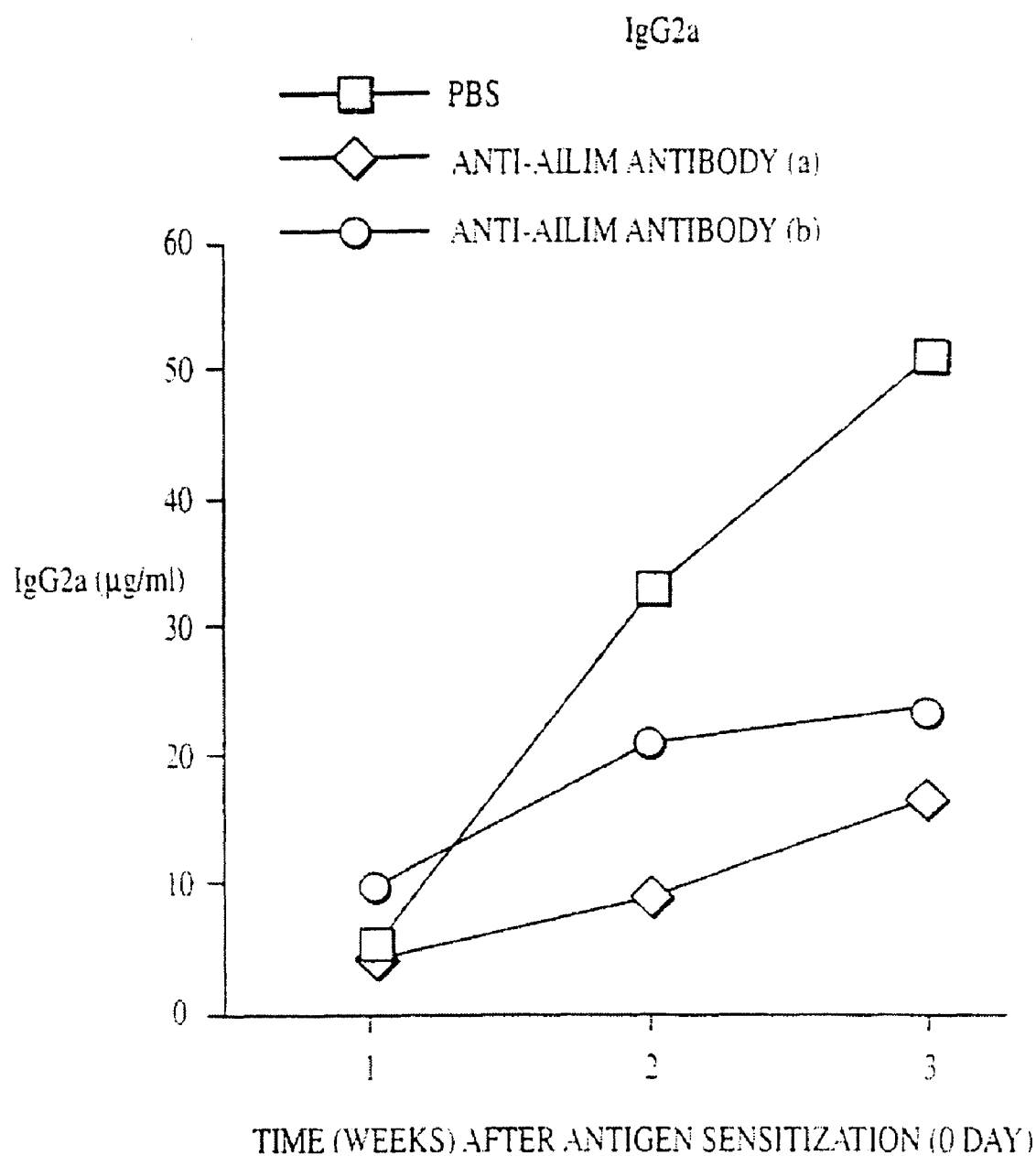

FIG. 46 shows the inhibitory effect of anti-AILIM antibody in a host in vivo sensitized with NP-KLH which is the foreign antigen on the production of IgG2a antibody against the foreign antigen.

Figure 47:
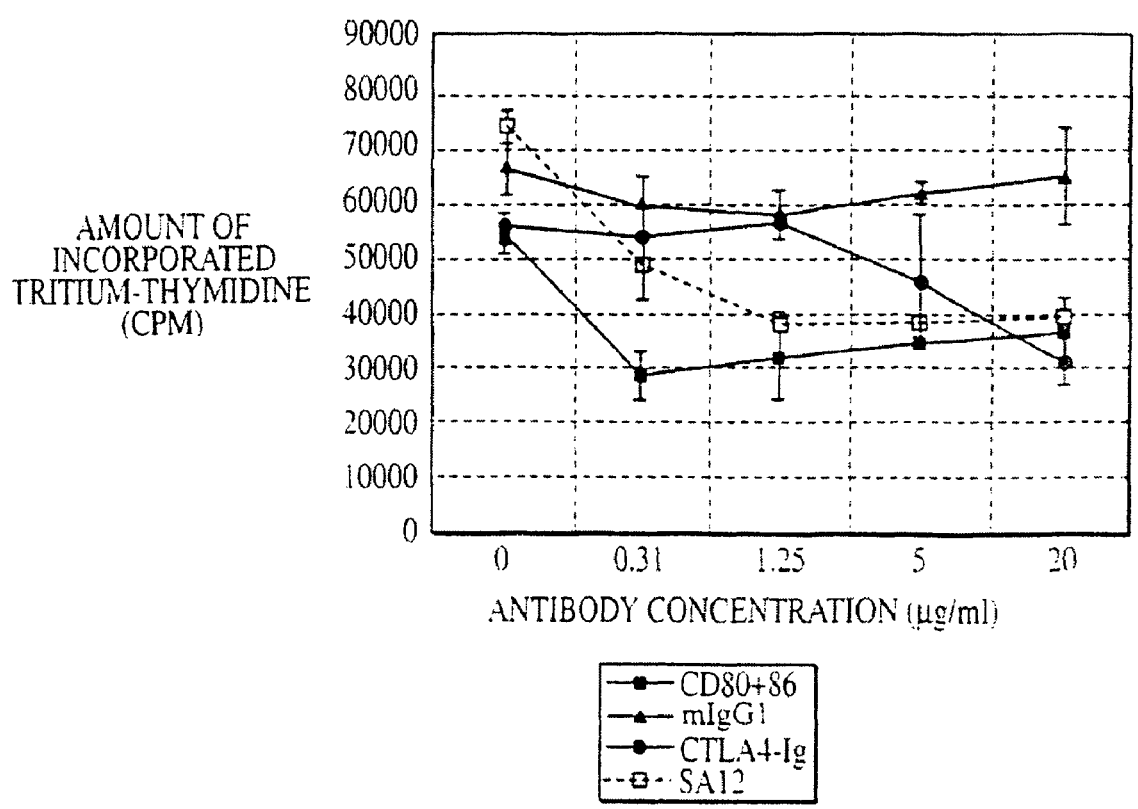

FIG. 47 shows the inhibitory effect on T cell proliferation in the case of culturing T cells from a normal healthy person "donor A", with PBMC of a normal healthy person "donor D" by various test samples in the proliferation test of the T cells through the mixed lymphocyte reactions (MLR).

The vertical axis indicates the amount of incorporation of [$^3$H] thymidine as an index showing a level of cell proliferation, and the horizontal axis shows the concentration of the test samples.

Each description in the figures shows the following.

"CD80+86": The mixture of anti-CD80 antibody and anti-CD86 antibody

"mIgG1": Anti-human CD34/IgG1 mouse monoclonal antibody

"CTLA4-Ig": Human CTLA4-IgFc chimeric molecule

"SA12": Anti-human AILIM mouse monoclonal antibody

Figure 48:
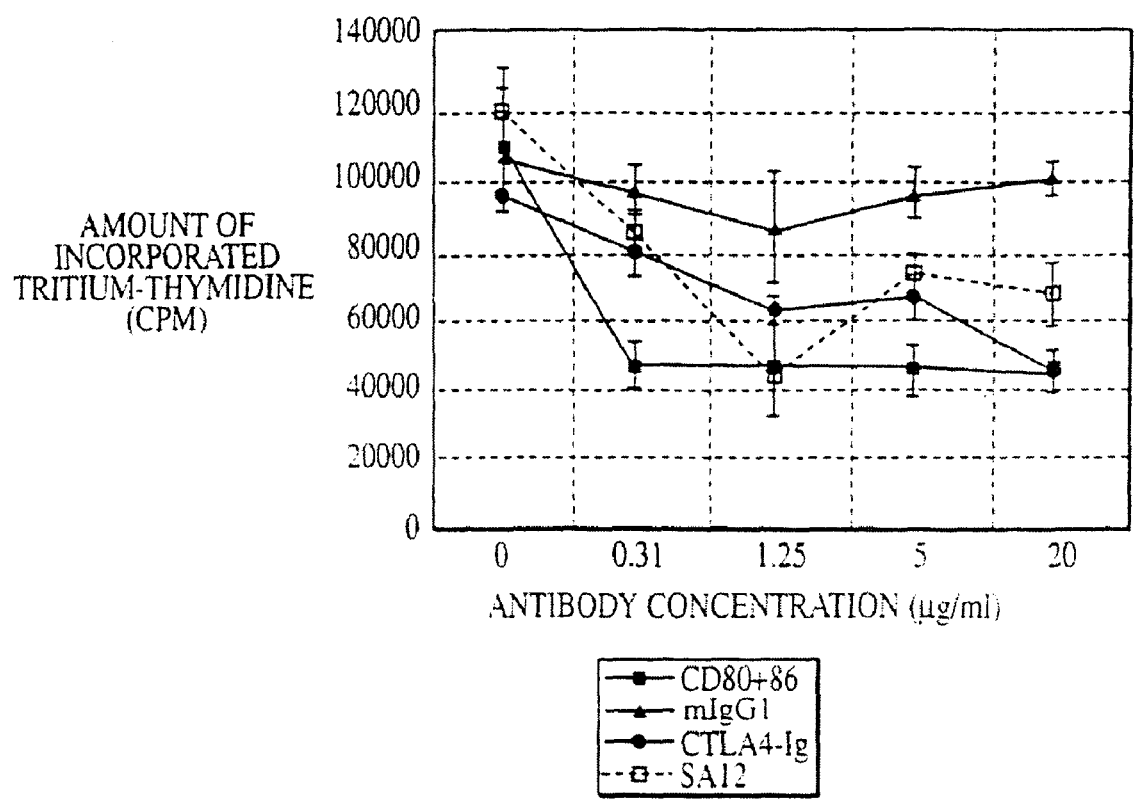

FIG. 48 shows the inhibitory effect on T cell proliferation in the case of culturing T cells from a normal healthy person "donor D", with PBMC of a normal healthy person "donor B" by various test samples in the proliferation test of the T cells through the mixed lymphocyte reaction (MLR).

The vertical axis indicates the amount of incorporation of [$^3$H] thymidine as an index showing a level of cell proliferation, and the horizontal axis shows the concentration of the test samples.

Each description in the figures shows the following.

"CD80+86": The mixture of anti-CD80 antibody and anti-CD86 antibody

"mIgG1": Anti-human CD34/IgG1 mouse monoclonal antibody

"CTLA4-Ig": Human CTLA4-IgFc chimeric molecule

"SA12": Anti-human AILIM mouse monoclonal antibody

Figure 49:
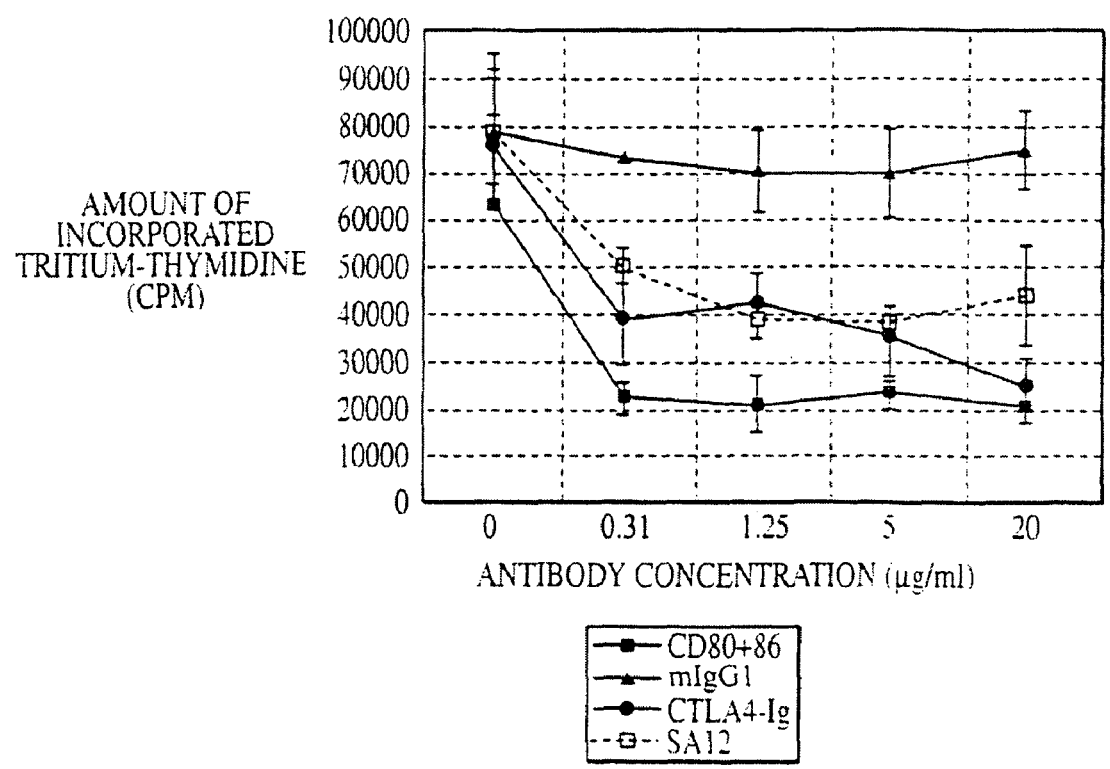

FIG. 49 shows the inhibitory effect on T cell proliferation in the case of culturing T cells from a normal healthy person "donor C", with PBMC of a normal healthy person "donor A" by various test samples in the proliferation test of the T cells through the mixed lymphocyte reaction (MLR).

The vertical axis indicates the amount of incorporation of [$^3$H] thymidine as an index showing a level of cell proliferation, and the horizontal axis shows the concentration of the test samples.

Figure 50:
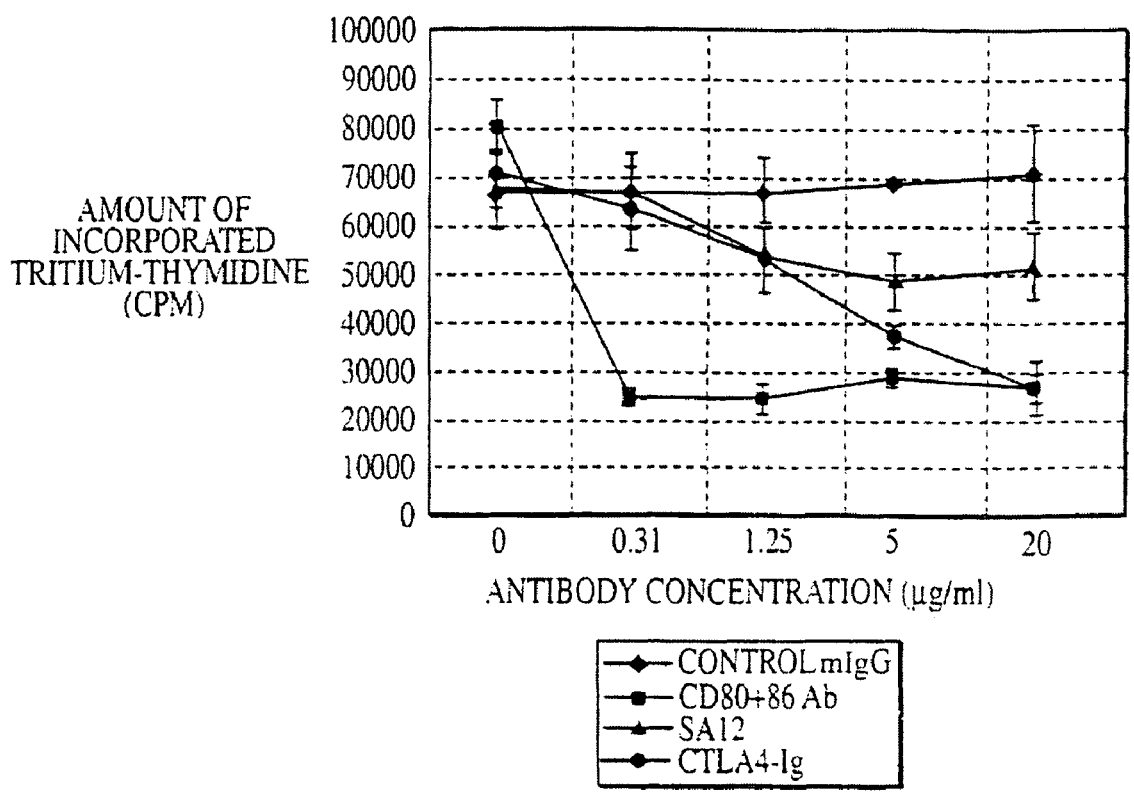

Each description in the figures shows the following.
"CD80+86": The mixture of anti-CD80 antibody and anti-CD86 antibody
"mIgG1": Anti-human CD34/IgG1 mouse monoclonal antibody
"CTLA4-Ig": Human CTLA4-IgFc chimeric molecule
"SA12": Anti-human AILIM mouse monoclonal antibody FIG. 50 shows the inhibitory effect on T cell proliferation in the case of culturing T cells from a normal healthy person "donor E", with PBMC of a normal healthy person "donor G" by various test samples in the proliferation test of the T cells through the mixed lymphocyte reaction (MLR).

The vertical axis indicates the amount of incorporation of [$^3$H] thymidine as an index showing a level of cell proliferation, and the horizontal axis shows the concentration of the test samples.

Figure 51:
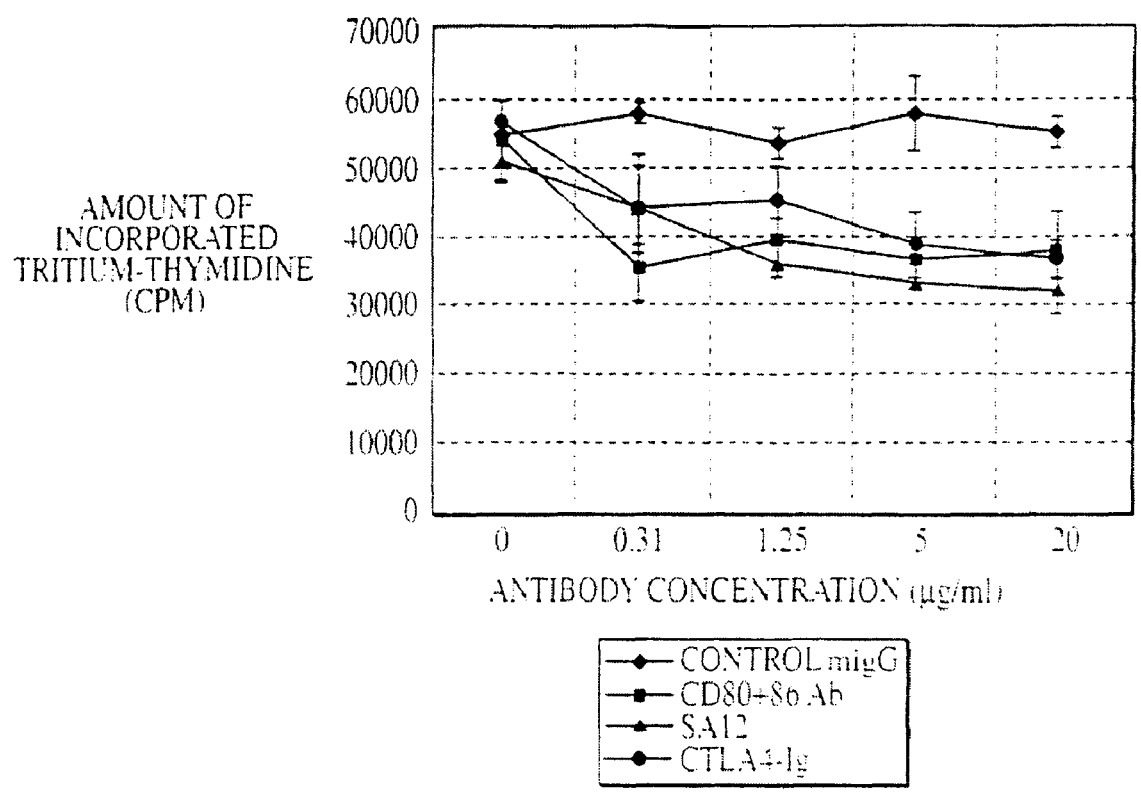

Each description in the figures shows the following.
"control mIgG": Anti-human CD34/IgG1 mouse monoclonal antibody
"CD80+86Ab": The mixture of anti-CD80 antibody and anti-CD86 antibody
"SA12": Anti-human AILIM mouse monoclonal antibody
"CTLA4-Ig": Human CTLA4-IgFc chimeric molecule FIG. 51 shows the inhibitory effect on T cell proliferation in the case of culturing T cells from a normal healthy person "donor F", with PBMC of a normal healthy person "donor E" by various test samples in the proliferation test of the T cells through the mixed lymphocyte reaction (MLR).

The vertical axis indicates the amount of incorporation of [$^3$H] thymidine as an index showing a level of cell proliferation, and the horizontal axis shows the concentration of the test samples.

Figure 52:
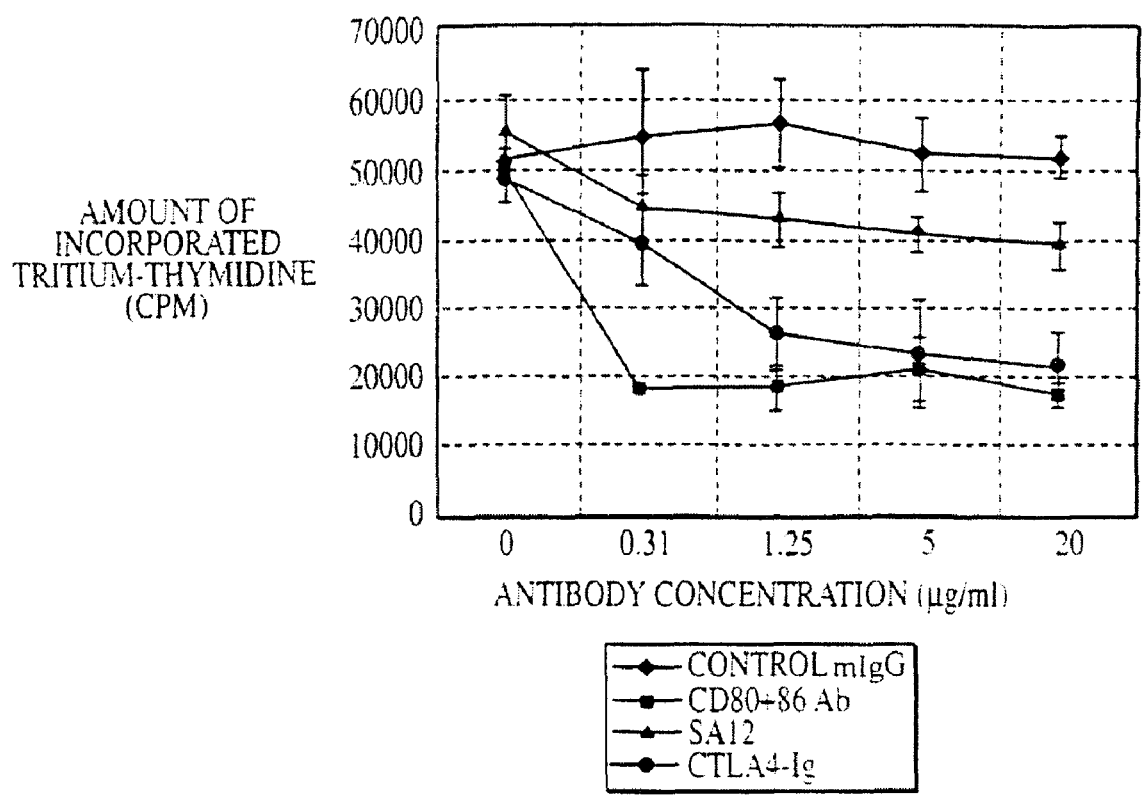

Each description in the figures shows the following.
"control mIgG": Anti-human CD34/IgG1 mouse monoclonal antibody
"CD80+86Ab": The mixture of anti-CD80 antibody and anti-CD86 antibody
"SA12": Anti-human AILIM mouse monoclonal antibody
"CTLA4-Ig": Human CTLA4-IgFc chimeric molecule FIG. 52 shows the inhibitory effect on T cell proliferation in the case of culturing T cells from a normal healthy person "donor G", with PBMC of a normal healthy person "donor F" by various test samples in the proliferation test of the T cells through the mixed lymphocyte reaction (MLR).

The vertical axis indicates the amount of incorporation of [$^3$H] thymidine as an index showing a level of cell proliferation, and the horizontal axis shows the concentration of the test samples.

Each description in the figures shows the following.
"control mIgG": Anti-human CD34/IgG1 mouse monoclonal antibody
"CD80+86Ab": The mixture of anti-CD80 antibody and anti-CD86 antibody
"SA12": Anti-human AILIM mouse monoclonal antibody
"CTLA4-Ig": Human CTLA4-IgFc chimeric molecule

BEST MODE FOR CARRYING OUT THE INVENTION

The present invention is illustrated in more detail below with reference to Examples, but is not to be construed as being limited thereto.

EXAMPLE 1

Preparation of Experimental Materials

Unless otherwise stated, the experimental materials (animals, antibodies, cells) used in the tests described below were prepared as follows.

<1-1> Animals

C57BL/6 mice (male, 5- to 8-week-old) and BALB/c mice (male, 5- to 8-week-old) were purchased from JAPAN SLC. Wistar rats (male, 5- to 6-week-old) were purchased from Charles River Japan Inc.

<1-2> Preparation of Anti-Rat AILIM Monoclonal Antibodies

Hybridomas designated as "JTT-1" and "JTT-2" capable of producing mouse anti-rat AILIM monoclonal antibody (mouse anti-rat JTT-1 antigen monoclonal antibody), which were created and reported previously by the present inventors, have been deposited internationally (as of Oct. 11, 1996, both hybridomas have been deposited internationally in The National Institute of Bioscience and Human-Technology, The Agency of Industrial Science and Technology, The Ministry of International Trade and Industry (1-1-3 Higashi, Tsukuba, Ibaraki, Japan (Zip Code: 305-8566)), which is an international depositary authority under the Budapest Treaty). Monoclonal antibodies purified from culture supernatants of "JTT-1" (international accession number FERM BP-5707) and "JTT-2" (international accession number FERM BP-5708) in vitro or in vivo, or ascites, were used in the tests described below (JP-A 11-29599 (Examples 1 and 2), and WO98/38216 (Examples 1 and 2)).

Hereafter, these mouse anti-rat AILIM monoclonal antibodies are referred to as "JTT-1 antibody" and "JTT-2 antibody" (IgG1), respectively. In some cases, "JTT-1 antibody" and "JTT-2 antibody" are also referred to as "JMab49" and "JMab50," respectively.

Unless otherwise stated, the anti-rat AILIM antibody used in the following tests is "JTT-2 antibody" (also referred to as JMab50; IgG1).

<1-3> Preparation of Anti-Human AILIM Monoclonal Antibodies

Each of hybridomas named "SA12" and "SG430" producing mouse anti-human AILIM monoclonal antibody (mouse anti-human JTT-1 antigen monoclonal antibody), which were created and reported previously by the present inventors, was given to ICR nu/nu mice (female, 7- to 8-week-old) by intraperitoneal injection ($10^6$ to $10^7$ cells/0.5 ml/mouse for each hybridoma). 10 to 20 days after the injection, the ascites was collected from each mouse by laparotomy under anesthesia according to a commonly used method. The respective mouse anti-human AILIM monoclonal antibodies were thus prepared on a large scale (JP-A 11-29599 (Example 12), and WO98/38216 (Example 12)).

Hereafter, these two types of mouse anti-human AILIM monoclonal antibodies are referred to as "SA12 antibody" (IgG1) and "SG430 antibody" (IgG1). The two were used in the tests described below.

<1-4> Preparation of Anti-Mouse AILIM Monoclonal Antibodies

The antibodies were prepared as follows:

According to a commonly used method using genetic recombination techniques, a transformed cell capable of expressing mouse AILIM was prepared using the cDNA encoding the full-length amino acid sequence of mouse AILIM (mouse JTT-1 antigen) (JP-A 11-29599 (SEQ ID NO: 5), and WO98/38216 (SEQ ID NO: 5)), which had previously been cloned by the present inventors.

The transformed cells were homogenized and then subjected to ultracentrifugation (100,000×g). The resulting precipitate containing cell membrane fraction was recovered and then suspended in PBS. Together with Freund's complete adjuvant, the obtained cell membrane fraction was given to Wistar rats by footpad injection for primary immunization (0 day). The cell membrane fraction antigen was repeatedly given to the rats by footpad injection, on seventh day, fourteenth day and twenty-eighth day after the primary administration. Two days after the final immunization, the lymph node cells were collected from the rats.

The lymph node cells were mixed with mouse myeloma PAI cells (JCR No. B0113; Res. Disclosure, Vol. 217, pp. 155, 1982) at a ratio of 5:1. The cells were fused to each other by using polyethylene glycol 4000 (Boehringer Mannheim) as a fusing agent to create hybridomas capable of producing monoclonal antibodies. Selection of hybridoma was performed by culturing the fused cells in an ASF104 medium (Ajinomoto) containing in HAT, 10% fetal calf serum and aminopterin.

The reactivity against mouse AILIM (mouse JTT-1 antigen) of each monoclonal antibody in culture supernatant of hybridoma was tested as follows: each culture supernatant was allowed to react to the transformed cells expressing the above-mentioned recombinant mouse AILIM; and then the cells were further allowed to react to FITC-labeled anti-rat IgG (Cappel); fluorescence intensities of the stained cells were measured in an EPICS-ELITE flow cytometer. The screening yielded multiple hybridomas capable of producing monoclonal antibodies reactive to mouse AILIM (mouse JTT-1 antigen).

Two distinct hybridomas selected from them were named "B10.5" and "B9B6." Each of the hybridomas ($10^6$ to $10^7$ cells/0.5 ml/mouse for each) was given to ICR nu/nu mice (female, 7- to 8-week old) by intraperitoneal injection. 10 to 20 days after the injection, the ascites was collected from each mouse by laparotomy under anesthesia according to a commonly used method. The rat anti-mouse AILIM monoclonal antibodies were thus prepared on a large scale. Hereafter, these two types of rat anti-mouse AILIM monoclonal antibodies produced by the "B10.5" and "B9B6" hybridomas will be designated as "B10.5 antibody" (IgG2a) and "B9B6 antibody" (IgG2a). The two antibodies were used in the tests described below.

<1-5> Preparation of Lymphocytes

Mice were sacrificed by decapitation. Then thymus and peripheral lymphoid tissues (spleen and lymph node) were taken out according to a commonly used method. The tissues were cut into small blocks on a stainless mesh. Cell suspensions were prepared by suspending the tissue blocks in RPMI1640 medium containing 10% fetal calf serum (FCS). The suspensions of cell ($1 \times 10^7$ to $3 \times 10^7$ cells/ml for each) were plated in a dish and then cultured for 2 hours in a $CO_2$ incubator. After the culture was completed, non-adhesive cells were carefully recovered from the dish and then washed with RPMI1640 medium. Mouse cells were thus obtained from various tissues.

Rat cells from various tissues were also prepared from thymus and peripheral lymphoid tissues (spleen and lymph node) by the same method as described above.

Human peripheral blood T cells (from healthy normal persons and patients) were prepared according to a commonly used method. Specifically, heparinated blood sample collected from a healthy normal person or patient was subjected to treatment of separation with lymphoprep (Nycomed) to yield peripheral blood mononuclear cells. Subsequently, T cells were recovered by using a Pan T Cell Isolation kit (Miltenyi).

<1-6> Preparation of Established T Cell Lines

The following tests were conducted by using various lines of mouse T cell (D10, MS202, CD28KO, EL-4, 2L2, and BC3C13) as well as various mouse T cell-derived hybridomas (KV24, D0.11.10, 8-4-31, 3H10-11, 61-21-25, 1-2-66, and 6-13-64) that originate from a mouse T cell-derived hybridoma BW5147, all of which were established by the present inventors.

EXAMPLE 2

Analysis of AILIM Expression in Cells from a Variety of Tissues and Various Cell Lines With a common procedure, experiments of cell staining and flow cytometry were carried out to analyze differences in expression pattern of AILIM in cells from normal and diseased tissues of animals (mouse, rat or human), differences in expression pattern of AILIM between unstimulated T cells and stimulated T cells (activated T cells), as well as those among various T cell lines.

Based on the results obtained in the test described below, the expression pattern of AILIM in tissues and cells were compared with that of CD28. The comparison is schematically shown in FIG. 23. However, it should be noted that the schematic illustration is only an example; as the matter of course, the illustration should not be construed as being used for only a limited explanation to the data obtained in the tests shown below.

<2-1> Cell Staining and Flow Cytometry

Unless otherwise stated, analyses by cell staining and flow cytometer were carried out as follows:

Cells prepared from various tissues by the methods described above as well as T cells or various T cell lines unstimulated or stimulated by each of stimulating substances (anti-CD3 antibody, ConA, or PMA and ionophore, etc.) were re-suspended in phosphate buffer ($Ca^{2+}$, $Mg^{2+}$-free PBS; PBS-) containing 0.5% bovine serum albumin (BSA) and 5 mM EDTA. Subsequently, a primary antibody selected from those indicated in below (A) or (B) was added to the cell suspensions and the mixtures were incubated at 4° C. for 30 minutes:

(A) Labeled antibodies of the above-mentioned various AILIM antibodies (anti-mouse AILIM antibodies, anti-rat AILIM antibodies, anti-human AILIM antibodies), which are labeled with FITC or phycoerythrin (PE);

(B) Unlabeled antibodies of the above-mentioned various AILIM antibodies (anti-mouse AILIM antibodies, anti-rat AILIM antibodies, anti-human AILIM antibodies).

Subsequently, the cells were washed 3 times with the above-mentioned phosphate buffer, and then re-suspended in the same buffer.

When the primary antibody used was an unlabeled anti-AILIM antibody (namely, one of the above-mentioned (B) antibodies), then further FITC-, PE- or biotin-labeled anti-mouse Ig antibody or anti-rat Ig antibody was added as a secondary antibody to the cell suspensions. The suspensions were incubated in the same manner as described above.

When the secondary antibody was a biotin-labeled antibody, then a PE-labeled streptavidin (Pharmingen) was added to the cell suspensions and they were incubated in the same manner as described above. Then the cells were re-suspended in the above-mentioned phosphate buffer.

The sizes of the cells stained by the above-mentioned method and their fluorescence intensities were measured in a FACSort (Becton Dekinson). The distribution of AILIM expression was analyzed by using Lysis II software.

<2-2> Analysis of AILIM Expression in Mouse Thymus-Derived T Cells

The expression of AILIM in T cells isolated from mouse thymus, being a normal lymphoid tissue, was analyzed according to the same method described above in <2-1>. At the same time, similar measurements were carried out to analyze the correlation between the expression pattern of AILIM and the expression of other molecules (CD3 molecule functioning in the primary signaling to T cell, CD28 molecule functioning in the secondary stimulatory signaling, CD4 and CD8 that are T cell surface markers).

Figure 1B:
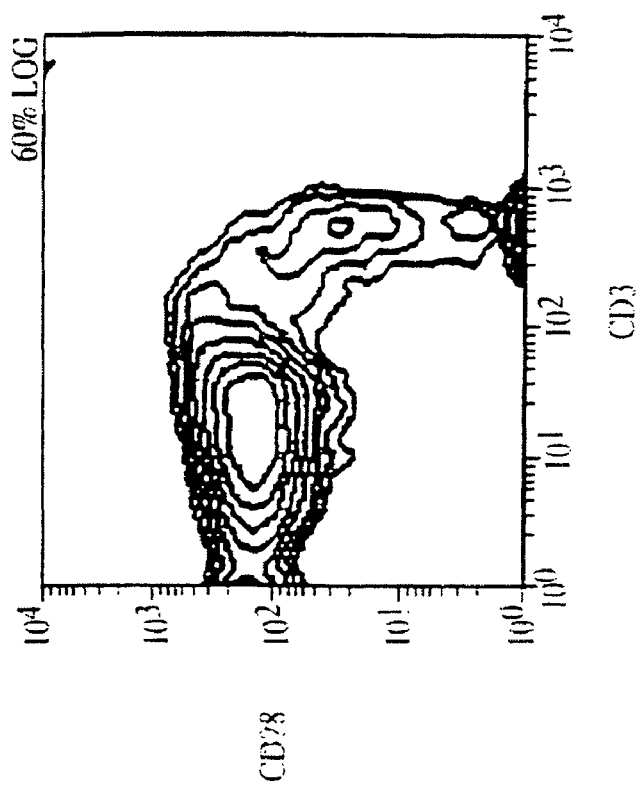
FIG. 1 shows the expression pattern for CD3, CD28, and AILIM (alternatively called ThA), in normal mouse thymus derived T cells.
Figure 1A:
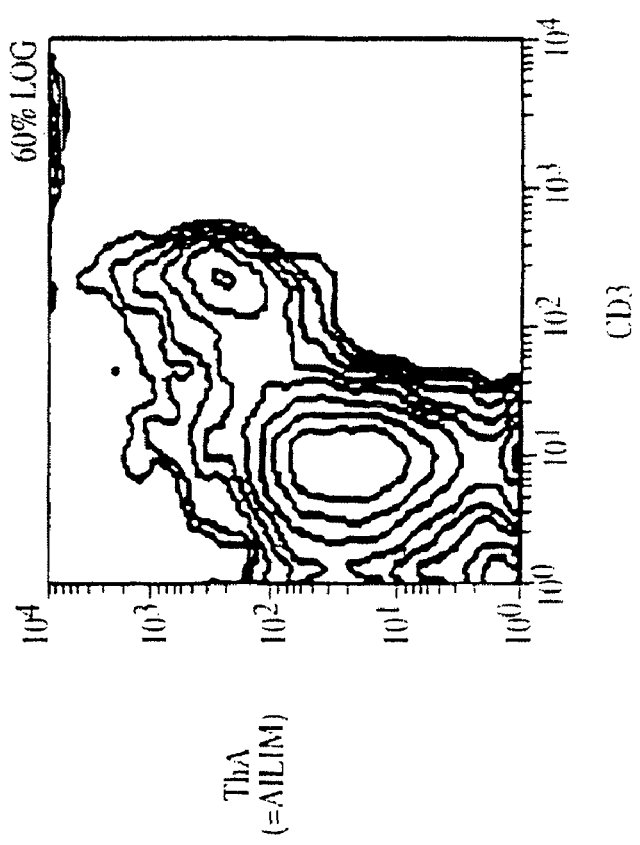

The result is shown in FIGS. 1 and 2. A new finding indicated below was revealed based on this result.

First, one of revealed in regard to the correlation between the expression of CD3 molecule and AILIM molecule is that the expression levels of AILIM are high in cells where the levels of CD3 expression are high; and thus the expression levels of the two molecules are correlated to each other (FIG. 1(*a*)). In contrast to that of the former molecule, the expression level of a costimulatory molecule CD28 was lower as the expression level of CD3 was higher (FIG. 1(*b*)). These results show that the expression patterns of AILIM and CD28 exhibit reciprocal correlation to that of CD3 at least in normal thymus T cells.

The differentiation and maturation of thymus T cell is known to be achieved through the following major steps.

(1) The CD4-negative CD8-negative cell (R2 in FIG. 2) differentiates to a CD4-weakly-positive CD8-weakly-positive cell (R3 in FIG. 2) in which the expression of each molecule is recognizable but weak.

(2) The CD4-weakly-positive CD8-weakly-positive cell (R3 in FIG. 2) differentiates to a CD4-positive CD8-positive cell (R4 in FIG. 2) in which both molecules are strongly expressed.

(3) The expression of either of CD4 and CD8 molecules is decreased (R5 or R7 in FIG. 2) through the positive selection; each type of cell eventually differentiates to a CD4-positive CD8-negative (R6 in FIG. 2) or CD4-negative CD8-positive (R8 in FIG. 2) cell and the maturation is thus completed.

Neither AILIM nor CD28 was recognizably expressed in CD4-negative CD8-negative cells but weak levels of expression were observed in CD4 weak-positive CD8 weak-positive cells. The expression of CD28 was maximized in CD4-positive CD8-positive cells and then decreased as the cells further differentiated to maturity.

On the other hand, only low-level expression of AILIM was found even in the CD4-positive CD8-positive cells. The level of AILIM expression was however elevated during the subsequent cell differentiation processes; namely, as the level of CD4 or CD8 expression decreased, the level of AILIM expression was elevated and then maximized at the final differentiation stage of lymphocyte of which positive selection is completed; the mature lymphocyte is called SP cell (CD4-positive CD8-negative cell or CD4-negative CD8-positive cell).

The experimental result shows that the expression pattern of AILIM is different from that of CD28 with respect to the correlation to the expression of CD4 and CD8 as well as that of CD3.

<2-3> Analysis of AILIM Expression in T Cells Derived from Mouse Normal Lymphoid Tissues The expression of AILIM in T cells of spleen and lymph node, which are mouse normal lymphoid tissues, was analyzed by the above-mentioned method.

The result is shown in FIG. 3.

Population of AILIM-positive T cell among spleen-derived T cells is smaller than that in the thymus, and the percentage was about 1 to 3%. Majority of the AILIM-positive cells were CD4-positive and CD8-negative.

The expression pattern of AILIM in lymph node-derived T cells and the percentage population were comparable to those in the above-mentioned spleen-derived T cells.

<2-4> Analysis of AILIM Expression in T Cells Obtained from Affected Tissues of Hepatitis Model Mouse Hepatitis Model Mice were Prepared as Follows:

A suspension of *Propionibacterium acnes* (*P. acnes*; 5 mg/ml) in phosphate buffer (PBS-; 0.2 ml) was intravenously injected into the tail of C57BL/6 mouse. After one week, a solution of LPS (lipopolysaccaride; 1.5 µg/ml) in phosphate buffer (PBS-; 0.2 ml) was intravenously injected into the mouse to induce hepatitis. The mouse was used as a hepatitis model animal.

6.5 hours after LPS administration, the liver was excised from the mouse; T cells were prepared from the cells by the above-mentioned method to analyze AILIM expression.

The result is shown in FIG. 4.

The expression level of AILIM was highly elevated in the T cells (mononuclear cells) derived from the liver tissue of the hepatitis model mouse; most of the T cells expressed AILIM at markedly high levels. The level of AILIM expression in T cells derived from the liver of the hepatitis model was considerably higher than those in spleen-derived T cells (CD4 positive cells) and lymph node-derived T cells from normal mouse.

<2-5> Analysis of AILIM Expression in Peripheral Blood-Derived T Cells from Healthy Normal Persons Analyses using flow cytometer were carried out to estimate the expression levels of AILIM in peripheral blood-derived T cells from healthy normal persons and human mononuclear cells isolated from peripheral blood samples collected from healthy normal persons as well as the expression of various cell surface markers on the cells. Peripheral blood T cells from healthy normal subjects were prepared by the above-mentioned method.

On the other hand, AILIM-expressing T cells (AILIM-positive cells) were obtained as follows: a fraction of mononuclear cells separated from peripheral blood of a healthy normal person were suspended in PBS—that contained 0.5% BSA and 5 mM EDTA, and anti-AILIM antibody (SG430; 50 µg) was added thereto. The mixture was incubated at 4° C. for 30 minutes. Subsequently, after the cells were washed 3 times with the same buffer, microbeads with immobilized goat anti-mouse IgG (100 to 500 µl; Miltenyi) were added thereto. The mixture was incubated in the same manner and then washed with the same buffer. In the next step, the cells were subjected to a treatment using magnetic separation column (twice) according to a usual method to isolate AILIM-positive cells. The isolated AILIM-positive cells were stained with each of a variety of labeled antibodies and anti-AILIM antibodies; the cells stained were analyzed by flow cytometer.

The result is shown in FIG. 24.

Peripheral blood T cells are primarily grouped into CD4-positive CD8-negative cells and CD4-negative CD8-positive cells. In the double staining test with FITC-labeled anti-AILIM antibody (SA12) and anti-CD4 antibody, the expression of AILIM was recognized mainly in CD4-positive cells. Double staining with the anti-AILIM antibody and anti-CD28 antibody revealed that almost all the peripheral blood-derived AILIM-positive cells expressed CD28. The percentage population of AILIM-positive cell in peripheral blood T cells was roughly estimated to 0.5 to 5%.

On the other hand, the following findings were obtained based on the analytical results for the surface markers of AILIM-positive cells directly separated from a fraction of mononuclear cells of human peripheral blood:

(1) majority of AILIM-positive cells were CD4-positive CD8-negative cells;

(2) among AILIM-positive cells, the presence of CD4-negative CD8-positive cells as well as CD4-negative CD8-negative cells was recognizable but their populations were small;

(3) double staining with the anti-AILIM antibody and anti-CD28 antibody revealed that most of AILIM-positive cells expressed CD28 and therefore most of the AILIM-positive cells were assigned to the class of T cell;

(4) some AILIM-positive cells were stained with an antibody against CD19 that is a B cell surface marker. This suggests that B cells also weakly express AILIM;

(5) the expression of CTLA4, which is a costimulatory molecule, was recognized in many of AILIM-positive cells.

In addition, the analysis was carried out to estimate the expression level of AILIM in peripheral blood T cells and AILIM-positive cells.

The result is shown in FIG. 25.

When the expression of AILIM in AILIM-positive cells was compared with that in peripheral blood T cells, the peaks shifted at different positions from each other indicating that the expression level of AILIM is higher in AILIM-positive cells.

Further, a similar comparative analysis was performed between CD4-positive cells and CD8-positive cells. Similar levels of AILIM expression were observed between the two fractions. The population of CD8-positive cells among AILIM-positive cells was small, but the expression level of AILIM in CD8-positive cells was similar to that in the remaining cells.

<2-6> Analysis of AILIM Expression in T Cells from Patients Affected with Various Arthritides or Autoimmune Diseases The expression of AILIM and the proportion of AILIM-expressing cells were analyzed in T cell from patients with arthritis (rheumatoid arthritis (RA) and osteoarthritis (OA)) or autoimmune diseases (progressive systemic sclerosis (PSS) and systemic lupus erythematosus (SLE)) according to the above-mentioned method.

T cells were separated from each of synovial fluid and peripheral blood of arthritis patients; T cells were also isolated from peripheral blood of patients with autoimmune disease. In addition, T cells of peripheral blood from healthy normal persons were used as a control.

The result is shown in FIGS. 5 and 26.

The expression of AILIM in peripheral blood-derived T cells from RA patients was compared with that in the cells from healthy normal persons. Between the patients and normal persons, the expression levels were not significantly different in CD4-positive T cells and also in CD4-negative T cells (namely CD4-negative CD8-positive T cells).

However, the population of AILIM-expressing cells was significantly increased among CD4-positive T cells and also among CD4-negative T cells in T cells derived from synovial fluids of RA patients. In particular, the averaged proportion of AILIM-expressing cells was increased to about 20% of total CD4-positive T cells. In addition, it was found that the expression level of AILIM was significantly elevated in CD4-positive T cells and CD4-negative T cells from synovial fluids of RA patients as compared with those in CD4-positive T cells and CD4-negative T cells derived from peripheral blood of healthy normal persons. The expression level of CD28 was not altered in CD4-positive T cells from RA patients.

On the other hand, in a single case of OA patient, the population of AILIM-positive cell was markedly elevated among CD4-positive cells derived from synovial fluid.

The population of AILIM-positive cells among CD4-negative T cells from peripheral blood of patients with autoimmune diseases was comparable to that among the cells from healthy normal persons. However, the population of AILIM-positive cell was significantly elevated among CD4-positive T cells from PSS patients as compared with that among the cells from healthy normal persons.

<2-7> Analysis of AILIM Expression in Adjuvant-Induced Arthritis Model Rat

Dead tubercle *bacillus* (*M. Tuberculosis* H37Ra; Difco) of 10 mg/ml in liquid paraffin (Wako pure chemical) was used as an adjuvant. The adjuvant was intracutaneously injected into Wistar rats (male, 5-week-old, Charles River) at a concentration of 1 mg/0.1 ml/individual in a tail head area to induce arthritis. The volume of both hind legs was measured by using a plethysmometer. The volume determined was used as an index for the onset of arthritis.

The thymus, spleen, lymph node and peripheral blood were collected over time after the administration of the adjuvant (0 day). T cell suspensions were prepared according to the above-mentioned method. The T cells were stained with each of anti-CD4 antibody, anti-CD8 antibody and anti-AILIM antibody by the above-mentioned method. Then the expression of CD4, CD8 and AILIM was analyzed by flow cytometer.

Control T cells used were those derived from the thymus, spleen, lymph node and peripheral blood of normal rats.

The result is shown in FIG. 27.

There were no recognizably significant differences in the expression of AILIM in CD4-positive T cells and CD8-positive T cells from the thymus, spleen and peripheral blood when compared with those in the control cells.

On the other hand, the population of AILIM-positive cell was significantly increased among lymph node-derived CD4-positive T cells as well as among CD8-positive T cells when compare to that among the control cells. In particular, the expression of AILIM reached a peak level on the fifth day after the adjuvant administration in CD4-positive T cells.

<2-8> Analysis of the Varying Level of AILIM Expression Associated with Mouse T Cell Activation Mouse T cell derived from lymphoid tissues were activated under a variety of conditions. The varying level of AILIM expression associated with T cell activation was analyzed.

T cells were activated by the addition of anti-CD3 antibody (final concentration: 1 to 10 μg/ml), concanavalin A (ConA; final concentration: 1 to 5 μg/ml), or PMA (phorbol myristate acetate; final concentration: 20 ng/ml) and Ca ionophore (final concentration: 200 ng/ml) to the suspension of T cells in 10% FCS-containing RPMI1640 medium for the stimulation. The expression of AILIM was analyzed over time (after 0, 6, 12, 24, and 48 hours) after addition of the activating agent.

The result is shown in FIG. 6.

The AILIM expression started to be up-regulated about 3 to 6 hours after the stimulation under any of the activation conditions and was maximized 12 hours after the stimulation. The level of AILIM expression remained to be high about 24 hours after the stimulation, and the high level was still maintained 48 hours after the stimulation.

<2-9> Analysis of the Induction of AILIM Expression Associated with Human T Cell Activation T cells derived from peripheral blood of healthy normal persons in the same manner as described above were activated by the method of (A) or (B) as descried below. The analysis was carried out for the T cell activation-associated expression of AILIM and CTLA-4 that is a costimulatory molecule.

(A) T Cell Activation by PMA and Ca Ionophore

PMA (final concentration: 20 ng/ml) and Ca ionophore (final concentration: 200 ng/ml) were added as activating agents to a suspension of human T cells ($1 \times 10^5$ cells) in 10% FCS-containing RPMI1640 medium for the stimulation. 8 hours after addition of the activating agents, the expression of AILIM and CTLA-4 was analyzed by flow cytometer.

(B) T Cell Activation by Anti-CD3 Antibody/Anti-AILIM Antibody or Anti-CD3 Antibody/Anti-CD28 Antibody Aliquots of solutions of (1) anti-CD3 antibody (clone OKT3; 200 ng/well) and anti-AILIM antibody (clone SA12; 1 μg/well) or solutions of (2) anti-CD3 antibody (clone OKT3; 200 ng/well) and anti-CD28 antibody (clone CD28.2; 1 μg/well) diluted in D-PBS were added to each well of a 96-well microplate and the plate was incubated at room temperature for 3 hours. The plate was thus coated with each antibody.

Suspension of peripheral blood-derived human T cells ($1 \times 10^5$ cells/ml, 0.1 ml/well) in 10% FCS-containing RPMI1640 medium was added to each plate. The cells were harvested after cultured for 2 to 3 days. The expression of AILIM and CTLA-4 was analyzed by using a flow cytometer according to the above-mentioned method.

The result is shown in FIG. 28.

A considerably high level of AILIM expression was induced 8 hours after the stimulation for T cell activation with PMA and the ionophore. The expression level was much higher than that of CTLA-4 expression that was also induced by the stimulation. Furthermore, AILIM expression was induced in almost all the T cells. In addition, double staining test for CD4 and AILIM, or for CD8 and AILIM, showed that the activation induced a significant level of AILIM expression in CD4-positive T cells as well as in CD8-positive T cells.

On the other hand, the following result was obtained in the activation test using a microplate that had been coated with anti-CD3 antibody/anti-AILIM antibody or anti-CD3 antibody/anti-CD28 antibody.

(1) A considerably high level of AILIM expression was induced in T cells activated by anti-CD3 antibody/anti-AILIM antibody as well as in T cells activated by anti-CD3 antibody/anti-CD28 antibody. The level of induced expression was higher in T cells activated by anti-CD3 antibody/anti-CD28 antibody than that in T cells activated by anti-CD3 antibody/anti-AILIM antibody.

(2) The expression of CTLA-4 was induced in T cells activated by anti-CD3 antibody/anti-AILIM antibody as well as in T cells activated by anti-CD3 antibody/anti-CD28 antibody. However, there were no significant differences in the level of induced expression between the T cells activated by anti-CD3 antibody/anti-AILIM antibody and the cells activated by anti-CD3 antibody/anti-CD28 antibody.

<2-10> Analysis of AILIM Expression in Various T Cell Lines

T cell lines are known to be established chiefly by spontaneous immortalization, or as T cell lines immortalized with chemical agent or as T cell hybridoma by fusing T cell with myeloma cell. T cell lines are grouped into two classes based on the property of cytokine production, namely Th1-type T cell lines and Th2-type T cell lines.

The expression of AILIM and CD28 in a variety of known mouse T cell lines as described above in <1-6> was analyzed with a flow cytometer by the same method as described above.

The result is shown in FIG. 7.

AILIM was recognized to be expressed constitutively in T cell lines exhibiting the property of Th2-type T cell line in regard to cytokine production (D10, MS202, CD28KO, EL-4, etc.). The level of AILIM expression was comparable or higher relative to that of CD28 in these cell lines.

On the other hand, the expression of AILIM was not recognizable although the level of CD28 expression was high in Th1-type T cell lines except 6-13-64.

EXAMPLE 3

Analysis of T Cell Response-Modulating Activity of Anti-AILIM Antibody

It was analyzed whether or not the anti-AILIM antibody of the present invention had the activities in modulating (enhancing and/or suppressing) T cell response (production of a cytokine such as IFN-γ and IL-4, cell proliferation, etc.), namely whether or not the antibody had the capability in regulating the transduction of AILIM-mediated costimulatory signal into cell. The analysis was carried out by using the quantities of cytokines (IFN-γ and IL-4) produced by the cells and the degree of cell proliferation as indices.

<3-1> Method for Testing

Depending each purpose of test, one or two types of antibodies (anti-CD3 antibody alone, anti-CD28 antibody alone, anti-CD3 antibody and anti-AILIM antibody, or anti-CD3 antibody and anti-CD28 antibody) prepared above were selected and added to wells of a 96-well microplate. The plate was incubated at 37° C. for 1 hour or more to coat the plate with one or two antibodies. The plate was then sufficiently washed with PBS. Subsequently, thymus cells ($5 \times 10^5$ cells/well), spleen cells ($2 \times 10^5$ cells/well) or purified T cells ($1 \times 10^5$ to $3 \times 10^5$ cells/well), which had been prepared in the above method, were added to the plate.

In a test in which the plate had not previously been coated with the anti-AILIM antibody or anti-CD28 antibody but either of the antibodies was simply added to the plate later, the antibody was added to the plate after the plating of the cells. Further, CTLA4-Ig (fusion protein between the soluble region of CTLA4 and IgFc) was used as a control instead of anti-AILIM antibody in the test. The test was performed according to the same method.

The plate was incubated for 2 to 4 days in a $CO_2$ incubator. The concentrations of cytokines (IFN-γ or IL-4) in the culture supernatant were determined by a commonly used ELISA method. Further, the degree of cell proliferation during the culture was evaluated by a common method utilizing tritium-labeled thymidine ($^3$H-TdR) incorporation.

<3-2> Analysis of Induction of Cytokine Production from T Cells Through the Transduction of Costimulatory Signal Mediated by Anti-CD3 Antibody and Anti-AILIM Antibody into the Cells It has been known that T cells produce specific cytokines in response to T cell receptor-mediated primary signal and secondary signal mediated by costimulatory molecules such as CD28 and CTLA-4.

The production of various cytokines induced by the stimulation with a variety of antibodies was analyzed by using peripheral blood T cells, thymus cells or spleen cells isolated from each of mouse, rat and human according to the above-mentioned test method as described in <3-1>.

<3-2-1> Induction of IFNγ in T Cells Derived from Mouse Spleen

T cells derived from mouse spleen were added to (1) a microplate coated with anti-CD3 antibody (clone 145-2C11; Pharmingen: 0 to 3 μg/ml) and anti-CD28 antibody (clone CD28.2; 1 μg/well); (2) a microplate coated with anti-CD3 antibody and anti-mouse AILIM antibody (clone B10.5; 1 μg/well); and (3) a microplate coated with anti-CD3 antibody alone. The plates were incubated to cultivate the cells and then quantities of IFNγ in the culture supernatants were determined by ELISA.

The result is shown in FIG. 8.

The production of IFNγ was not induced by the stimulation with anti-CD3 antibody alone. However, the production of IFNγ was significantly induced by the stimulation with anti-CD3 antibody/anti-AILIM antibody or anti-CD3 antibody/anti-CD28 antibody. The induction was enhanced depending on the concentration of anti-CD3 antibody.

<3-2-2> Induction of IFNγ Production in T Cells Derived from Rat Spleen

T cells derived from rat spleen were added to (1) a microplate coated with anti-CD3 antibody (clone G4.18; 50 ng/well) and anti-CD28 antibody (clone JJ316; 1 μg/well); (2) a microplate coated with anti-CD3 antibody and anti-rat AILIM antibody (clone JTT1; 1 μg/well); (3) a microplate coated with anti-CD3 antibody alone; (4) a microplate coated with anti-AILIM antibody alone; and (5) a microplate coated with anti-CD28 antibody alone. The plates were incubated to cultivate the cells and then quantities of IFNγ in the culture supernatants were determined by ELISA.

The result is shown in FIG. 9.

The production of IFNγ was not significantly induced by the stimulation with anti-CD3 antibody alone, anti-AILIM antibody alone, or anti-CD28 antibody alone. However, the production of IFNγ was significantly induced by the stimulation with anti-CD3 antibody/anti-AILIM antibody or anti-CD3 antibody/anti-CD28 antibody. The level of production resulted from the induction was elevated over time.

<3-2-3> Induction of IFNγ Production in Human T Cells Derived from Peripheral Blood Human T cells derived from peripheral blood were added to (1) a microplate coated with anti-CD3 antibody (clone OKT3; constant concentration) and anti-AILIM antibody (clone SA12; various concentrations); and (2) a microplate coated with anti-CD3 antibody alone. The plates were incubated to cultivate the cells and then quantities of IFNγ in the culture supernatants were determined by ELISA. In the test of (2), the solution of anti-AILIM antibody was added after the cells were added.

The result is shown in FIG. 10.

Even when the concentration of anti-AILIM antibody was raised up to 20 μg/ml, the induction of IFNγ production in the cells was not recognizable in the test in which T cells were added to a microplate coated with anti-CD3 antibody of a constant concentration and a solution of anti-AILIM antibody was added to the plate after the cells were added.

On the other hand, a considerably high level of induction in IFNγ production was found in human T cells cultured in a microplate coated with both anti-CD3 antibody and anti-AILIM antibody, when the concentration of anti-AILIM antibody was 5 μg/ml or higher.

It was also found that cytokine production and cell proliferation were enhanced in the T cells when peripheral blood-derived T cells stimulated with Con A or PMA were cultivated in a plate coated with both anti-AILIM antibody and anti-CD3 antibody in the same manner as shown above. The result was essentially the same as that obtained when peripheral blood-derived T cells stimulated with Con A or PMA were cultured in a plate coated with both anti-CD28 antibody and anti-CD3 antibody.

<3-2-4> Induction of TNFα, IFNγ, IL-2, IL-4 and IL-10 Production in Human T Cells Derived from Peripheral Blood T cells derived from peripheral blood each of two unrelated healthy normal donors were added to (1) a microplate coated with anti-CD3 antibody (clone OKT3; 200 ng/well) alone; (2) a microplate coated with anti-CD28 antibody (clone CD28.2; 1 μg/well) alone; (3) a microplate coated with anti-human AILIM antibody (clone SA12; 1 μg/well); (4) a microplate coated with anti-CD3 antibody and anti-CD28 antibody; (5) a microplate coated with anti-CD3 antibody and anti-AILIM antibody; and (6) a microplate coated with anti-CD3 antibody, anti-AILIM antibody and anti-CD28 antibody. The plates were incubated to cultivate the cells and then quantities of TNFα (tumor necrosis factor-α), IFNγ (interferon-γ), IL-2 (interleukin-2), IL-4 (interleukin-4) and IL-10 (interleukin-10) in the culture supernatants were measured over time (18, 40 and 64 hours) by ELISA.

It should be noted that TNFα, IFNγ and IL-2 are cytokines produced by Th1-type T cells; and IL-4 and IL-10 are cytokines produced by Th2-type T cells.

The result is shown in FIG. 29. The following result was obtained:

(1) There were no differences in the levels of induction of TNFα, IFNγ and IL-2 production between the donors.

(2) The levels of TNFα and IFNγ production were induced even when the stimulation was performed even with anti-CD3 antibody alone.

(3) The levels of induction of TNFα and IFNγ production were elevated additively by the stimulation with anti-CD3 antibody and anti-CD28 antibody or with anti-CD3 antibody and anti-AILIM antibody as compared with those by the stimulation with anti-CD3 antibody alone.

(4) In regard to IL-2, the production was induced by the stimulation with anti-CD3 antibody and anti-CD28 antibody, with anti-CD3 antibody and anti-AILIM antibody, or with anti-CD3 antibody, anti-CD28 antibody and anti-AILIM antibody. The level of induced IL-2 production was highest by the stimulation with anti-CD3 antibody, anti-CD28 antibody and anti-AILIM antibody.

(5) In regard to IL-4 and IL-10 that are Th2 cytokines, there are differences in the induction of production between the two donors. This suggests the possibility that the differences reflect the difference in population of T cells among human individuals.

(6) In regard to IL-4, the production was induced by the stimulation with anti-CD3 antibody and anti-CD28 antibody, with anti-CD3 antibody and anti-AILIM antibody, or with anti-CD3 antibody, anti-CD28 antibody and anti-AILIM antibody. The level of the induction in IL-4 production was highest by the stimulation with anti-CD3 antibody, anti-CD28 antibody and anti-AILIM antibody.

(7) In regard to IL-10, the production was induced by the stimulation with anti-CD3 antibody and anti-CD28 antibody, with anti-CD3 antibody and anti-AILIM antibody, or with anti-CD3 antibody, anti-CD28 antibody and anti-AILIM antibody. The stimulation with anti-CD28 antibody and anti-AILIM antibody resulted in the production of IL-10 at a considerably high level. Further, the level of induction in IL-10 production was highest by the stimulation with triple antibodies of anti-CD3 antibody, anti-CD28 antibody and anti-AILIM antibody.

The above-mentioned test indicates that the anti-CD3 antibody immobilized on the plate functioned as MHC on antigen-presenting cell and also the anti-AILIM antibody immobilized on the plate functioned as an AILIM ligand, resulting the primary signal and secondary stimulatory signal (co-stimulatory signal), which are responsible for T cell activation, were transduced into the added T cells.

<3-3> Inhibition, by Anti-AILIM Antibody, of Induction of Cytokine Production as a T Cell Response Induced by CD3-Mediated Signal It was tested whether or not each of anti-AILIM antibody and anti-CD28 antibody was capable of inhibiting the induction of IFNγ and IL-4 production as a T cell response induced when T cells were cultured in a microplate coated with anti-CD3 antibody.

Peripheral blood-derived T cells, thymus-derived T cells or spleen-derived T cells were plated in a microplate coated with anti-CD3 antibody alone, and then any one of anti-AILIM antibody (various concentrations), anti-CD28 antibody (various concentrations) or CTLA4-IgFc (control) was added thereto. The amounts of IFNγ or IL-4 in the culture supernatant were determined according to the method as described above in <3-1>.

The result is shown in FIGS. 11 to 14.

The addition of anti-AILIM antibody significantly inhibited the production of both IFNγ and IL-4 induced by anti-CD3 antibody stimulation in peripheral blood-derived T cells (FIGS. 11 and 12). The addition of anti-AILIM antibody also inhibited the proliferation of cells. On the other hand, the addition of anti-CD28 antibody inhibited neither the cytokine production nor the cell proliferation.

The addition of anti-AILIM antibody markedly inhibited anti-CD3 antibody-induced IL-4 production in thymus-derived T cells (FIG. 13). The addition of anti-AILIM antibody also inhibited the cell proliferation. On the other hand, the addition of CTLA4-IgFc as a control resulted in neither significant inhibition of IL-4 production nor significant inhibition of cell proliferation.

The addition of anti-AILIM antibody markedly inhibited anti-CD3 antibody-induced IL-4 production in spleen-derived T cells (FIG. 14). The addition of anti-AILIM antibody also inhibited the cell proliferation. On the other hand, the addition of CTLA4-IgFc as a control resulted in neither significant inhibition of IL-4 production nor significant inhibition of cell proliferation.

<3-4> Analysis of Induction of T Cell Proliferation Through the Transduction of Costimulatory Signal Mediated by Anti-CD3 Antibody and Anti-AILIM Antibody into T Cell T cells proliferate in response to T cell receptor-mediated primary signal and secondary signal mediate by costimulatory molecules such as CD28 and CTLA-4.

The proliferation of cells induced by the stimulation with a variety of antibodies was analyzed by using T cells derived from peripheral blood of healthy normal persons, mouse spleen cells, mouse spleen-derived T cells, and rat lymph node T cells according to the above-mentioned test method as described in <3-1>.

<3-4-1> Induction of Proliferation of Human T Cells Derived from Peripheral Blood Human T cells derived from peripheral blood were added to (1) a microplate coated with anti-CD3 antibody (clone OKT3; 200 ng/well; Ortho Diagnostic Systems) alone; (2) a microplate coated with anti-CD3 antibody and anti-CD28 antibody (clone CD28.2; various concentrations; Pharmingen); (3) a microplate coated with anti-CD3 antibody (200 ng/well) and anti-AILIM antibody (clone SA12; various concentrations); and (4) a microplate coated with anti-CD3 antibody (200 ng/well), anti-human AILIM antibody (various concentrations) and anti-CD28 antibody (1 μg/well). The plates were incubated to cultivate the cells and then the degree of cell proliferation was evaluated over time by a test of tritium-labeled thymidine ($^3$H-TdR) incorporation according to a commonly used method.

The result is shown in FIG. 30. The result of this test is as follows:

(i) The proliferation of human T cells derived from peripheral blood was significantly enhanced by any of the above-mentioned stimulations (2) to (4). The proliferation depended on the concentration of anti-AILIM antibody or anti-CD28 antibody immobilized on the plate.

(ii) The maximal degrees of induced T cell proliferation were comparable to one another among the stimulations with the above-mentioned antibody-coated plates of (2) to (4).

Subsequently, the degree of T cell proliferation was evaluated by using the microplates as indicated below in (5), (6) and (7) in the same manner as described above, in order to investigate the time course of proliferation of human peripheral blood-derived T cells induced by the stimulation with the above-mentioned various antibodies.

(5) A microplate coated with anti-CD3 antibody (200 ng/well) and anti-CD28 antibody (1 μg/well); (6) a microplate coated with anti-CD3 antibody (200 ng/well) and anti-AILIM antibody (1 μg/well); and (7) a microplate coated with anti-CD3 antibody (200 ng/well), anti-human AILIM antibody (1 μg/well) and anti-CD28 antibody (1 μg/well).

The result is shown in FIG. 31.

Proliferation of T cells was recognizable 18 hours after the stimulation in any of the antibody combinations. The stimulation with the combination of anti-CD3 antibody and antibody CD28 antibody (as described above in (5)) induced the highest level of T cell proliferation 40 hours after the antibody stimulation, but the activity of inducing T cell proliferation previously reached equilibrium with the combination.

On the other hand, the level of T cell proliferation induced by the stimulation with anti-CD3 antibody and anti-AILIM antibody (as described above in (6)) or with triple antibodies (as described above in (7)) reached a peak 60 hours after the stimulation. In these two types of combinations, T cell proliferation induced 60 hours after the stimulation with the antibodies were significantly higher than that in the combination of anti-CD3 antibody and anti-CD28 antibody.

<3-4-2> Induction of Proliferation of Mouse Spleen Cells and Mouse Spleen-Derived T Cells <3-4-2-1> Induction of Cell Proliferation in Microplates with Immobilized Antibody 96-well microplates were coated with anti-CD3 antibody (clone 145-2C11; Pharmingen; 50 ng/well). Then, the plates were further coated with various concentrations of anti-mouse AILIM antibody (clone B10.5) or anti-NP-KLH antibody as a control antibody. Mouse spleen cells or mouse spleen-derived T cells were added to wells of the plates coated each antibody. The plates were incubated to cultivate the cells and then the degree of cell proliferation was monitored by a test of tritium-labeled thymidine ($^3$H-TdR) incorporation according to a commonly used method.

The anti-NP-KLH antibody used as a control antibody was prepared by using as antigen NP-KLH, which is KLH (keyhole limpet hemocyanin; PIERCE) linked with NP (Nitrophenol) that is a hapten.

The result is shown in FIG. 32.

The stimulation with anti-NP-KLH antibody used as a control antibody resulted in neither the proliferation of mouse spleen cells nor the proliferation of mouse spleen-derived T cells. On the other hand, significant proliferation, which depended on the concentration of anti-AILIM antibody, was observed in all the cells when stimulated with anti-AILIM antibody.

<3-4-2-2> Induction of Cell Proliferation by Using Antibody-Immobilized Microbeads (Part 1)

Instead of microplate, latex microbead was used as a carrier on which antibody is immobilized. Cell proliferation test was carried out by using the bead in the same manner as described above.

In D-PBS, $1 \times 10^7$ microbeads were treated with (1) 1 μg/ml of anti-CD3 antibody (clone 145-2C11; Pharmingen) and various concentrations of anti-AILIM antibody (clone B10.5), or (2) 1 μg/ml of anti-CD3 antibody and various concentrations of anti-NP-KLH antibody. The mixtures containing beads were incubated for 1 hour or more, and then the beads were washed with D-PBS. The antibodies were thus immobilized on the beads.

C57BL/6 mouse spleen cells ($1\times10^5$/well) suspended in 10% FCS-containing RPMI1640 medium were added to each well of a 96-well microplate and the beads ($1\times10^5$ particles/well) were added thereto. The mixture was incubated for 56 hours. The degree of cell proliferation after the reaction was determined by tritium-labeled thymidine ($^3$H-TdR) incorporation test in a usual manner.

The result is shown in FIG. 33.

The proliferation of C57BL/6 mouse spleen cells was induced even either by the stimulation with anti-CD3 antibody and anti-AILIM antibody or by the stimulation with anti-CD3 antibody and anti-CD28 antibody. The degree of cell proliferation increased depending on increase of the concentration of anti-AILIM antibody or anti-CD28 antibody immobilized on the beads (increase in the ratio of concentration of anti-AILIM antibody or anti-CD28 antibody against anti-CD3 antibody concentration). In addition, the degree of cell proliferation was maximized when both ratio of anti-CD3 antibody concentration vs. anti-AILIM antibody concentration and ratio of anti-CD3 antibody concentration vs. anti-CD28 antibody concentration were 1:9.

<3-4-2-3> Induction of Cell Proliferation by Using Antibody-Immobilized Microbeads (Part 2)

Based on the result described above in <3-4-2-2>, the proliferation of mouse cells was analyzed in the same manner as described above by using latex beads coated with antibodies under a condition where both ratios of anti-CD3 antibody concentration vs. anti-AILIM antibody concentration and anti-CD3 antibody concentration vs. anti-CD28 antibody concentration were 1:9.

This test was conduced by using various concentrations of antibody-coated microbeads to be added to the suspension of mouse spleen cell ($1\times10^5$ cells/well).

Further, mouse cells used in the test were BALB/C mouse spleen cells and BALB/C mouse spleen-derived T cells.

In the test, a control experiment was similarly carried out by using microbeads on which anti-CD3 antibody alone was immobilized.

The result is shown in FIGS. 34 and 35.

The proliferation of both BALB/C mouse spleen cells and BALB/C mouse spleen-derived T cells was induced even either (1) by the stimulation with anti-CD3 antibody alone; (2) by the stimulation with anti-CD3 antibody and anti-AILIM antibody; or (3) by the stimulation with anti-CD3 antibody and anti-CD28 antibody.

The degree of cell proliferation increased depending on increase of the concentration of microbeads (namely, antibody concentration) added to the cell culture.

The proliferation of both BALB/C mouse spleen cell and BALB/C mouse spleen-derived T cell was maximized when the concentration of microbead added to the cell culture was 30,000 particles/well. The same result was obtained by using beads coated with anti-CD3 antibody and anti-AILIM antibody as well as by using microbeads coated with anti-CD3 antibody and anti-CD28 antibody.

<3-4-3> Induction of Proliferation of Rat Lymph Node T Cells

Rat lymph node T cells ($1\times10^5$ cells/well) suspended in 10% FCS-containing RPMI1640 medium were added to (1) a microplate coated with anti-CD3 antibody (clone G4.18; 50 ng/well) and anti-CD28 antibody (clone JJ319; various concentrations; Pharmingen); (2) a microplate coated with anti-CD3 antibody (50 ng/well) and anti-AILIM antibody (various concentrations); and (3) a microplate coated with anti-CD3 antibody (50 ng/well) and negative control antibody MOPC21 (various concentrations; Pharmingen). The plates were incubated in order to cultivate the cells at 37° C. for 44 hours. 6 hours before the end of the cultivation, tritium-labeled thymidine ($^3$H-TdR) was added to each well at a concentration of 0.5 µCi/well. After the culture was completed, the cells were harvested and then the amount of tritium-labeled thymidine ($^3$H-TdR) incorporated into cells was assayed in a TOPCOUNT (PACKARD). The degree of cell proliferation was analyzed based on the amount incorporated as an index.

The result is shown in FIG. 36. The following result was obtained in this test.

Although the proliferation of rat lymph node T cells was not induced by anti-CD3 antibody alone, the proliferation was significantly enhanced even either by the stimulation with anti-CD3 antibody and anti-AILIM antibody or by the stimulation with anti-CD3 antibody and anti-CD28 antibody. The proliferation depended on the concentration of anti-AILIM antibody or anti-CD28 antibody that was immobilized on the plate.

EXAMPLE 4

Therapeutic Effect of Anti-AILIM Antibody on Arthrosis

<4-1> Test with Multiple Administration of Anti-AILIM Antibody 10 mg/ml of Dead tubercle *bacillus* (*M. Tuberculosis* H37Ra; Difco) in liquid paraffin was used as an adjuvant. The adjuvant was intracutaneously injected into Wistar rats (male, 5-week-old, Charles River Inc.) at a dose of 0.1 ml/individual (1 mg/0.1 ml/individual) in a tail head area to induce arthrosis. 7 days after the administration of the adjuvant (0 day), the volume of both hind legs was measured by using a plethysmometer. The rats were divided into groups (8 individuals in each group) based on the volume of both hind legs as an index.

7 days after the administration of the adjuvant (0 day), anti-rat AILIM antibody (JTT-2 antibody; also referred to as JMab50; 20 mg/kg) was intravenously given to rats belonging to one of the groups. After the primary administration, the antibody was repeatedly given twice a week during the period from the start to the 20$^{th}$ day. By using a plethysmometer, the volume of both hind legs was measured over time from the primary adjuvant administration.

A control experiment was carried out in a group of normal rats (4 individuals) to which neither adjuvant nor antibody was given and in a negative-control group of rats to which mouse anti-human CETP antibody was given (clone JHC1; also referred to as JMab109; JP-A 9-20800), instead of anti-rat AILIM antibody. By using a plethysmometer, the volume of both hind legs was measured in the same manner.

The result is shown in FIG. 15.

Surprisingly, the paw swelling was completely suppressed in the group subjected to the administration of anti-AILIM antibody; the observed result is essentially the same as that observed with the group of normal rats in which arthritis was not induced.

<4-2> Test with Single Administration of Anti-AILIM Antibody (Part 1)

Based on the above-mentioned result, therapeutic effect of single administration of anti-AILIM antibody on arthritis was investigated in the same manner as described above.

In this test, anti-AILIM antibody or negative control antibody was intravenously administered only once on the third, fifth or seventh day after the adjuvant administration (0 day);

the anti-AILIM antibody and negative control antibody used were, respectively, anti-rat AILIM antibody (JTT-2 antibody; also referred to as JMab50; 20 mg/kg) and anti-rat CETP antibody (JHC1; 20 mg/kg).

The result is shown in FIG. 37.

The administration of the anti-AILIM antibody was conducted even only once, but the paw swelling was significantly suppressed in any cases where the antibody was given once on the third, fifth or seventh day after the adjuvant administration. In particular, in a group to which the anti-AILIM antibody was given on the seventh day after the adjuvant administration, the paw swelling was almost completely inhibited. The degree of the inhibition was substantially the same as that in the group of normal rats to which arthritis was not induced.
<4-3> Test with Single Administration of Anti-AILIM Antibody (Part 2)

Based on the result as described above in <4-2>, effective dosage of anti-AILIM antibody in the arthritis therapy was examined with the arthritis model in the test in the same manner as described above.

In this test, anti-rat AILIM antibody (JTT-2 antibody; also referred to as JMab50) of 1, 3, 10 or 20 mg/kg was intravenously administered only once on the seventh day after the adjuvant administration.

Further, in addition to JTT-2, another anti-rat AILIM antibody (JTT-1; also referred to as JMab-49; 20 mg/kg) was administered only once in the same manner for comparison.

As a negative control, anti-rat CETP antibody (JHC1; 20 mg/kg) was intravenously administered only once.

The result is shown in FIG. 38.

Even when the anti-AILIM antibody was administered only once at a dosage of 1, 3, 10 or 20 mg/kg, the paw swelling was almost completely inhibited. The degree of paw swelling was inhibited to substantially the same level in the group of normal rats to which arthritis was not induced. Surprisingly, the antibody exerted the inhibition effect even at a very low dose of 1 mg/kg.

EXAMPLE 5

Therapeutic Effect of Anti-AILIM Antibody on Hepatitis

A solution of *P. acnes* (*Propionibacterium acnes*) in phosphate buffer (PBS) was intravenously given to C57BL/6 mice. One week after the administration of *P. acnes* (0 day), a solution of LPS (Lipopolysaccharide) in PBS was intravenously administered to the mice to induce hepatitis. 6.5 hours after the LPS administration, blood was collected from the ocular fundus and then plasma IFN-γ concentration was determined by ELISA. In addition, concentrations of plasma GOT (glutamic-oxaloacetic transaminase) and GPT (glutamic-pyruvic transaminase) were measured in a biochemical analyzer (Fara).

1, 2 and 3 days after the administration of *P. acnes* (0 day), anti-mouse AILIM monoclonal antibody (B10.5 antibody; 5, 50, or 500 μg/individual) was intraperitoneally administered to the mice, and then the relieving effect of anti-AILIM antibody on hepatitis was evaluated.

The anti-mouse AILIM antibody was not given to a control group.

The result is shown in FIGS. 16 and 17.

The administration of anti-AILIM antibody significantly inhibited the elevation of blood IFN-γ level in an antibody concentration-dependent fashion. The administration of anti-AILIM antibody (50 μg/individual) also significantly inhibited the elevation of GOT and GPT levels.

EXAMPLE 6

Therapeutic Effect of Anti-AILIM Antibody on Graft-Versus-Host Disease (GVHD)

<6-1> Test 1

To induce GVHD, BALB/c mouse spleen cells ($8 \times 10^7$ cells/individual) were intravenously given to F1 mice (8- to 10-week-old, 3 individuals) obtained by the bleeding of BALB/c mouse and C57BL/6 mouse. Immediately and 12 hours after the administration of the spleen cells (0 hour), anti-mouse AILIM monoclonal antibody (B10.5 antibody; 400 μg/individual) was intravenously administered to the mice. 24, 48 and 72 hours after the administration of the spleen cells, B10.5 antibody (200 μg/individual) was intraperitoneally given to the mice.

Immediately, 1, 2, 3 and 6 weeks after the administration of the spleen cells (0 day), blood was collected from the mice. The IgG1, IgE and anti-dsDNA antibody titer in the sera were determined according to a usual method. The values of anti-dsDNA antibody titer were normalized by using an anti-dsDNA antibody in the serum from a spontaneous autoimmune disease mouse as a standard.

Instead of anti-AILIM antibody, hCTLA4-Ig (fusion protein between the soluble region of human CTLA4 and the constant region of immunoglobulin) was given to a positive-control group of mice in the same manner. In addition, instead of anti-AILIM antibody, PBS was given to a negative-control group in the same manner.

The result is shown in FIGS. 18 to 20.

The increase of serum IgG, IgE, and anti-dsDNA antibody titer as an index of GVH reaction (graft versus host reaction) was significantly suppressed in the group subjected to the administration of anti-AILIM antibody as compared with the negative control. Further, the suppressing effect was comparable to that observed in the positive control group subjected to the administration of hCTLA4-Ig.
<6-2> Test 2

To induce GVHD, BALB/c mouse spleen cells ($1 \times 10^8$ cells/individual) were intravenously given to F1 mice (8- to 10-week-old, 3 individuals) obtained by the bleeding of BALB/c mouse and C57BL/6 mouse. Immediately and 12 hours after the administration of the spleen cells (0 hour), anti-mouse AILIM monoclonal antibody (B10.5 antibody; 200 μg/individual) was intravenously administered to the mice. 24, 48 and 72 hours after the administration of the spleen cells, B10.5 antibody (100 μg/individual) was intraperitoneally given to the mice.

Immediately, 1, 2, 3, 6, 9 and 12 weeks after the administration of the spleen cells (0 day), blood was collected from the mice. The IgG1, IgE and anti-dsDNA antibody titer in the sera were determined according to a usual method. The values of anti-dsDNA antibody titer were normalized by using an anti-dsDNA antibody in the serum from a spontaneous autoimmune disease mouse as a standard.

Instead of anti-AILIM antibody, hCTLA4-Ig (fusion protein between the soluble region of human CTLA4 and the constant region of immunoglobulin) was given to a positive-control group of mice in the same manner. In addition, instead of anti-AILIM antibody, PBS was given to a negative-control group in the same manner.

The result is shown in FIGS. 39 to 41.

The increase of serum IgG, IgE, and anti-dsDNA antibody titer as an index of GVH reaction (graft versus host reaction)

was significantly suppressed in the group subjected to the administration of anti-AILIM antibody as compared with the negative-control group. Further, the suppressing effect was comparable to that observed in the positive control group subjected to the administration of hCTLA4-Ig.

EXAMPLE 7

Inhibitory Effect of Anti-AILIM Antibody on the Production of Anti-Foreign Antigen Antibody <7-1> Inhibitory Effect of Anti-AILIM Antibody on the Production of Anti-SRBC antibody in Mice Immunologically Sensitized with Sheep Red Blood Cell (SRBC)

Sheep red blood cells (SRBC; $1 \times 10^8$ cells/individual) were intravenously given to BALB/c mice (female, 5-week-old). Immediately or 7 days after the administration of SRBC (0 day), anti-mouse AILIM monoclonal antibody (B10.5 antibody; 50 or 500 μg/individual) was intravenously administered to the mice. Blood was collected overtime after the administration of SRBC. The anti-SRBC antibody produced in the serum was evaluated by a commonly used ELISA method.

Instead of anti-AILIM antibody, hCTLA4-Ig (fusion protein between the soluble region of human CTLA4 and the constant region of immunoglobulin) was given to a positive-control group of mice in the same manner. In addition, instead of anti-AILIM antibody, PBS was given to a negative-control group in the same manner.

The result is shown in FIGS. 21 and 22.

The production of IgG antibody specific to the foreign antigen SRBC was significantly inhibited in the group subjected to the administration of anti-AILIM antibody, in each case where the antibody was given immediately after the SRBC sensitization or where it was given 7 days after the sensitization, as compared with that in the negative-control group. The inhibitory effect was stronger than that in the positive-control group subjected to the administration of hCTLA4-Ig.

On the other hand, the production of anti-SRBC antibody was significantly inhibited in the group subjected to the administration of hCTLA4-Ig, in case where the hCTLA4-Ig was given immediately after SRBC sensitization, as compared with that in the negative-control group. However, no significant inhibition was found in case where it was given 7 days after SRBC sensitization.

<7-2> Inhibitory Effect of Anti-AILIM Antibody on the Production of Anti-NP-KLH Antibody in Mice Immunologically Sensitized with NP-KLH CFA (Freund's Complete Adjuvant) and NP-KLH (KLH (keyhole limpet hemocyanin) chemically linked to a hapten NP (Nitrophenol); 100 μg/mouse) were intraperitoneally administered to C57BL/6 mice. Immediately and 12 hours after the administration of the antigen (0 hour), anti-mouse AILIM antibody (either of clone B10.5 and B9.B6; 200 μg/mouse) was given to the tail vein. 24 and 48 hours after the administration of the antigen, either of the two anti-AILIM antibodies was intraperitoneally given to the mice.

Blood was collected over time after the administration of NP-KLH. The quantity of each NP-KLH-specific antibody (IgG1, IgG2a, IgG2b or IgM) produced in the serum was estimated by a commonly used ELISA method. In this ELISA experiment, NP-conjugated bovine serum albumin (BSA) was used as a capture antigen.

In this test, negative and positive control experiments were carried out, respectively by using phosphate buffer and hCTLA4-Ig (fusion protein between the soluble region of human CTLA4 and the constant region of immunoglobulin), with the same treatment procedure as described above.

The result is shown in FIGS. 42 to 46.

The amount of anti-NP-KLH antibody produced was increased over time in a group subjected to the administration of negative-control antibody. Thus the negative-control antibody did not inhibit the production of anti-NP-KLH antibody.

On the other hand, the production of anti-NP-KLH antibody was significantly inhibited in the group subjected to the administration of anti-AILIM antibody. The degree of inhibition was almost comparable to the effect of inhibiting production of anti-NP-KLH antibody exerted by CTLA4-IgFc that was a positive control.

The production of any anti-NP-KLH antibodies belonging to antibody classes, IgG1, IgG2a, IgG2b or IgM, was significantly inhibited in the group subjected to the administration of anti-AILIM antibody.

EXAMPLE 8

Analysis for the Activity of Anti-AILIM Antibody Modulating Mixed Lymphocyte Reaction (MLR)

It was analyzed whether or not anti-AILIM antibody had the activities in modulating (enhancing and/or suppressing) T cell response (production of a cytokine such as IFN-γ and IL-4, cell proliferation, etc.), namely whether or not the antibody had the capability in modulating the transduction of AILIM-mediated costimulatory signal into cell. The analysis was carried out by utilizing as an index the presence or absence of the activity in modulating T cell proliferation (namely, DNA synthesis in cell) in response to allogenic mixed lymphocyte reaction (allogenic MLR).

<8-1> Preparation of Human PBMCs and T Cells

Peripheral blood samples (200 ml) collected from healthy normal subjects (7 individuals; referred to as donors A, B, C, D, E, F and G) were placed on the layers of lymphoprep (15 ml; Nycomed) in microtubes (50 ml; Falcon). Subsequently, the tubes were centrifuged (at 1600 rpm for 10 minutes) and then the resulting intermediate layers were recovered. The recovered cells were diluted 2-fold or more with phosphate buffer and then centrifuged (at 1,800 rpm for 10 minutes) to prepare PBMC (peripheral blood mononuclear cells; $2 \times 10^8$ to $5 \times 10^8$ cells). The cell count was determined with a hemocytometer. An aliquot of the cells ($1.08 \times 10^8$ cells in 9 microplates) was taken for the MLR test and stored on ice. The remaining cells were used to separate T cells as follows:

The separation of T cells from PBMCs was carried out by using a Pan T Isolation kit (Miltenyi Biotech). According to the instruction manual attached to the kit, the remaining PBMCs were added and allowed to react in the solution contained in the kit. Subsequently, the cells were washed with PBS containing 5 mM EDTA and 0.5% BSA, and then re-suspended in PBS. The cell suspension was then added to Positive Selection Column VS+ (Miltenyi Biotech) swollen with PBS. The unadsorbed fraction was recovered. The column was washed with PBS. The washing solution was recovered. The washing treatment was carried out again. The recovered solutions were combined together to yield a T cell fraction. The T cell fraction was centrifuged and then the cells were re-suspended in PBS. The resulting T cells were counted by using a hemocytometer. The cells were used in the following test.

<8-2> Mixed Lymphocyte Reaction (MLR)

As described earlier, two signaling pathways between CD28 and CD80 (B7-1)/CD86 (B7-2) and between CTLA4 and CD80 (B7-1)/CD86 (B7-2), for which there have previously been comparatively detailed analyses, are known as costimulatory signaling pathways required for the activation of lymphocytes such as T cell, etc.

Namely, the proliferation of T cell in response to mixed lymphocyte reaction (MLR) can be also induced by the signal transduction through each of the two known pathways.

Thus, by using the substances as indicated below, this test was conducted to analyze (1) the inhibition of MLR by blocking the CTLA4-mediated signaling pathway; (2) the inhibition of MLR by blocking the CD80 (B7-1)/CD86 (B7-2)-mediated signaling pathway; and (3) the inhibition of MLR by blocking the tertiary signaling pathway associated with AILIM.

The followings were used as the test substances.

(1) mouse anti-human AILIM monoclonal antibody SA12 (same as in the above Example).

(2) mouse IgG antibody (anti-human CD34 antibody; negative control; Immunotech).

(3) a mixture of anti-human CD80 monoclonal antibody (Pharmingen) and anti-human CD86 monoclonal antibody (Pharmingen).

(4) human CTLA4-IgFc chimeric molecule (Ancell).

The mixed lymphocyte reaction (MLR) was conducted in the following 6 combinations using PBMCs and T cells prepared from the donors described above in <8-1>.

(i) T cell (donor A)/PBMC (donor D)
(ii) T cell (donor D)/PBMC (donor B)
(iii) T cell (donor C)/PBMC (donor A)
(iv) T cell (donor E)/PBMC (donor G)
(v) T cell (donor F)/PBMC (donor E)
(vi) T cell (donor G)/PBMC (donor F)

The concentrations of PBMCs and T cells to be used in the test were adjusted as described below.

PBMCs were suspended in PBS, and then transferred into culture dishes (60-mm). The cells were subjected to X-ray irradiation (50 Gy) with an irradiator (Hitachi MEDICO). The cells were recovered, centrifuged and then added to 10% FCS-containing RPMI1640 medium. The cell count was adjusted to $2 \times 10^5$ cells/50 µl.

The resulting T cells from each donor were also added to 10% FCS-containing RPMI1640 medium and the cell count was adjusted to $1 \times 10^5$ cells/50 µl.

<8-2-1> Inhibition of MLR by Anti-AILIM Antibody

PRMI1640 medium containing 10% FCS was added to each well of a 96-well microplate having U-shaped wells. A solution of mouse anti-human AILIM monoclonal antibody SA12 was diluted with 10% FCS-containing RPMI1640 medium to prepare solutions with various concentrations of the antibody. The diluted antibody solutions were added to the wells (final concentration: 0, 0.31, 1.25, 5 and 20 µg/ml). Subsequently, T cells (50 µl) were added to the wells. The plate was incubated at 37° C. for 1 hour in a $CO_2$ incubator (NAPCO). After the reaction was completed, PBMCs (50 µl) derived from a different donor were added to the wells to initiate the MLR.

When MLR was conducted by using a substance other than anti-human AILIM antibody as the test substance, T cells derived from a different donor were allowed to react after the incubation of PBMCs with the test substance.

On the fifth day of the culture, tritium-labeled thymidine ($^3$H-Thymidine; 20 µl; 1 µCi/well) diluted with 10% FCS-containing RPMI1640 medium was added to each well. The culture was continued for one day. After the culture was completed, the cells were harvested by using a Cell Harvester (Packard). The radioactivity of $^3$H incorporated in the cells was measured in a β counter (TOP COUNT; Packard) to analyze the rate of T cell proliferation after the culture.

The result is shown in FIGS. 47 to 52.

The result is summarized as follows:

(1) CTLA4-IgFc blocks the CTLA-4-mediated signal transduction, and thereby inhibiting the allogenic MLR-induced proliferation of T cell.

(2) Anti-CD80 antibody and anti-CD86 antibody inhibit the signal transduction mediated by CD80/CD86, which is a ligand for CTLA4 and CD28, and thereby inhibiting the allogenic MLR-induced proliferation of T cell.

(3) An antibody against human AILIM, like CTLA4-IgFc, anti-CD80 antibody and anti-CD86 antibody, significantly inhibits the allogenic MLR-induced T cell proliferation through the AILIM-mediated signal transduction in an anti-AILIM antibody concentration-dependent manner.

(4) The significant inhibition of MLR by anti-AILIM antibody can be achieved in any combination of in PBMCs or T cells derived from the donors.

In other words, these results show that costimulatory signaling pathways required for T cell activation include the tertiary pathway through which the signal is mediated by AILIM and the ligand thereof in addition to the known pathways mediated by CTLA4/CD80/CD86 and mediated by CD28/CD80/CD86 as well as that the AILIM-mediated signaling pathway is inhibited by antibody against AILIM.

Furthermore, it raises the possibility that the contribution of AILIM-mediated pathway to the signal transduction may be comparable to those of CTLA4/CD80/CD86-mediated pathway and CD28/CD80/CD86-mediated pathway.

INDUSTRIAL APPLICABILITY

The pharmaceutical composition of the present invention is useful for treating or prophylaxis of below-mentioned various autoimmune diseases, allergic diseases, or inflammatory diseases caused by the activation of lymphocytes such as T cells and the abnormality of regulation of activated lymphocyte functions.

Examples of the diseases are arthrosis (for example, rheumatoid arthritis, osteoarthritis), inflammation [for example, cerebritis, bronchitis, angiitis, pneumonia, hepatitis, myocarditis, pancreatis, intestinal enteritis, gastritis, peritonitis, nephritis (for example, glomerular nephritis), arthritis (for example, rheumatoid arthritis), inflammation in postischemic reperfusion injury (myocardial ischemic reperfusion injury), inflammation attributed to immune rejection, inflammatory bowel diseases, burn, inflammation in multiple organ failure, inflammation after operation of PTCA or PTCR, inflammation accompanying arteriosclerosis], various conditions caused by bacterial or viral infection (for example, inflammation), graft versus host reaction, immune rejection accompanying graft versus host reaction, transplantation of tissue(s) and organ(s), various diseases accompanied by excessive production of an antibody against a foreign antigen, caused by immunization with the foreign antigen, multiple sclerosis, autoimmune thyroiditis, various skin inflammation (allergic contact-type dermatitis, lichen planus which is chronic inflammatory skin disorder, psoriasis, scleroderma), and systemic lupus erythematosus.

A pharmaceutical composition comprising a human antibody against AILIM included in the pharmaceutical composition of the present invention is extremely useful as medicine because it completely excludes any side effects, for example, allergy at the administration of a mouse-derived antibody to human.

The invention claimed is:

1. A method of preventing graft versus host reaction in a subject, the method comprising administering to the subject an effective amount of a composition comprising (a) an antibody or a portion thereof that binds to human AILIM, and (b) a pharmaceutically acceptable carrier.

2. The method of claim 1, wherein the antibody or portion thereof is a monoclonal antibody.

3. The method of claim 2, wherein the monoclonal antibody is a chimeric monoclonal antibody, a humanized monoclonal antibody, or a human monoclonal antibody.

4. The method of claim 1, wherein the antibody or portion thereof is an F(ab')$_2$ fragment, an Fab' fragment, an Fab fragment, an Fv fragment, or a single domain antibody.

5. A method of treating graft versus host reaction in a subject, the method comprising administering to the subject an effective amount of a composition comprising (a) an antibody or a portion thereof that binds to human AILIM, and (b) a pharmaceutically acceptable carrier.

6. The method of claim 5, wherein the antibody or portion thereof is a monoclonal antibody.

7. The method of claim 6, wherein the monoclonal antibody is a chimeric monoclonal antibody, a humanized monoclonal antibody, or a human monoclonal antibody.

8. The method of claim 5, wherein the antibody or portion thereof is an F(ab')$_2$ fragment, an Fab' fragment, an Fab fragment, an Fv fragment, or a single domain antibody.

9. A method of preventing graft versus host reaction in a subject, the method comprising administering to the subject an effective amount of a composition comprising (a) an antibody that binds to human AILIM, and (b) a pharmaceutically acceptable carrier.

10. A method of treating graft versus host reaction in a subject, the method comprising administering to the subject an effective amount of a composition comprising (a) an antibody that binds to human AILIM, and (b) a pharmaceutically acceptable carrier.

* * * * *